United States Patent

Inoue et al.

[11] Patent Number: 5,807,860
[45] Date of Patent: Sep. 15, 1998

[54] UREA DERIVATIVES

[75] Inventors: Shinya Inoue; Masao Taniguchi; Yoshihiro Tarao; Kazuo Suzuki; Chizuko Takahashi; Mizue Kawai; Masayuki Mitsuka, all of Kanagawa, Japan

[73] Assignee: Mitsubishi Chemical Corporation, Tokyo, Japan

[21] Appl. No.: 748,612

[22] Filed: Nov. 13, 1996

[30] Foreign Application Priority Data

Nov. 13, 1995 [JP] Japan .................................. 7-294048

[51] Int. Cl.$^6$ .................. A61K 31/495; A61K 31/53; C07D 241/02; C07D 403/02
[52] U.S. Cl. .................. 514/255; 514/241; 514/242; 514/252; 544/179; 544/180; 544/182; 544/212; 544/238; 544/295; 544/357; 544/360; 544/364; 544/366; 544/370; 544/371; 544/372; 544/393; 544/400
[58] Field of Search .................. 544/179, 180, 544/182, 212, 238, 357, 400, 370, 371, 366, 372, 360, 393, 364, 295; 514/241, 242, 252, 255

[56] References Cited

U.S. PATENT DOCUMENTS

| | | | |
|---|---|---|---|
| 5,063,247 | 11/1991 | Sekiya et al. | 514/585 |
| 5,202,351 | 4/1993 | Sekiya et al. | 514/450 |
| 5,442,060 | 8/1995 | Jikihara et al. | 544/106 |
| 5,462,958 | 10/1995 | Hayashi | 514/399 |

FOREIGN PATENT DOCUMENTS

| | | |
|---|---|---|
| 2 063 170 | 9/1992 | Canada . |
| 0 405 233 | 1/1991 | European Pat. Off. . |
| 0 439 059 | 7/1991 | European Pat. Off. . |
| 0 506 532 | 9/1992 | European Pat. Off. . |
| 0 591 830 | 4/1994 | European Pat. Off. . |
| WO94/02452 | 2/1994 | WIPO . |

OTHER PUBLICATIONS

Kimura et al., J. Med. Chem., vol. 36 (1993) pp. 1630–1640.
Kimura et al., J. Med. Chem., vol. 36 (1993) pp. 1641–1653.

*Primary Examiner*—Mukund J. Shah
*Assistant Examiner*—Brenda Coleman
*Attorney, Agent, or Firm*—Wenderoth, Lind & Ponack, L.L.P.

[57] ABSTRACT

A compound represented by formula (I) and a salt thereof, and a hydrate and solvate thereof:

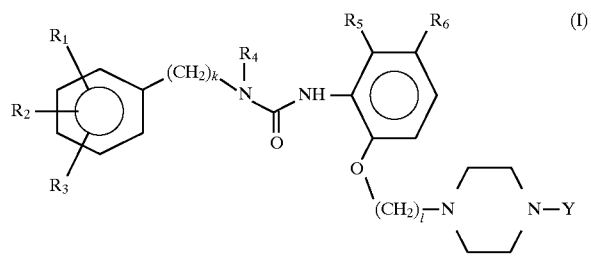

wherein $R_1$, $R_2$ and $R_3$ represent independently, for example, hydrogen atom, hydroxyl group, or $C_{1-3}$ alkoxy group; $R_4$ represents, for example, $C_{1-7}$ alkyl group or $C_{3-7}$ cycloalkyl group; $R_5$ and $R_6$ represent independently, for example, hydrogen atom or $C_{1-3}$ alkyl group; Y represents $C_{1-3}$ alkyl group, a heterocyclic group containing 1 to 4 nitrogen atoms and 5 or 6 ring-membered atoms, or $C_{6-10}$ aryl group; k represents an integer of 1 to 3; and l represents an integer of 2 to 4. These urea compounds have excellent inhibitory activities against ACAT and are useful as active ingredients of medicines for preventive and/or therapeutic treatment of hyperlipemia and atherosclerosis.

16 Claims, No Drawings

UREA DERIVATIVES

FIELD OF THE INVENTION

The present invention relates to novel urea derivatives which are useful as active ingredients of medicines used for the therapeutical and preventive treatments of diseases such as hyperlipemia and arteriosclerosis.

BACKGROUND ART

It has been considered that hyperlipemia caused by metabolic disorder of lipids results in arteriosclerosis, and is a risk factor for diseases such as ischemic heart disease or cerebral infarction. Current therapeutics for hyperlipemia and arteriosclerosis are mainly applied to reduce blood cholesterol level. However, no medicine is available at present that is expected to inhibit the formation of arteriosclerotic lesions or achieve regression. Recently, it was revealed that acyl coenzyme cholesterol acyl transferase (ACAT) plays an important role in lipid metabolism, particularly in cholesterol metabolism. Compounds having inhibitory activity against the enzyme ACAT lower blood cholesterol level by the inhibition of cholesterol absorption in the intestinal tract and the reduction of the formation of very low density lipoprotein (VLDL) in liver. Furthermore, at the artery wall, they prevent the foam cell formation and the accumulation of cholesterol esters, and thus, they are expected to regress the arteriosclerotic lesions.

Urea derivatives having inhibitory activity against ACAT are disclosed in, for example, Japanese Patent Unexamined Publication Nos. (Hei)5-9179/1993, (Hei)5-32666/1993, (Hei)5-132463/1993, (Hei) 5-140102/1993, (Hei)5-170727/1993, (Hei)5-194475/1993, (Hei)5-208948/1993, (Hei)5-310678/1993, (Hei)5-339223/1993, (Hei)5-923950/1993, (Hei)6-172288/1994, (Hei)6-247923/1994, (Hei)6-263736/1994, (Hei)6-340647/1994, (Hei)7-2782/1995, (Hei)7-33660/1995, Japanese Patent Unexamined Publication of International Application Nos. (Hei)5-508654/1993, (Hei)6-500095/1994, and (Hei)6-501252/1994.

DISCLOSURE OF THE INVENTION

The object of the present invention is to provide compounds having higher inhibitory activity against the enzyme ACAT and can exhibit activity on blood cholesterol reduction and inhibition of foam cell formation. Another object of the present invention is to provide medicines which comprise the compounds characterized by the aforementioned features and are useful for the preventive and therapeutic treatment of hyperlipemia and the preventive or therapeutic treatment of atherosclerosis. Further object of the present invention is to provide medicines which are characterized by the aforementioned features and are highly safe.

As a result of continuous and creative research to achieve the foregoing objects, the inventors found novel urea derivatives and their salts having extremely potent inhibitory activity against the enzyme ACAT in macrophage. The present invention was achieved on the basis of the findings.

The present invention thus provides urea derivatives represented by the following formula (I):

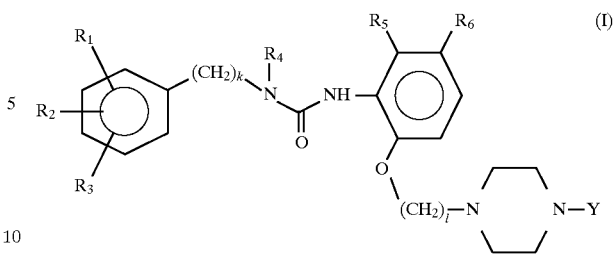

and their salts, and hydrates and solvates thereof. In the above formula (I), $R_1$, $R_2$ and $R_3$ represent independently hydrogen atom, hydroxyl group, a $C_1$–$C_3$ alkoxy group, Het-$(CH_2)_m$—O— (Het represents a heterocyclic group containing 1 or 2 nitrogen atoms and having 5 or 6 ring-membered atoms and m represents an integer of 1 to 3), a $C_7$–$C_9$ aralkyloxy group, or a heterocyclic group containing 1 to 4 nitrogen atoms and 5 or 6 ring-membered atoms, alternatively, $R_1$ and $R_2$ may form a ring of —O—$(CH_2)_n$—O— together to which $R_1$ and $R_2$ are bonded, wherein n represents an integer of 1 to 3. $R_4$ represents a $C_1$–$C_7$ alkyl group, a $C_3$–$C_7$ cycloalkyl group or Ar—$(CH_2)_p$— (Ar represents a $C_6$–$C_{10}$ aryl group and p represents an integer of 1 to 3). $R_5$ and $R_6$ represent independently hydrogen atom or a $C_1$–$C_3$ alkyl group, alternatively, $R_5$ and $R_6$ may form a ring of —$(CH_2)_q$ together with the ring to which $R_5$ and $R_6$ are bound, wherein q represents an integer of 3 to 5. Y represents a $C_1$–$C_3$ alkyl group, a heterocyclic group containing 1 to 4 nitrogen atoms and 5 or 6 ring-membered atoms, or a $C_6$–$C_{10}$ aryl group, k represents an integer of 1 to 3, and l represents an integer of 2 to 4.

According to preferred compounds of the present invention, there are provided:

(1) the compounds of the above-shown general formula (I) and their salts, and hydrates and solvates thereof characterized in that:

$R_1$, $R_2$ and $R_3$ represent independently hydrogen atom, hydroxyl group, a $C_1$–$C_3$ alkoxy group, Het-$(CH_2)_m$—O— (Het represents pyrrolyl group, imidazolyl group, pyrazolyl group, pyridyl group, pyrazinyl group, pyrimidinyl group, pyridazinyl group, pyrrolidinyl group, pyrrolinyl group, imidazolidinyl group, imidazolinyl group, pyrazolidinyl group, pyrazolinyl group, piperidyl group, or piperazinyl group and m represents an integer of 1 to 3), phenyl-($C_1$–$C_3$) alkoxy group, pyrrolyl group, imidazolyl group, pyrazolyl group, pyridyl group, pyrazinyl group, pyrimidinyl group, pyridazinyl group, pyrrolidinyl group, pyrrolinyl group, imidazolidinyl group, imidazolinyl group, pyrazolidinyl group, pyrazolinyl group, piperidyl group, piperazinyl group, triazolidinyl group, triazolyl group, triazinyl group, tetrazolyl group, and tetrazinyl group, alternatively, $R_1$ and $R_2$ may form a ring of —O—$(CH_2)_n$—O— together to which $R_1$ and $R_2$ are bonded, wherein n represents an integer of 1 to 3;

$R_4$ represents a $C_1$–$C_7$ alkyl group, a $C_3$–$C_7$ cycloalkyl group or Ar—$(CH_2)_p$—0 (Ar represents phenyl group, tolyl group, or naphthyl group, and p represents an integer of 1 to 3;

$R_5$ and $R_6$ represent independently hydrogen atom or a $C_1$–$C_3$ alkyl group, alternatively, $R_5$ and $R_6$ may form a ring of —$(CH_2)_q$ together to which $R_5$ and $R_6$ are bound, wherein q represents an integer of 3 to 5;

Y represents a $C_1$–$C_3$ alkyl group, pyrrolyl group, imidazolyl group, pyrazolyl group, pyridyl group, pyrazinyl group, pyrimidinyl group, pyridazinyl group, pyrrolidinyl group, pyrrolinyl group, imidazolidinyl group, imidazolinyl group, pyrazolidinyl group, pyrazolinyl group, piperidyl group, piperazinyl group, triazolidinyl group, triazolyl group, triazinyl group, tetrazolyl group, and tetrazinyl group, phenyl group, tolyl group, or naphthyl group; and k represents an integer of 1 to 3 and l represents an integer of 2 to 4;

(2) the compounds of the above-shown general formula (I) and their salts, and hydrates and solvates thereof characterized in that:

$R_1$, $R_2$ and $R_3$ represent independently hydrogen atom, hydroxyl group, a $C_1$–$C_3$ alkoxy group, Het-$(CH_2)_m$—O— (Het represents pyridyl group, and m represents an integer of 1 to 3), phenyl-$(C_1$–$C_3)$alkoxy group, pyrrolyl group, imidazolyl group, pyrazolyl group, or triazolyl group, alternatively, $R_1$ and $R_2$ may form a ring of —O—$(CH_2)_n$—O— together to which $R_1$ and $R_2$ are bonded, wherein n represents an integer of 1 to 3;

$R_4$ represents a $C_1$–$C_7$ alkyl group, a $C_3$–$C_7$ cycloalkyl group, or Ar—$(CH_{2p}$— (Ar represents phenyl group, and p represents an integer of 1 to 3;

$R_5$ and $R_6$ represent independently hydrogen atom or a $C_1$–$C_3$ alkyl group, alternatively, $R_5$ and $R_6$ may form a ring of —$(CH_2)_q$ together with the ring to which $R_5$ and $R_6$ are bound, wherein q represents an integer of 3 to 5;

Y represents a $C_1$–$C_3$ alkyl group, pyridyl group, or phenyl group; and k represents an integer of 1 to 3 and l represents an integer of 2 to 4;

(3) the compounds of the above-shown general formula (I) and their salts, and hydrates and solvates thereof characterized in that:

$R_1$, $R_2$ and $R_3$ represent independently hydrogen atom, a $C_1$–$C_3$ alkoxy group, Het-$(CH_2)_m$—O— (Het represents 2-pyridyl group, 3-pyridyl group, or 4-pyridyl group, and m represents 1), phenylmethyloxy group, 1-pyrrolyl group, 1-imidazolyl group, 1-pyrazolyl group, or 1-triazolyl group, with a proviso that $R_1$ and $R_2$ may form a ring of —O—$(CH_2)_n$—O— (n represents 1);

$R_4$ represents a $C_1$–$C_7$ alkyl group, cyclopentyl group, or Ar—$(CH_2)_p$— (Ar represents phenyl group and p represents 1 or 3);

$R_5$ represents a $C_1$–$C_3$ alkyl group and $R_6$ represents hydrogen atom, alternatively, $R_5$ and $R_6$ may form a ring of —$(CH_2)_q$— (q represents 4);

Y represents 2-pyridyl group or phenyl group; and k represents 1 or 2 and l represents 3;

(4) the compounds of the above-shown general formula (I) and their salts, and hydrates and solvates thereof characterized in that:

at least one of $R_1$, $R_2$ and $R_3$ represents Het-$(CH_2)_m$—O— (Het represents 2-pyridyl group or 3-pyridyl group, and m represents 1), 1-imidazolyl group, or 1-triazolyl group;

$R_4$ represents n-propyl group, n-pentyl group, cyclopentyl group, or Ar—$(CH_2)_p$— (Ar represents phenyl group and p represents 1 or 3);

$R_5$ represents methyl group and $R_6$ represents hydrogen atom, alternatively, $R_5$ and $R_6$ may form a ring of —$(CH_2)_q$— (q represents 4);

Y represents phenyl group; and k represents 1 or 2 and l represents 3; and (5) the compound of the above-shown general formula (I) and its salts, and hydrates and solvates thereof wherein the compound is N-{5-(1-imidazolyl)-2-methoxyphenyl}methyl-N-(1-pentyl)-N'-[2-{3-(4-phenyl-1-piperazyl)propoxy}-6-methylphenyl]urea.

According to another aspect of the present invention, there are provided medicines comprising the compound of the above-shown general formula (I) or a salt thereof or a hydrate or a solvate thereof; and a pharmaceutical composition comprising the compound of the above-shown general formula (I) or a salt thereof or a hydrate or a solvate thereof together with a pharmaceutically acceptable carrier. According to preferred embodiments of the above-defined medicine, there are provided: an antihyperlipidemic agent comprising the compound of the above-shown general formula (I) or a salt thereof or a hydrate or a solvate thereof as an active ingredient; an antiarteriosclerotic agent comprising the compound of the above-shown general formula (I) or a salt thereof or a hydrate or a solvate thereof as an active ingredient; a cholesterol-lowering agent comprising the compound of the above-shown general formula (I) or a salt thereof or a hydrate or a solvate thereof as an active ingredient; and a triglyceride-lowering agent comprising the compound of the above-shown general formula (I) or a salt thereof or a hydrate or a solvate thereof as an active ingredient. According to further aspect of the present invention, uses of the compound of the above-shown general formula (I) or salts thereof or hydrates or solvates thereof for the manufactures of these pharmaceutical compositions are provided.

According to still further embodiments of the present invention, there are provided: a method for preventive and/or therapeutic treatment of hyperlipemia which comprises the step of administering to a patient suffering from hyperlipemia an effective amount of a substance selected from the group consisting of the compound of the above-shown general formula (I) and a salt thereof, and a hydrate and a solvate thereof; a method for preventive and/or therapeutic treatment of arteriosclerosis which comprises the step of administering to a patient suffering from arteriosclerosis an effective amount of a substance selected from the group consisting of the compound of the above-shown general formula (I) and a salt thereof, and a hydrate and a solvate thereof; a method for preventive and/or therapeutic treatment of hypercholesterolemia which comprises the step of administering to a patient suffering from hypercholesterolemia an effective amount of a substance selected from the group consisting of the compound of the above-shown general formula (I) and a salt thereof, and a hydrate and a solvate thereof; and a method for preventive and/or therapeutic treatment of hypertriglyceridemia which comprises the step of administering to a patient suffering from hypertriglyceridemia an effective amount of a substance selected from the group consisting of the compound of the above-shown general formula (I) and a salt thereof, and a hydrate and a solvate thereof.

BEST MODE FOR CARRYING OUT THE INVENTION

In the above formula (I), examples of the $C_1$–$C_3$ alkoxy groups for $R_1$, $R_2$ and $R_3$ include methoxy group, ethoxy group, n-propoxy group, and isopropoxy group. Methoxy group is particularly preferred. Examples of the $C_7$–$C_9$ aralkyloxy group include benzyloxy group, phenethyloxy group, phenylpropyloxy group and the like, and a phenyl-$(C_1$–$C_3)$alkoxy group is preferred and phenylmethyloxy group is more preferred. The heterocyclic group containing from 1 to 4 nitrogen atoms and 5 or 6 ring-membered atoms include, for example, pyrrolyl group, imidazolyl group, pyrazolyl group, pyridyl group, pyrazinyl group, pyrimidinyl group, pyridazinyl group, pyrrolidinyl group, pyrrolinyl group, imidazolydinyl group, imidazolinyl group, pyrazolidinyl group, pyrazolinyl group, piperidyl group, piperazinyl group, triazolidinyl group, triazolyl group, triazinyl group, tetrazolyl group, and tetrazinyl group. Among these groups, pyrrolyl group, imidazolyl group, pyrazolyl group, or triazolyl group are preferred, pyrrolyl group, 1-imidazolyl group, 1-pyrazolyl group, or 1-triazolyl group are more preferred. Most preferred groups are 1-imidazolyl group or 1-triazolyl group. The heterocyclic group defined by "Het" that contains 1 or 2 nitrogen atoms and 5 or 6 ring-membered atoms may be chosen from the aforementioned heterocyclic group that contain one or two nitrogen atoms. Among them, pyridyl group is preferred and 2-pyridyl group and 3-pyridyl group are particularly preferred.

Examples of the $C_1$–$C_7$ alkyl group for $R_4$ include, for example, methyl group, ethyl group, n-propyl group, iso-propyl group, n-butyl group, isobutyl group, t-butyl group, sec-butyl group, n-pentyl group, isopentyl group, sec-pentyl group, neopentyl group, n-hexyl group, isohexyl group, and n-heptyl group. Particularly preferred group are n-propyl group and n-pentyl group. The $C_3$–$C_7$ cycloalkyl group may be cyclopropyl group, cyclobutyl group, cyclopentyl group, cyclohexyl group, cycloheptyl group or the like, and cyclopentyl group is particularly preferred. The $C_6$–$C_{10}$ aryl group defined by "Ar" may be phenyl group, tolyl group, naphthyl group or the like, and phenyl group is particularly preferred.

The $C_1$–$C_3$ alkyl groups for $R_5$ and $R_6$ may be the aforementioned alkyl groups that consist of 1 to 3 carbon atoms, and particularly preferred is methyl group.

The $C_1$–$C_3$ alkyl group for "Y" may be the aforementioned alkyl groups that consist of 1 to 3 carbon atoms, and particularly preferred is methyl group. The heterocyclic group containing 1 to 4 nitrogen atoms and having 5 or 6 ring-membered atoms may be the aforementioned heterocyclic group or the like. Pyridyl group is preferred and 2-pyridyl group is more preferred. The $C_6$–$C_{10}$ aryl group may be the aforementioned aryl groups or the like, and phenyl group is preferred.

According to the present invention, $R_1$ and $R_2$ may form a ring of —O—$(CH_2)_n$—O— together wherein n represents integer of 1 to 3. In that case, n represents preferably 1. Where $R_4$ represents Ar—$(CH_2)_p$— where Ar is the same as that defined above and p represents an integer of 1 to 3, p represents preferably 1 or 3. $R_5$ and $R_6$ may form a ring of —$(CH_2)_q$— wherein q represents an integer of 3 to 5. In that case, q represents preferably 4. In addition, k is preferably 1 or 2, and l is preferably 3. Furthermore, according to the present invention, compounds wherein at least one of $R_1$, $R_2$ and $R_3$ represents Het-$(CH_2)_m$—O— (Het represents 2-pyridyl group or 3-pyridyl group and m represents 1), 1-imidazolyl group, or 1-triazolyl group are preferred particularly.

Preferred embodiments of the compounds of the present invention include:

(1) $R_1$, $R_2$ and $R_3$ represent independently hydrogen atom, hydroxyl group, a $C_1$–$C_3$ alkoxy group, Het-$(CH_2)_m$—O— (Het represents pyridyl group, and m represents an integer of 1 to 3), phenyl-$(C_1$–$C_3)$alkoxy group, pyrrolyl group, imidazolyl group, pyrazolyl group, or triazolyl group, alternatively, $R_1$ and $R_2$ may form a ring of —O—$(CH_2)_n$—O— together to which $R_1$ and $R_2$ are bonded, wherein n represents an integer of 1 to 3;

$R_4$ represents a $C_1$–$C_7$ alkyl group, a $C_3$–$C_7$ cycloalkyl group, or Ar—$(CH_2)_p$— (Ar represents phenyl group, and p represents an integer of from 1 to 3;

$R_5$ and $R_6$ represent independently hydrogen atom or a $C_1$–$C_3$ alkyl group, alternatively, $R_5$ and $R_6$ may form a ring of —$(CH_2)_q$ together with the ring to which $R_5$ and $R_6$ are bound, wherein q represents an integer of 3 to 5;

Y represents a $C_1$–$C_3$ alkyl group, pyridyl group, or phenyl group; and k represents an integer of 1 to 3 and l represents an integer of 2 to 4.

More preferred embodiments of the compounds of the present invention include:

(2) $R_1$, $R_2$ and $R_3$ represent independently hydrogen atom, a $C_1$–$C_3$ alkoxy group, Het-$(CH_2)_m$—O— (Het represents 2-pyridyl group, 3-pyridyl group, or 4-pyridyl group, and m represents 1), phenylmethyloxy group, 1-pyrrolyl group, 1-imidazolyl group, 1-pyrazolyl group, or 1-triazolyl group, alternatively, $R_1$ and $R_2$ may form a ring of —O—$(CH_2)_n$—O— together with the ring to which $R_1$ and $R_2$ bonded, wherein n represents 1;

$R_4$ represents a $C_1$–$C_7$ alkyl group, cyclopentyl group, or Ar—$(CH_2)_p$— (Ar represents phenyl group and p represents 1 or 3);

$R_5$ represents a $C_1$–$C_3$ alkyl group and $R_6$ represents hydrogen atom, alternatively, $R_5$ and $R_6$ may form a ring of —$(CH_2)_q$— together with the ring to which $R_5$ and $R_6$ are bonded, wherein q represents 4;

Y represents 2-pyridyl group or phenyl group; and k represents 1 or 2 and l represents 3.

Particularly preferred embodiments of the compounds of the present invention include:

(3) at least one of $R_1$, $R_2$ and $R_3$ represents Het-$(CH_2)_m$—O— (Het represents 2-pyridyl group or 3-pyridyl group, and m represents 1), 1-imidazolyl group, or 1-triazolyl group;

$R_4$ represents n-propyl group, n-pentyl group, cyclopentyl group, or Ar—$(CH_2)_p$— (Ar represents phenyl group and p represents 1 or 3);

$R_5$ represents methyl group and $R_6$ represents hydrogen atom, alternatively, $R_5$ and $R_6$ may form a ring of —$(CH_2)_q$— together with the ring to which $R_5$ and $R_6$ are bonded, wherein q represents 4;

Y represents phenyl group; and k represents 1 or 2 and l represents 3.

A specific example includes:

(4) N-{5-(1-imidazolyl)-2-methoxyphenyl}methyl-N-(1-pentyl)-N'-[2-{3-(4-phenyl-1-piperazyl)propoxy}-6-methylphenyl]urea and a salt thereof, and a hydrate and a solvate thereof.

The compounds of the present invention represented by the formula (I) may form salts together with inorganic acids such as, for example, hydrochloric acid, hydrobromic acid, sulfuric acid, phosphoric acid, or nitric acid, or organic acids such as, for example, acetic acid, succinic acid, adipic acid, propionic acid, tartaric acid, fumaric acid, maleic acid, oxalic acid, citric acid, benzoic acid, toluenesulfonic acid, or methanesulfonic acid. The compounds of the present invention or salts thereof may form hydrates, or may form solvates together with a solvent such as methanol, ethanol, isopropanol, acetone, ethyl acetate, or methylene chloride. These substances also are included within the compounds of the present invention.

Specific examples of the compounds of the present invention represented by the formula (I) are shown in Table 1 set out below. In the table, as for the phenyl ring attached with $R_1$, $R_2$, and $R_3$, the structures are defined by the name and position of the substituents on the ring provided that the position attached with —$(CH_2)_k$— is regarded as 1-position.

Also in the table, "Ph" represents phenyl and "benzyl" represents benzyl group (—CH$_2$—C$_6$H$_5$). The symbol "2—OCH$_2$O—3" as for the phenyl ring attached with R$_1$, R$_2$, and R$_3$ means that 2,3-methylendioxy group substitutes on the phenyl ring, and the symbol "—(CH$_2$)$_4$—" as for R$_5$ and R$_6$ means that R$_5$ and R$_6$ form a ring of —(CH$_2$)$_4$— together.

In addition, each of definitions such as "—O—CH$_2$-2-Py" or "imidazolyl" represents the substituents specified below.

TABLE 1

| Positions of R$_1$, R$_2$, R$_3$ on the phenyl nucleus | | | | | | | | | |
|---|---|---|---|---|---|---|---|---|---|
| 2- | 3- | 4- | 5- | R$_4$ | R$_5$ | R$_6$ | Y | k | l |
| -imidazolyl | H | H | H | —(CH$_2$)$_2$CH$_3$ | —CH$_3$ | H | —Ph | 1 | 2 |
| -imidazolyl | H | H | H | —CH(CH$_3$)$_2$ | —CH$_3$ | H | —Ph | 1 | 2 |
| -imidazolyl | H | H | H | —(CH$_2$)$_3$CH$_3$ | —CH$_3$ | H | —Ph | 1 | 2 |
| -imidazolyl | H | H | H | —CH$_2$CH(CH$_3$)$_2$ | —CH$_3$ | H | —Ph | 1 | 2 |
| -imidazolyl | H | H | H | —C(CH$_3$)$_3$ | —CH$_3$ | H | —Ph | 1 | 2 |
| -imidazolyl | H | H | H | —(CH$_2$)$_4$CH$_3$ | —CH$_3$ | H | —Ph | 1 | 2 |
| -imidazolyl | H | H | H | —(CH$_2$)$_2$CH(CH$_3$)$_2$ | —CH$_3$ | H | —Ph | 1 | 2 |
| -imidazolyl | H | H | H | —CH$_2$C(CH$_3$)$_3$ | —CH$_3$ | H | —Ph | 1 | 2 |
| -imidazolyl | H | H | H | —(CH$_2$)$_5$CH$_3$ | —CH$_3$ | H | —Ph | 1 | 2 |
| -imidazolyl | H | H | H | —(CH$_2$)$_6$CH$_3$ | —CH$_3$ | H | —Ph | 1 | 2 |
| H | -imidazolyl | H | H | —(CH$_2$)$_2$CH$_3$ | —CH$_3$ | H | —Ph | 1 | 2 |
| H | -imidazolyl | H | H | —CH(CH$_3$)$_2$ | —CH$_3$ | H | —Ph | 1 | 2 |
| H | -imidazolyl | H | H | —(CH$_2$)$_3$CH$_3$ | —CH$_3$ | H | —Ph | 1 | 2 |
| H | -imidazolyl | H | H | —CH$_2$CH(CH$_3$)$_2$ | —CH$_3$ | H | —Ph | 1 | 2 |
| H | -imidazolyl | H | H | —C(CH$_3$)$_3$ | —CH$_3$ | H | —Ph | 1 | 2 |
| H | -imidazolyl | H | H | —(CH$_2$)$_4$CH$_3$ | —CH$_3$ | H | —Ph | 1 | 2 |
| H | -imidazolyl | H | H | —(CH$_2$)$_2$CH(CH$_3$)$_2$ | —CH$_3$ | H | —Ph | 1 | 2 |
| H | -imidazolyl | H | H | —CH$_2$C(CH$_3$)$_3$ | —CH$_3$ | H | —Ph | 1 | 2 |
| H | -imidazolyl | H | H | —(CH$_2$)$_5$CH$_3$ | —CH$_3$ | H | —Ph | 1 | 2 |
| H | -imidazolyl | H | H | —(CH$_2$)$_6$CH$_3$ | —CH$_3$ | H | —Ph | 1 | 2 |
| H | H | -imidazolyl | H | —(CH$_2$)$_2$CH$_3$ | —CH$_3$ | H | —Ph | 1 | 2 |
| H | H | -imidazolyl | H | —CH(CH$_3$)$_2$ | —CH$_3$ | H | —Ph | 1 | 2 |
| H | H | -imidazolyl | H | —(CH$_2$)$_3$CH$_3$ | —CH$_3$ | H | —Ph | 1 | 2 |
| H | H | -imidazolyl | H | —CH$_2$CH(CH$_3$)$_2$ | —CH$_3$ | H | —Ph | 1 | 2 |
| H | H | -imidazolyl | H | —C(CH$_3$)$_3$ | —CH$_3$ | H | —Ph | 1 | 2 |
| H | H | -imidazolyl | H | —(CH$_2$)$_4$CH$_3$ | —CH$_3$ | H | —Ph | 1 | 2 |
| H | H | -imidazolyl | H | —(CH$_2$)$_2$CH(CH$_3$)$_2$ | —CH$_3$ | H | —Ph | 1 | 2 |
| H | H | -imidazolyl | H | —CH$_2$C(CH$_3$)$_3$ | —CH$_3$ | H | —Ph | 1 | 2 |
| H | H | -imidazolyl | H | —(CH$_2$)$_5$CH$_3$ | —CH$_3$ | H | —Ph | 1 | 2 |
| H | H | -imidazolyl | H | —(CH$_2$)$_6$CH$_3$ | —CH$_3$ | H | —Ph | 1 | 2 |
| -imidazolyl | H | H | —OCH$_3$ | —(CH$_2$)$_2$CH$_3$ | —CH$_3$ | H | —Ph | 1 | 2 |
| -imidazolyl | H | H | —OCH$_3$ | —(CH$_2$)$_3$CH$_3$ | —CH$_3$ | H | —Ph | 1 | 2 |
| -imidazolyl | H | H | —OCH$_3$ | —(CH$_2$)$_4$CH$_3$ | —CH$_3$ | H | —Ph | 1 | 2 |
| 2-OCH$_2$O-3 | | H | -imidazolyl | —(CH$_2$)$_2$CH$_3$ | —CH$_3$ | H | —Ph | 1 | 2 |
| 2-OCH$_2$O-3 | | H | -imidazolyl | —(CH$_2$)$_4$CH$_3$ | —CH$_3$ | H | —Ph | 1 | 2 |
| —OCH$_3$ | —OCH$_3$ | H | -imidazolyl | —(CH$_2$)$_2$CH$_3$ | —CH$_3$ | H | —Ph | 1 | 2 |
| —OCH$_3$ | —OCH$_3$ | H | -imidazolyl | —(CH$_2$)$_4$CH$_3$ | —CH$_3$ | H | —Ph | 1 | 2 |
| —OCH$_3$ | H | H | -imidazolyl | —CH$_3$ | —CH$_3$ | H | —Ph | 1 | 2 |
| —OCH$_3$ | H | H | -imidazolyl | —CH$_2$CH$_3$ | —CH$_3$ | H | —Ph | 1 | 2 |
| —OCH$_3$ | H | H | -imidazolyl | —(CH$_2$)$_2$CH$_3$ | —CH$_3$ | H | —Ph | 1 | 2 |
| —OCH$_3$ | H | H | -imidazolyl | —CH(CH$_3$)$_2$ | —CH$_3$ | H | —Ph | 1 | 2 |
| —OCH$_3$ | H | H | -imidazolyl | —(CH$_2$)$_3$CH$_3$ | —CH$_3$ | H | —Ph | 1 | 2 |
| —OCH$_3$ | H | H | -imidazolyl | —CH$_2$CH(CH$_3$)$_3$ | —CH$_3$ | H | —Ph | 1 | 2 |
| —OCH$_3$ | H | H | -imidazolyl | —C(CH$_3$)$_2$ | —CH$_3$ | H | —Ph | 1 | 2 |
| —OCH$_3$ | H | H | -imidazolyl | —(CH$_2$)$_4$CH$_3$ | —CH$_3$ | H | —Ph | 1 | 2 |
| —OCH$_3$ | H | H | -imidazolyl | —(CH$_2$)$_2$CH(CH$_3$)$_2$ | —CH$_3$ | H | —Ph | 1 | 2 |
| —OCH$_3$ | H | H | -imidazolyl | —CH$_2$C(CH$_3$)$_3$ | —CH$_3$ | H | —Ph | 1 | 2 |
| —OCH$_3$ | H | H | -imidazolyl | —(CH$_2$)$_5$CH$_3$ | —CH$_3$ | H | —Ph | 1 | 2 |
| —OCH$_3$ | H | H | -imidazolyl | -benzyl | —CH$_3$ | H | —Ph | 1 | 2 |
| H | —OCH$_3$ | -imidazolyl | H | —CH$_3$ | —CH$_3$ | H | —Ph | 1 | 2 |
| H | —OCH$_3$ | -imidazolyl | H | —CH$_2$CH$_3$ | —CH$_3$ | H | —Ph | 1 | 2 |
| H | —OCH$_3$ | -imidazolyl | H | —(CH$_2$)$_2$CH$_3$ | —CH$_3$ | H | —Ph | 1 | 2 |
| H | —OCH$_3$ | -imidazolyl | H | —CH(CH$_3$)$_2$ | —CH$_3$ | H | —Ph | 1 | 2 |
| H | —OCH$_3$ | -imidazolyl | H | —(CH$_2$)$_3$CH$_3$ | —CH$_3$ | H | —Ph | 1 | 2 |
| H | —OCH$_3$ | -imidazolyl | H | —CH$_2$CH(CH$_3$)$_2$ | —CH$_3$ | H | —Ph | 1 | 2 |
| H | —OCH$_3$ | -imidazolyl | H | —C(CH$_3$)$_3$ | —CH$_3$ | H | —Ph | 1 | 2 |
| H | —OCH$_3$ | -imidazolyl | H | —(CH$_2$)$_4$CH$_3$ | —CH$_3$ | H | —Ph | 1 | 2 |
| H | —OCH$_3$ | -imidazolyl | H | —(CH$_2$)$_2$CH(CH$_3$)$_2$ | —CH$_3$ | H | —Ph | 1 | 2 |
| H | —OCH$_3$ | -imidazolyl | H | —CH$_2$C(CH$_3$)$_3$ | —CH$_3$ | H | —Ph | 1 | 2 |
| H | —OCH$_3$ | -imidazolyl | H | —(CH$_2$)$_5$CH$_3$ | —CH$_3$ | H | —Ph | 1 | 2 |
| H | —OCH$_3$ | -imidazolyl | H | -benzyl | —CH$_3$ | H | —Ph | 1 | 2 |
| H | -imidazolyl | —OCH$_3$ | H | —CH$_3$ | —CH$_3$ | H | —Ph | 1 | 2 |
| H | -imidazolyl | —OCH$_3$ | H | —CH$_2$CH$_3$ | —CH$_3$ | H | —Ph | 1 | 2 |
| H | -imidazolyl | —OCH$_3$ | H | —(CH$_2$)$_2$CH$_3$ | —CH$_3$ | H | —Ph | 1 | 2 |
| H | -imidazolyl | —OCH$_3$ | H | —CH(CH$_3$)$_2$ | —CH$_3$ | H | —Ph | 1 | 2 |
| H | -imidazolyl | —OCH$_3$ | H | —(CH$_2$)$_3$CH$_3$ | —CH$_3$ | H | —Ph | 1 | 2 |
| H | -imidazolyl | —OCH$_3$ | H | —CH$_2$CH(CH$_3$)$_2$ | —CH$_3$ | H | —Ph | 1 | 2 |
| H | -imidazolyl | —OCH$_3$ | H | —C(CH$_3$)$_3$ | —CH$_3$ | H | —Ph | 1 | 2 |
| H | -imidazolyl | —OCH$_3$ | H | —(CH$_2$)$_4$CH$_3$ | —CH$_3$ | H | —Ph | 1 | 2 |

TABLE 1-continued

| Positions of $R_1$, $R_2$, $R_3$ on the phenyl nucleus | | | | | | | | | |
|---|---|---|---|---|---|---|---|---|---|
| 2- | 3- | 4- | 5- | $R_4$ | $R_5$ | $R_6$ | Y | k | l |
| H | -imidazolyl | —$OCH_3$ | H | —$(CH_2)_2CH(CH_3)_2$ | —$CH_3$ | H | —Ph | 1 | 2 |
| H | -imidazolyl | —$OCH_3$ | H | —$CH_2C(CH_3)_3$ | —$CH_3$ | H | —Ph | 1 | 2 |
| H | -imidazolyl | —$OCH_3$ | H | —$(CH_2)_5CH_3$ | —$CH_3$ | H | —Ph | 1 | 2 |
| H | -imidazolyl | —$OCH_3$ | H | -benzyl | —$CH_3$ | H | —Ph | 1 | 2 |
| -imidazolyl | H | H | H | —$(CH_2)_2CH_3$ | —$CH_3$ | H | —Ph | 1 | 3 |
| -imidazolyl | H | H | H | —$CH(CH_3)_2$ | —$CH_3$ | H | —Ph | 1 | 3 |
| -imidazolyl | H | H | H | —$(CH_2)_3CH_3$ | —$CH_3$ | H | —Ph | 1 | 3 |
| -imidazolyl | H | H | H | —$CH_2CH(CH_3)_2$ | —$CH_3$ | H | —Ph | 1 | 3 |
| -imidazolyl | H | H | H | —$C(CH_3)_3$ | —$CH_3$ | H | —Ph | 1 | 3 |
| -imidazolyl | H | H | H | —$(CH_2)_4CH_3$ | —$CH_3$ | H | —Ph | 1 | 3 |
| -imidazolyl | H | H | H | —$(CH_2)_2CH(CH_3)_2$ | —$CH_3$ | H | —Ph | 1 | 3 |
| -imidazolyl | H | H | H | —$CH_2C(CH_3)_3$ | —$CH_3$ | H | —Ph | 1 | 3 |
| -imidazolyl | H | H | H | —$(CH_2)_5CH_3$ | —$CH_3$ | H | —Ph | 1 | 3 |
| -imidazolyl | H | H | H | —$(CH_2)_6CH_3$ | —$CH_3$ | H | —Ph | 1 | 3 |
| H | -imidazolyl | H | H | —$(CH_2)_2CH_3$ | —$CH_3$ | H | —Ph | 1 | 3 |
| H | -imidazolyl | H | H | —$CH(CH_3)_2$ | —$CH_3$ | H | —Ph | 1 | 3 |
| H | -imidazolyl | H | H | —$(CH_2)_3CH_3$ | —$CH_3$ | H | —Ph | 1 | 3 |
| H | -imidazolyl | H | H | —$CH_2CH(CH_3)_3$ | —$CH_3$ | H | —Ph | 1 | 3 |
| H | -imidazolyl | H | H | —$C(CH_3)_3$ | —$CH_3$ | H | —Ph | 1 | 3 |
| H | -imidazolyl | H | H | —$(CH_2)_4CH_3$ | —$CH_3$ | H | —Ph | 1 | 3 |
| H | -imidazolyl | H | H | —$(CH_2)_2CH(CH_3)_2$ | —$CH_3$ | H | —Ph | 1 | 3 |
| H | -imidazolyl | H | H | —$CH_2C(CH_3)_3$ | —$CH_3$ | H | —Ph | 1 | 3 |
| H | -imidazolyl | H | H | —$(CH_3)_5CH_3$ | —$CH_3$ | H | —Ph | 1 | 3 |
| H | -imidazolyl | H | H | —$(CH_2)_6CH_3$ | —$CH_3$ | H | —Ph | 1 | 3 |
| H | H | -imidazolyl | H | —$(CH_2)_2CH_3$ | —$CH_3$ | H | —Ph | 1 | 3 |
| H | H | -imidazolyl | H | —$CH(CH_3)_2$ | —$CH_3$ | H | —Ph | 1 | 3 |
| H | H | -imidazolyl | H | —$(CH_2)_3CH_3$ | —$CH_3$ | H | —Ph | 1 | 3 |
| H | H | -imidazolyl | H | —$CH_2CH(CH_3)_2$ | —$CH_3$ | H | —Ph | 1 | 3 |
| H | H | -imidazolyl | H | —$C(CH_3)_3$ | —$CH_3$ | H | —Ph | 1 | 3 |
| H | H | -imidazolyl | H | —$(CH_2)_4CH_3$ | —$CH_3$ | H | —Ph | 1 | 3 |
| H | H | -imidazolyl | H | —$(CH_2)_2CH(CH_3)_2$ | —$CH_3$ | H | —Ph | 1 | 3 |
| H | H | -imidazolyl | H | —$CH_2C(CH_3)_3$ | —$CH_3$ | H | —Ph | 1 | 3 |
| H | H | -imidazolyl | H | —$(CH_2)_5CH_3$ | —$CH_3$ | H | —Ph | 1 | 3 |
| H | H | -imidazolyl | H | —$(CH_2)_6CH_3$ | —$CH_3$ | H | —Ph | 1 | 3 |
| H | —$OCH_3$ | -imidazolyl | H | —$CH_3$ | —$CH_3$ | H | —Ph | 1 | 3 |
| H | —$OCH_3$ | -imidazolyl | H | —$CH_2CH_3$ | —$CH_3$ | H | —Ph | 1 | 3 |
| H | —$OCH_3$ | -imidazolyl | H | —$(CH_2)_2CH_3$ | —$CH_3$ | H | —Ph | 1 | 3 |
| H | —$OCH_3$ | -imidazolyl | H | —$CH(CH_3)_2$ | —$CH_3$ | H | —Ph | 1 | 3 |
| H | —$OCH_3$ | -imidazolyl | H | —$(CH_2)_3CH_3$ | —$CH_3$ | H | —Ph | 1 | 3 |
| H | —$OCH_3$ | -imidazolyl | H | —$CH_2CH(CH_3)_2$ | —$CH_3$ | H | —Ph | 1 | 3 |
| H | —$OCH_3$ | -imidazolyl | H | —$C(CH_3)_3$ | —$CH_3$ | H | —Ph | 1 | 3 |
| H | —$OCH_3$ | -imidazolyl | H | —$(CH_2)_4CH_3$ | —$CH_3$ | H | —Ph | 1 | 3 |
| H | —$OCH_3$ | -imidazolyl | H | —$(CH_2)_2CH(CH_3)_2$ | —$CH_3$ | H | —Ph | 1 | 3 |
| H | —$OCH_3$ | -imidazolyl | H | —$CH_2C(CH_3)_3$ | —$CH_3$ | H | —Ph | 1 | 3 |
| H | —$OCH_3$ | -imidazolyl | H | —$(CH_2)_5CH_3$ | —$CH_3$ | H | —Ph | 1 | 3 |
| H | —$OCH_3$ | -imidazolyl | H | -benzyl | —$CH_3$ | H | —Ph | i | 3 |
| -imidazolyl | H | H | —$OCH_3$ | —$(CH_2)_2CH_3$ | —$CH_3$ | H | —Ph | 1 | 3 |
| -imidazolyl | H | H | —$OCH_3$ | —$(CH_2)_3CH_3$ | —$CH_3$ | H | —Ph | 1 | 3 |
| -imidazolyl | H | H | —$OCH_3$ | —$(CH_2)_4CH_3$ | —$CH_3$ | H | —Ph | 1 | 3 |
| | 2-$OCH_2O$-3 | H | -imidazolyl | —$(CH_2)_2CH_3$ | —$CH_3$ | H | —Ph | 1 | 3 |
| | 2-$OCH_2O$-3 | H | -imidazolyl | —$(CH_2)_4CH_3$ | —$CH_3$ | H | —Ph | 1 | 3 |
| —$OCH_3$ | —$OCH_3$ | H | -imidazolyl | —$(CH_2)_2CH_3$ | —$CH_3$ | H | —Ph | 1 | 3 |
| —$OCH_3$ | —$OCH_3$ | H | -imidazolyl | —$(CH_2)_4CH_3$ | —$CH_3$ | H | —Ph | 1 | 3 |
| —$OCH_3$ | H | H | -imidazolyl | —$CH_3$ | —$CH_3$ | H | —Ph | 1 | 3 |
| —$OCH_3$ | H | H | -imidazolyl | —$CH_2CH_3$ | —$CH_3$ | H | —Ph | 1 | 3 |
| —$OCH_3$ | H | H | -imidazolyl | —$(CH_2)_2CH_3$ | —$CH_3$ | H | —Ph | 1 | 3 |
| —$OCH_3$ | H | H | -imidazolyl | —$CH(CH_3)_3$ | —$CH_3$ | H | —Ph | 1 | 3 |
| —$OCH_3$ | H | H | -imidazolyl | —$(CH_2)_3CH_2$ | —$CH_3$ | H | —Ph | 1 | 3 |
| —$OCH_3$ | H | H | -imidazolyl | —$CH_2CH(CH_3)_2$ | —$CH_3$ | H | —Ph | 1 | 3 |
| —$OCH_3$ | H | H | -imidazolyl | —$C(CH_3)_3$ | —$CH_3$ | H | —Ph | 1 | 3 |
| —$OCH_3$ | H | H | -imidazolyl | —$(CH_2)_4CH_3$ | —$CH_3$ | H | —Ph | 1 | 3 |
| —$OCH_3$ | H | H | -imidazolyl | —$(CH_2)_2CH(CH_3)_2$ | —$CH_3$ | H | —Ph | 1 | 3 |
| —$OCH_3$ | H | H | -imidazolyl | —$CH_2C(CH_3)_3$ | —$CH_3$ | H | —Ph | 1 | 3 |
| —$OCH_3$ | H | H | -imidazolyl | —$(CH_2)_5CH_3$ | —$CH_3$ | H | —Ph | 1 | 3 |
| —$OCH_3$ | H | H | -imidazolyl | -benzyl | —$CH_3$ | H | —Ph | 1 | 3 |
| H | -imidazolyl | —$OCH_3$ | H | —$CH_3$ | —$CH_3$ | H | —Ph | 1 | 3 |
| H | -imidazolyl | —$OCH_3$ | H | —$CH_2CH_3$ | —$CH_3$ | H | —Ph | 1 | 3 |
| H | -imidazolyl | —$OCH_3$ | H | —$(CH_2)_2CH_3$ | —$CH_3$ | H | —Ph | 1 | 3 |
| H | -imidazolyl | —$OCH_3$ | H | —$CH(CH_3)_2$ | —$CH_3$ | H | —Ph | 1 | 3 |
| H | -imidazolyl | —$OCH_3$ | H | —$(CH_2)_3CH_3$ | —$CH_3$ | H | —Ph | 1 | 3 |
| H | -imidazolyl | —$OCH_3$ | H | —$CH_2CH(CH_3)_2$ | —$CH_3$ | H | —Ph | 1 | 3 |
| H | -imidazolyl | —$OCH_3$ | H | —$C(CH_3)_3$ | —$CH_3$ | H | —Ph | 1 | 3 |
| H | -imidazolyl | —$OCH_3$ | H | —$(CH_2)_4CH_3$ | —$CH_3$ | H | —Ph | 1 | 3 |
| H | -imidazolyl | —$OCH_3$ | H | —$(CH_2)_2CH(CH_3)_2$ | —$CH_3$ | H | —Ph | 1 | 3 |
| H | -imidazolyl | —$OCH_3$ | H | —$CH_2C(CH_3)_3$ | —$CH_3$ | H | —Ph | 1 | 3 |

TABLE 1-continued

| Positions of $R_1$, $R_2$, $R_3$ on the phenyl nucleus | | | | | | | | | |
|---|---|---|---|---|---|---|---|---|---|
| 2- | 3- | 4- | 5- | $R_4$ | $R_5$ | $R_6$ | Y | k | l |
| H | -imidazolyl | —OCH$_3$ | H | —(CH$_2$)$_5$CH$_3$ | —CH$_3$ | H | —Ph | 1 | 3 |
| H | -imidazolyl | —OCH$_3$ | H | -benzyl | —CH$_3$ | H | —Ph | 1 | 3 |
| -imidazolyl | H | H | H | —(CH$_2$)$_2$CH$_3$ | —CH$_3$ | H | —Ph | 2 | 3 |
| -imidazolyl | H | H | H | —(CH$_2$)$_3$CH$_3$ | —CH$_3$ | H | —Ph | 2 | 3 |
| -imidazolyl | H | H | H | —(CH$_2$)$_4$CH$_3$ | —CH$_3$ | H | —Ph | 2 | 3 |
| H | -imidazolyl | H | H | —(CH$_2$)$_2$CH$_3$ | —CH$_3$ | H | —Ph | 2 | 3 |
| H | -imidazolyl | H | H | —(CH$_2$)$_3$CH$_3$ | —CH$_3$ | H | —Ph | 2 | 3 |
| H | -imidazolyl | H | H | —(CH$_2$)$_4$CH$_3$ | —CH$_3$ | H | —Ph | 2 | 3 |
| H | H | -imidazolyl | H | —(CH$_2$)$_2$CH$_3$ | —CH$_3$ | H | —Ph | 2 | 3 |
| H | H | -imidazolyl | H | —(CH$_2$)$_3$CH$_3$ | —CH$_3$ | H | —Ph | 2 | 3 |
| H | H | -imidazolyl | H | —(CH$_2$)$_4$CH$_3$ | —CH$_3$ | H | —Ph | 2 | 3 |
| -imidazolyl | H | H | H | —(CH$_2$)$_2$CH$_3$ | —CH$_3$ | H | —Ph | 2 | 2 |
| -imidazolyl | H | H | H | —(CH$_2$)$_3$CH$_3$ | —CH$_3$ | H | —Ph | 2 | 2 |
| -imidazolyl | H | H | H | —(CH$_2$)$_4$CH$_3$ | —CH$_3$ | H | —Ph | 2 | 2 |
| H | -imidazolyl | H | H | —(CH$_2$)$_2$CH$_3$ | —CH$_3$ | H | —Ph | 2 | 2 |
| H | -imidazolyl | H | H | —(CH$_2$)$_3$CH$_3$ | —CH$_3$ | H | —Ph | 2 | 2 |
| H | -imidazolyl | H | H | —(CH$_2$)$_4$CH$_3$ | —CH$_3$ | H | —Ph | 2 | 2 |
| H | H | -imidazolyl | H | —(CH$_2$)$_2$CH$_3$ | —CH$_3$ | H | —Ph | 2 | 2 |
| H | H | -imidazolyl | H | —(CH$_2$)$_3$CH$_3$ | —CH$_3$ | H | —Ph | 2 | 2 |
| H | H | -imidazolyl | H | —(CH$_2$)$_4$CH$_3$ | —CH$_3$ | H | —Ph | 2 | 2 |
| H | —OCH$_3$ | -imidazolyl | H | —(CH$_2$)$_2$CH$_3$ | —CH$_3$ | H | —Ph | 2 | 2 |
| H | —OCH$_3$ | -imidazolyl | H | —(CH$_2$)$_3$CH$_3$ | —CH$_3$ | H | —Ph | 2 | 2 |
| H | —OCH$_3$ | -imidazolyl | H | —(CH$_2$)$_4$CH$_3$ | —CH$_3$ | H | —Ph | 2 | 2 |
| H | —OCH$_3$ | -imidazolyl | H | —(CH$_2$)$_2$CH$_3$ | —CH$_3$ | H | —Ph | 2 | 3 |
| H | —OCH$_3$ | -imidazolyl | H | —(CH$_2$)$_3$CH$_3$ | —CH$_3$ | H | —Ph | 2 | 3 |
| H | —OCH$_3$ | -imidazolyl | H | —(CH$_2$)$_4$CH$_3$ | —CH$_3$ | H | —Ph | 2 | 3 |
| -imidazolyl | H | H | —OCH$_3$ | —(CH$_2$)$_2$CH$_3$ | —CH$_3$ | H | —Ph | 2 | 2 |
| -imidazolyl | H | H | —OCH$_3$ | —(CH$_2$)$_3$CH$_3$ | —CH$_3$ | H | —Ph | 2 | 2 |
| -imidazolyl | H | H | —OCH$_3$ | —(CH$_2$)$_4$CH$_3$ | —CH$_3$ | H | —Ph | 2 | 2 |
| -imidazolyl | H | H | —OCH$_3$ | —(CH$_2$)$_2$CH$_3$ | —CH$_3$ | H | —Ph | 2 | 3 |
| -imidazolyl | H | H | —OCH$_3$ | —(CH$_2$)$_3$CH$_3$ | —CH$_3$ | H | —Ph | 2 | 3 |
| -imidazolyl | H | H | —OCH$_3$ | —(CH$_2$)$_4$CH$_3$ | —CH$_3$ | H | —Ph | 2 | 3 |
| | 2-OCH$_2$O-3 | | H | -imidazolyl | —(CH$_2$)$_2$CH$_3$ | —CH$_3$ | H | —Ph | 2 | 2 |
| | 2-OCH$_2$O-3 | | H | -imidazolyl | —(CH$_2$)$_4$CH$_3$ | —CH$_3$ | H | —Ph | 2 | 2 |
| | 2-OCH$_2$O-3 | | H | -imidazolyl | —(CH$_2$)$_2$CH$_3$ | —CH$_3$ | H | —Ph | 2 | 3 |
| | 2-OCH$_2$O-3 | | H | -imidazolyl | —(CH$_2$)$_4$CH$_3$ | —CH$_3$ | H | —Ph | 2 | 3 |
| —OCH$_3$ | —OCH$_3$ | H | -imidazolyl | —(CH$_2$)$_2$CH$_3$ | —CH$_3$ | H | —Ph | 2 | 2 |
| —OCH$_3$ | —OCH$_3$ | H | -imidazolyl | —(CH$_2$)$_4$CH$_3$ | —CH$_3$ | H | —Ph | 2 | 2 |
| —OCH$_3$ | —OCH$_3$ | H | -imidazolyl | —(CH$_2$)$_2$CH$_3$ | —CH$_3$ | H | —Ph | 2 | 3 |
| —OCH$_3$ | —OCH$_3$ | H | -imidazolyl | —(CH$_2$)$_4$CH$_3$ | —CH$_3$ | H | —Ph | 2 | 3 |
| —OCH$_3$ | H | H | -imidazolyl | —(CH$_2$)$_2$CH$_3$ | —CH$_3$ | H | —Ph | 2 | 2 |
| —OCH$_3$ | H | H | -imidazolyl | —(CH$_2$)$_3$CH$_3$ | —CH$_3$ | H | —Ph | 2 | 2 |
| —OCH$_3$ | H | H | -imidazolyl | —(CH$_2$)$_4$CH$_3$ | —CH$_3$ | H | —Ph | 2 | 2 |
| —OCH$_3$ | H | H | -imidazolyl | —(CH$_2$)$_2$CH$_3$ | —CH$_3$ | H | —Ph | 2 | 3 |
| —OCH$_3$ | H | H | -imidazolyl | —(CH$_2$)$_3$CH$_3$ | —CH$_3$ | H | —Ph | 2 | 3 |
| —OCH$_3$ | H | H | -imidazolyl | —(CH$_2$)$_4$CH$_3$ | —CH$_3$ | H | —Ph | 2 | 3 |
| H | -imidazolyl | —OCH$_3$ | H | —(CH$_2$)$_2$CH$_3$ | —CH$_3$ | H | —Ph | 2 | 2 |
| H | -imidazolyl | —OCH$_3$ | H | —(CH$_2$)$_3$CH$_3$ | —CH$_3$ | H | —Ph | 2 | 2 |
| H | -imidazolyl | —OCH$_3$ | H | —(CH$_2$)$_4$CH$_3$ | —CH$_3$ | H | —Ph | 2 | 2 |
| H | -imidazolyl | —OCH$_3$ | H | —(CH$_2$)$_2$CH$_3$ | —CH$_3$ | H | —Ph | 2 | 3 |
| H | -imidazolyl | —OCH$_3$ | H | —(CH$_2$)$_3$CH$_3$ | —CH$_3$ | H | —Ph | 2 | 3 |
| H | -imidazolyl | —OCH$_3$ | H | —(CH$_2$)$_4$CH$_3$ | —CH$_3$ | H | —Ph | 2 | 3 |
| -imidazolyl | H | H | H | -cyclobutyl | —CH$_3$ | H | —Ph | 1 | 2 |
| -imidazolyl | H | H | H | -cyclopentyl | —CH$_3$ | H | —Ph | 1 | 2 |
| -imidazolyl | H | H | H | -cyclohexyl | —CH$_3$ | H | —Ph | 1 | 2 |
| H | -imidazolyl | H | H | -cyclobutyl | —CH$_3$ | H | —Ph | 1 | 3 |
| H | -imidazolyl | H | H | -cyclopentyl | —CH$_3$ | H | —Ph | 1 | 3 |
| H | -imidazolyl | H | H | -cyclohexyl | —CH$_3$ | H | —Ph | 1 | 3 |
| H | H | -imidazolyl | H | -cyclobutyl | —CH$_3$ | H | —Ph | 1 | 2 |
| H | H | -imidazolyl | H | -cyclopentyl | —CH$_3$ | H | —Ph | 1 | 2 |
| H | H | -imidazolyl | H | -cyclohexyl | —CH$_3$ | H | —Ph | 1 | 2 |
| H | H | -imidazolyl | H | -cyclobutyl | —CH$_3$ | H | —Ph | 1 | 3 |
| H | H | -imidazolyl | H | -cyclopentyl | —CH$_3$ | H | —Ph | 1 | 3 |
| H | H | -imidazolyl | H | -cyclohexyl | —CH$_3$ | H | —Ph | 1 | 3 |
| —OCH$_3$ | H | H | -imidazolyl | -cyclobutyl | —CH$_3$ | H | —Ph | 1 | 2 |
| —OCH$_3$ | H | H | -imidazolyl | -cyclopentyl | —CH$_3$ | H | —Ph | 1 | 2 |
| —OCH$_3$ | H | H | -imidazolyl | -cyclohexyl | —CH$_3$ | H | —Ph | 1 | 2 |
| —OCH$_3$ | H | H | -imidazolyl | -cyclobutyl | —CH$_3$ | H | —Ph | 1 | 3 |
| —OCH$_3$ | H | H | -imidazolyl | -cyclopentyl | —CH$_3$ | H | —Ph | 1 | 3 |
| —OCH$_3$ | H | H | -imidazolyl | -cyclohexyl | —CH$_3$ | H | —Ph | 1 | 3 |
| —OCH$_3$ | —OCH$_3$ | H | -imidazolyl | -cyclobutyl | —CH$_3$ | H | —Ph | 1 | 2 |
| —OCH$_3$ | —OCH$_3$ | H | -imidazolyl | -cyclopentyl | —CH$_3$ | H | —Ph | 1 | 2 |
| —OCH$_3$ | —OCH$_3$ | H | -imidazolyl | -cyclohexyl | —CH$_3$ | H | —Ph | 1 | 2 |
| —OCH$_3$ | —OCH$_3$ | H | -imidazolyl | -cyclobutyl | —CH$_3$ | H | —Ph | 1 | 3 |
| —OCH$_3$ | —OCH$_3$ | H | -imidazolyl | -cyclopentyl | —CH$_3$ | H | —Ph | 1 | 3 |

TABLE 1-continued

| Positions of $R_1$, $R_2$, $R_3$ on the phenyl nucleus | | | | | | | | | | |
|---|---|---|---|---|---|---|---|---|---|---|
| 2- | 3- | 4- | 5- | $R_4$ | | $R_5$ | $R_6$ | Y | k | l |
| —OCH$_3$ | —OCH$_3$ | H | H | -imidazolyl | -cyclohexyl | —CH$_3$ | H | —Ph | 1 | 3 |
| | 2-OCH$_2$O-3 | | H | -imidazolyl | -cyclobutyl | —CH$_3$ | H | —Ph | 1 | 2 |
| | 2-OCH$_2$O-3 | | H | -imidazolyl | -cyclopentyl | —CH$_3$ | H | —Ph | 1 | 2 |
| | 2-OCH$_2$O-3 | | H | -imidazolyl | -cyclohexyl | —CH$_3$ | H | —Ph | 1 | 2 |
| | 2-OCH$_2$O-3 | | H | -imidazolyl | -cyclobutyl | —CH$_3$ | H | —Ph | 1 | 3 |
| | 2-OCH$_2$O-3 | | H | -imidazolyl | -cyclopentyl | —CH$_3$ | H | —Ph | 1 | 3 |
| | 2-OCH$_2$O-3 | | H | -imidazolyl | -cyclohexyl | —CH$_3$ | H | —Ph | 1 | 3 |
| H | —OCH$_3$ | -imidazolyl | H | -cyclobutyl | | —CH$_3$ | H | —Ph | 1 | 2 |
| H | —OCH$_3$ | -imidazolyl | H | -cyclopentyl | | —CH$_3$ | H | —Ph | 1 | 2 |
| H | —OCH$_3$ | -imidazolyl | H | -cyclohexyl | | —CH$_3$ | H | —Ph | 1 | 2 |
| H | —OCH$_3$ | -imidazolyl | H | -cyclobutyl | | —CH$_3$ | H | —Ph | 1 | 3 |
| H | —OCH$_3$ | -imidazolyl | H | -cyclopentyl | | —CH$_3$ | H | —Ph | 1 | 3 |
| H | —OCH$_3$ | -imidazolyl | H | -cyclohexyl | | —CH$_3$ | H | —Ph | 1 | 3 |
| -imidazolyl | H | H | H | -cyclobutyl | | —CH$_3$ | H | —Ph | 2 | 2 |
| -imidazolyl | H | H | H | -cyclopentyl | | —CH$_3$ | H | —Ph | 2 | 2 |
| -imidazolyl | H | H | H | -cyclohexyl | | —CH$_3$ | H | —Ph | 2 | 2 |
| H | -imidazolyl | H | H | -cyclobutyl | | —CH$_3$ | H | —Ph | 2 | 3 |
| H | -imidazolyl | H | H | -cyclopentyl | | —CH$_3$ | H | —Ph | 2 | 3 |
| H | -imidazolyl | H | H | -cyclohexyl | | —CH$_3$ | H | —Ph | 2 | 3 |
| H | H | -imidazolyl | H | -cyclobutyl | | —CH$_3$ | H | —Ph | 2 | 2 |
| H | H | -imidazolyl | H | -cyclopentyl | | —CH$_3$ | H | —Ph | 2 | 2 |
| H | H | -imidazolyl | H | -cyclohexyl | | —CH$_3$ | H | —Ph | 2 | 2 |
| H | H | -imidazolyl | H | -cyclobutyl | | —CH$_3$ | H | —Ph | 2 | 3 |
| H | H | -imidazolyl | H | -cyclopentyl | | —CH$_3$ | H | —Ph | 2 | 3 |
| H | H | -imidazolyl | H | -cyclohexyl | | —CH$_3$ | H | —Ph | 2 | 3 |
| H | -imidazolyl | —OCH$_3$ | H | -cyclobutyl | | —CH$_3$ | H | —Ph | 1 | 2 |
| H | -imidazolyl | —OCH$_3$ | H | -cyclopentyl | | —CH$_3$ | H | —Ph | 1 | 2 |
| H | -imidazolyl | —OCH$_3$ | H | -cyclohexyl | | —CH$_3$ | H | —Ph | 1 | 2 |
| H | -imidazolyl | —OCH$_3$ | H | -cyclobutyl | | —CH$_3$ | H | —Ph | 1 | 3 |
| H | -imidazolyl | —OCH$_3$ | H | -cyclopentyl | | —CH$_3$ | H | —Ph | 1 | 3 |
| H | -imidazolyl | —OCH$_3$ | H | -cyclohexyl | | —CH$_3$ | H | —Ph | 1 | 3 |
| —OCH$_3$ | H | H | -imidazolyl | -cyclobutyl | | —CH$_3$ | H | —Ph | 2 | 2 |
| —OCH$_3$ | H | H | -imidazolyl | -cyclopentyl | | —CH$_3$ | H | —Ph | 2 | 2 |
| —OCH$_3$ | H | H | -imidazolyl | -cyclohexyl | | —CH$_3$ | H | —Ph | 2 | 2 |
| —OCH$_3$ | H | H | -imidazolyl | -cyclobutyl | | —CH$_3$ | H | —Ph | 2 | 3 |
| —OCH$_3$ | H | H | -imidazolyl | -cyclopentyl | | —CH$_3$ | H | —Ph | 2 | 3 |
| —OCH$_3$ | H | H | -imidazolyl | -cyclohexyl | | —CH$_3$ | H | —Ph | 2 | 3 |
| —OCH$_3$ | —OCH$_3$ | H | -imidazolyl | -cyclobutyl | | —CH$_3$ | H | —Ph | 2 | 2 |
| —OCH$_3$ | —OCH$_3$ | H | -imidazolyl | -cyclopentyl | | —CH$_3$ | H | —Ph | 2 | 2 |
| —OCH$_3$ | —OCH$_3$ | H | -imidazolyl | -cyclohexyl | | —CH$_3$ | H | —Ph | 2 | 2 |
| —OCH$_3$ | —OCH$_3$ | H | -imidazolyl | -cyclobutyl | | —CH$_3$ | H | —Ph | 2 | 3 |
| —OCH$_3$ | —OCH$_3$ | H | -imidazolyl | -cyclopentyl | | —CH$_3$ | H | —Ph | 2 | 3 |
| —OCH$_3$ | —OCH$_3$ | H | -imidazolyl | -cyclohexyl | | —CH$_3$ | H | —Ph | 2 | 3 |
| | 2-OCH$_2$O-3 | | H | -imidazolyl | -cyclobutyl | —CH$_3$ | H | —Ph | 2 | 2 |
| | 2-OCH$_2$O-3 | | H | -imidazolyl | -cyclopentyl | —CH$_3$ | H | —Ph | 2 | 2 |
| | 2-OCH$_2$O-3 | | H | -imidazolyl | -cyclohexyl | —CH$_3$ | H | —Ph | 2 | 2 |
| | 2-OCH$_2$O-3 | | H | -imidazolyl | -cyclobutyl | —CH$_3$ | H | —Ph | 2 | 3 |
| | 2-OCH$_2$O-3 | | H | -imidazolyl | -cyclopentyl | —CH$_3$ | H | —Ph | 2 | 3 |
| | 2-OCH$_2$O-3 | | H | -imidazolyl | -cyclohexyl | —CH$_3$ | H | —Ph | 2 | 3 |
| H | —OCH$_3$ | -imidazolyl | H | -cyclobutyl | | —CH$_3$ | H | —Ph | 2 | 2 |
| H | —OCH$_3$ | -imidazolyl | H | -cyclopentyl | | —CH$_3$ | H | —Ph | 2 | 2 |
| H | —OCH$_3$ | -imidazolyl | H | -cyclohexyl | | —CH$_3$ | H | —Ph | 2 | 2 |
| H | —OCH$_3$ | -imidazolyl | H | -cyclobutyl | | —CH$_3$ | H | —Ph | 2 | 3 |
| H | —OCH$_3$ | -imidazolyl | H | -cyclopentyl | | —CH$_3$ | H | —Ph | 2 | 3 |
| H | —OCH$_3$ | -imidazolyl | H | -cyclohexyl | | —CH$_3$ | H | —Ph | 2 | 3 |
| H | -imidazolyl | —OCH$_3$ | H | -cyclobutyl | | —CH$_3$ | H | —Ph | 2 | 2 |
| H | -imidazolyl | —OCH$_3$ | H | -cyclopentyl | | —CH$_3$ | H | —Ph | 2 | 2 |
| H | -imidazolyl | —OCH$_3$ | H | -cyclohexyl | | —CH$_3$ | H | —Ph | 2 | 2 |
| H | -imidazolyl | —OCH$_3$ | H | -cyclobutyl | | —CH$_3$ | H | —Ph | 2 | 3 |
| H | -imidazolyl | —OCH$_3$ | H | -cyclopentyl | | —CH$_3$ | H | —Ph | 2 | 3 |
| H | -imidazolyl | —OCH$_3$ | H | -cyclohexyl | | —CH$_3$ | H | —Ph | 2 | 3 |
| -pyrazolyl | H | H | H | —(CH$_2$)$_2$CH$_3$ | | —CH$_3$ | H | —Ph | 1 | 2 |
| -pyrazolyl | H | H | H | —(CH$_2$)$_3$CH$_3$ | | —CH$_3$ | H | —Ph | 1 | 2 |
| -pyrazolyl | H | H | H | —(CH$_2$)$_4$CH$_3$ | | —CH$_3$ | H | —Ph | 1 | 2 |
| H | -pyrazolyl | H | H | —(CH$_2$)$_2$CH$_3$ | | —CH$_3$ | H | —Ph | 1 | 2 |
| H | -pyrazolyl | H | H | —(CH$_2$)$_3$CH$_3$ | | —CH$_3$ | H | —Ph | 1 | 2 |
| H | -pyrazolyl | H | H | —(CH$_2$)$_4$CH$_3$ | | —CH$_3$ | H | —Ph | 1 | 2 |
| H | H | -pyrazolyl | H | —(CH$_2$)$_2$CH$_3$ | | —CH$_3$ | H | —Ph | 1 | 2 |
| H | H | -pyrazolyl | H | —(CH$_2$)$_3$CH$_3$ | | —CH$_3$ | H | —Ph | 1 | 2 |
| H | H | -pyrazolyl | H | —(CH$_2$)$_4$CH$_3$ | | —CH$_3$ | H | —Ph | 1 | 2 |
| -pyrazolyl | H | H | H | —(CH$_2$)$_2$CH$_3$ | | —CH$_3$ | H | —Ph | 1 | 3 |
| -pyrazolyl | H | H | H | —(CH$_2$)$_3$CH$_3$ | | —CH$_3$ | H | —Ph | 1 | 3 |
| -pyrazolyl | H | H | H | —(CH$_2$)$_4$CH$_3$ | | —CH$_3$ | H | —Ph | 1 | 3 |
| H | -pyrazolyl | H | H | —(CH$_2$)$_2$CH$_3$ | | —CH$_3$ | H | —Ph | 1 | 3 |
| H | -pyrazolyl | H | H | —(CH$_2$)$_3$CH$_3$ | | —CH$_3$ | H | —Ph | 1 | 3 |

TABLE 1-continued

| Positions of $R_1$, $R_2$, $R_3$ on the phenyl nucleus | | | | $R_4$ | $R_5$ | $R_6$ | Y | k | l |
|---|---|---|---|---|---|---|---|---|---|
| 2- | 3- | 4- | 5- | | | | | | |
| H | -pyrazolyl | H | H | —(CH$_2$)$_2$CH$_3$ | —CH$_3$ | H | —Ph | 1 | 3 |
| H | H | -pyrazolyl | H | —(CH$_2$)$_3$CH$_3$ | —CH$_3$ | H | —Ph | 1 | 3 |
| H | H | -pyrazolyl | H | —(CH$_2$)$_4$CH$_3$ | —CH$_3$ | H | —Ph | 1 | 3 |
| H | —OCH$_3$ | -pyrazolyl | H | —(CH$_2$)$_2$CH$_3$ | —CH$_3$ | H | —Ph | 1 | 2 |
| H | —OCH$_3$ | -pyrazolyl | H | —(CH$_2$)$_3$CH$_3$ | —CH$_3$ | H | —Ph | 1 | 2 |
| H | —OCH$_3$ | -pyrazolyl | H | —(CH$_2$)$_4$CH$_3$ | —CH$_3$ | H | —Ph | 1 | 2 |
| H | —OCH$_3$ | -pyrazolyl | H | —(CH$_2$)$_2$CH$_3$ | —CH$_3$ | H | —Ph | 1 | 3 |
| H | —OCH$_3$ | -pyrazolyl | H | —(CH$_2$)$_3$CH$_3$ | —CH$_3$ | H | —Ph | 1 | 3 |
| H | —OCH$_3$ | -pyrazolyl | H | —(CH$_2$)$_4$CH$_3$ | —CH$_3$ | H | —Ph | 1 | 3 |
| -pyrazolyl | H | H | —OCH$_3$ | —(CH$_2$)$_2$CH$_3$ | —CH$_3$ | H | —Ph | 1 | 2 |
| -pyrazolyl | H | H | —OCH$_3$ | —(CH$_2$)$_3$CH$_3$ | —CH$_3$ | H | —Ph | 1 | 2 |
| -pyrazolyl | H | H | —OCH$_3$ | —(CH$_2$)$_4$CH$_3$ | —CH$_3$ | H | —Ph | 1 | 2 |
| -pyrazolyl | H | H | —OCH$_3$ | —(CH$_2$)$_2$CH$_3$ | —CH$_3$ | H | —Ph | 1 | 3 |
| -pyrazolyl | H | H | —OCH$_3$ | —(CH$_2$)$_3$CH$_3$ | —CH$_3$ | H | —Ph | 1 | 3 |
| -pyrazolyl | H | H | —OCH$_3$ | —(CH$_2$)$_4$CH$_3$ | —CH$_3$ | H | —Ph | 1 | 3 |
| —OCH$_3$ | H | H | -pyrazolyl | —(CH$_2$)$_2$CH$_3$ | —CH$_3$ | H | —Ph | 1 | 2 |
| —OCH$_3$ | H | H | -pyrazolyl | —(CH$_2$)$_3$CH$_3$ | —CH$_3$ | H | —Ph | 1 | 2 |
| —OCH$_3$ | H | H | -pyrazolyl | —(CH$_2$)$_4$CH$_3$ | —CH$_3$ | H | —Ph | 1 | 2 |
| —OCH$_3$ | H | H | -pyrazolyl | —(CH$_2$)$_2$CH$_3$ | —CH$_3$ | H | —Ph | 1 | 3 |
| —OCH$_3$ | H | H | -pyrazolyl | —(CH$_2$)$_3$CH$_3$ | —CH$_3$ | H | —Ph | 1 | 3 |
| —OCH$_3$ | H | H | -pyrazolyl | —(CH$_2$)$_4$CH$_3$ | —CH$_3$ | H | —Ph | 1 | 3 |
| H | -pyrazolyl | —OCH$_3$ | H | —(CH$_2$)$_2$CH$_3$ | —CH$_3$ | H | —Ph | 1 | 2 |
| H | -pyrazolyl | —OCH$_3$ | H | —(CH$_2$)$_3$CH$_3$ | —CH$_3$ | H | —Ph | 1 | 2 |
| H | -pyrazolyl | —OCH$_3$ | H | —(CH$_2$)$_4$CH$_3$ | —CH$_3$ | H | —Ph | 1 | 2 |
| H | -pyrazolyl | —OCH$_3$ | H | —(CH$_2$)$_2$CH$_3$ | —CH$_3$ | H | —Ph | 1 | 3 |
| H | -pyrazolyl | —OCH$_3$ | H | —(CH$_2$)$_3$CH$_3$ | —CH$_3$ | H | —Ph | 1 | 3 |
| H | -pyrazolyl | —OCH$_3$ | H | —(CH$_2$)$_4$CH$_3$ | —CH$_3$ | H | —Ph | 1 | 3 |
| | 2-OCH$_2$O-3 | H | -pyrazolyl | —(CH$_2$)$_2$CH$_3$ | —CH$_3$ | H | —Ph | 1 | 2 |
| | 2-OCH$_2$O-3 | H | -pyrazolyl | —(CH$_2$)$_4$CH$_3$ | —CH$_3$ | H | —Ph | 1 | 2 |
| | 2-OCH$_2$O-3 | H | -pyrazolyl | —(CH$_2$)$_2$CH$_3$ | —CH$_3$ | H | —Ph | 1 | 3 |
| | 2-OCH$_2$O-3 | H | -pyrazolyl | —(CH$_2$)$_4$CH$_3$ | —CH$_3$ | H | —Ph | 1 | 3 |
| —OCH$_3$ | —OCH$_3$ | H | -pyrazolyl | —(CH$_2$)$_2$CH$_3$ | —CH$_3$ | H | —Ph | 1 | 2 |
| —OCH$_3$ | —OCH$_3$ | H | -pyrazolyl | —(CH$_2$)$_4$CH$_3$ | —CH$_3$ | H | —Ph | 1 | 2 |
| —OCH$_3$ | —OCH$_3$ | H | -pyrazolyl | —(CH$_2$)$_2$CH$_3$ | —CH$_3$ | H | —Ph | 1 | 3 |
| —OCH$_3$ | —OCH$_3$ | H | -pyrazolyl | —(CH$_2$)$_4$CH$_3$ | —CH$_3$ | H | —Ph | 1 | 3 |
| -pyrazolyl | H | H | H | —(CH$_2$)$_2$CH$_3$ | —CH$_3$ | H | —Ph | 2 | 2 |
| -pyrazolyl | H | H | H | —(CH$_2$)$_3$CH$_3$ | —CH$_3$ | H | —Ph | 2 | 2 |
| -pyrazolyl | H | H | H | —(CH$_2$)$_4$CH$_3$ | —CH$_3$ | H | —Ph | 2 | 2 |
| H | -pyrazolyl | H | H | —(CH$_2$)$_2$CH$_3$ | —CH$_3$ | H | —Ph | 2 | 2 |
| H | -pyrazolyl | H | H | —(CH$_2$)$_3$CH$_3$ | —CH$_3$ | H | —Ph | 2 | 2 |
| H | -pyrazolyl | H | H | —(CH$_2$)$_4$CH$_3$ | —CH$_3$ | H | —Ph | 2 | 2 |
| H | H | -pyrazolyl | H | —(CH$_2$)$_2$CH$_3$ | —CH$_3$ | H | —Ph | 2 | 2 |
| H | H | -pyrazolyl | H | —(CH$_2$)$_3$CH$_3$ | —CH$_3$ | H | —Ph | 2 | 2 |
| H | H | -pyrazolyl | H | —(CH$_2$)$_4$CH$_3$ | —CH$_3$ | H | —Ph | 2 | 2 |
| -pyrazolyl | H | H | H | —(CH$_2$)$_2$CH$_3$ | —CH$_3$ | H | —Ph | 2 | 3 |
| -pyrazolyl | H | H | H | —(CH$_2$)$_3$CH$_3$ | —CH$_3$ | H | —Ph | 2 | 3 |
| -pyrazolyl | H | H | H | —(CH$_2$)$_4$CH$_3$ | —CH$_3$ | H | —Ph | 2 | 3 |
| H | -pyrazolyl | H | H | —(CH$_2$)$_2$CH$_3$ | —CH$_3$ | H | —Ph | 2 | 3 |
| H | -pyrazolyl | H | H | —(CH$_2$)$_3$CH$_3$ | —CH$_3$ | H | —Ph | 2 | 3 |
| H | -pyrazolyl | H | H | —(CH$_2$)$_4$CH$_3$ | —CH$_3$ | H | —Ph | 2 | 3 |
| H | H | -pyrazolyl | H | —(CH$_2$)$_2$CH$_3$ | —CH$_3$ | H | —Ph | 2 | 3 |
| H | H | -pyrazolyl | H | —(CH$_2$)$_3$CH$_3$ | —CH$_3$ | H | —Ph | 2 | 3 |
| H | H | -pyrazolyl | H | —(CH$_2$)$_4$CH$_3$ | —CH$_3$ | H | —Ph | 2 | 3 |
| H | —OCH$_3$ | -pyrazolyl | H | —(CH$_2$)$_2$CH$_3$ | —CH$_3$ | H | —Ph | 2 | 2 |
| H | —OCH$_3$ | -pyrazolyl | H | —(CH$_2$)$_3$CH$_3$ | —CH$_3$ | H | —Ph | 2 | 2 |
| H | —OCH$_3$ | -pyrazolyl | H | —(CH$_2$)$_4$CH$_3$ | —CH$_3$ | H | —Ph | 2 | 2 |
| H | —OCH$_3$ | -pyrazolyl | H | —(CH$_2$)$_2$CH$_3$ | —CH$_3$ | H | —Ph | 2 | 3 |
| H | —OCH$_3$ | -pyrazolyl | H | —(CH$_2$)$_3$CH$_3$ | —CH$_3$ | H | —Ph | 2 | 3 |
| H | —OCH$_3$ | -pyrazolyl | H | —(CH$_2$)$_4$CH$_3$ | —CH$_3$ | H | —Ph | 2 | 3 |
| -pyrazolyl | H | H | —OCH$_3$ | —(CH$_2$)$_2$CH$_3$ | —CH$_3$ | H | —Ph | 2 | 2 |
| -pyrazolyl | H | H | —OCH$_3$ | —(CH$_2$)$_3$CH$_3$ | —CH$_3$ | H | —Ph | 2 | 2 |
| -pyrazolyl | H | H | —OCH$_3$ | —(CH$_2$)$_4$CH$_3$ | —CH$_3$ | H | —Ph | 2 | 2 |
| -pyrazolyl | H | H | —OCH$_3$ | —(CH$_2$)$_2$CH$_3$ | —CH$_3$ | H | —Ph | 2 | 3 |
| -pyrazolyl | H | H | —OCH$_3$ | —(CH$_2$)$_3$CH$_3$ | —CH$_3$ | H | —Ph | 2 | 3 |
| -pyrazolyl | H | H | —OCH$_3$ | —(CH$_2$)$_4$CH$_3$ | —CH$_3$ | H | —Ph | 2 | 3 |
| | 2-OCH$_2$O-3 | H | -pyrazolyl | —(CH$_2$)$_2$CH$_3$ | —CH$_3$ | H | —Ph | 2 | 2 |
| | 2-OCH$_2$O-3 | H | -pyrazolyl | —(CH$_2$)$_4$CH$_3$ | —CH$_3$ | H | —Ph | 2 | 2 |
| | 2-OCH$_2$O-3 | H | -pyrazolyl | —(CH$_2$)$_2$CH$_3$ | —CH$_3$ | H | —Ph | 2 | 3 |
| | 2-OCH$_2$O-3 | H | -pyrazolyl | —(CH$_2$)$_4$CH$_3$ | —CH$_3$ | H | —Ph | 2 | 3 |
| —OCH$_3$ | —OCH$_3$ | H | -pyrazolyl | —(CH$_2$)$_2$CH$_3$ | —CH$_3$ | H | —Ph | 2 | 2 |
| —OCH$_3$ | —OCH$_3$ | H | -pyrazolyl | —(CH$_2$)$_4$CH$_3$ | —CH$_3$ | H | —Ph | 2 | 2 |
| —OCH$_3$ | —OCH$_3$ | H | -pyrazolyl | —(CH$_2$)$_2$CH$_3$ | —CH$_3$ | H | —Ph | 2 | 3 |
| —OCH$_3$ | —OCH$_3$ | H | -pyrazolyl | —(CH$_2$)$_4$CH$_3$ | —CH$_3$ | H | —Ph | 2 | 3 |
| —OCH$_3$ | H | H | -pyrazolyl | —(CH$_2$)$_2$CH$_3$ | —CH$_3$ | H | —Ph | 2 | 2 |

TABLE 1-continued

| Positions of $R_1$, $R_2$, $R_3$ on the phenyl nucleus | | | | | | | | | | |
|---|---|---|---|---|---|---|---|---|---|---|
| 2- | 3- | 4- | 5- | $R_4$ | | $R_5$ | $R_6$ | Y | k | l |
| —OCH$_3$ | H | H | -pyrazolyl | —(CH$_2$)$_2$CH$_3$ | | —CH$_3$ | H | —Ph | 2 | 2 |
| —OCH$_3$ | H | H | -pyrazolyl | —(CH$_2$)$_3$CH$_3$ | | —CH$_3$ | H | —Ph | 2 | 2 |
| —OCH$_3$ | H | H | -pyrazolyl | —(CH$_2$)$_4$CH$_3$ | | —CH$_3$ | H | —Ph | 2 | 2 |
| —OCH$_3$ | H | H | -pyrazolyl | —(CH$_2$)$_2$CH$_3$ | | —CH$_3$ | H | —Ph | 2 | 3 |
| —OCH$_3$ | H | H | -pyrazolyl | —(CH$_2$)$_3$CH$_3$ | | —CH$_3$ | H | —Ph | 2 | 3 |
| —OCH$_3$ | H | H | -pyrazolyl | —(CH$_2$)$_4$CH$_3$ | | —CH$_3$ | H | —Ph | 2 | 3 |
| H | -pyrazolyl | —OCH$_3$ | H | —(CH$_2$)$_2$CH$_3$ | | —CH$_3$ | H | —Ph | 2 | 2 |
| H | -pyrazolyl | —OCH$_3$ | H | —(CH$_2$)$_3$CH$_3$ | | —CH$_3$ | H | —Ph | 2 | 2 |
| H | -pyrazolyl | —OCH$_3$ | H | —(CH$_2$)$_4$CH$_3$ | | —CH$_3$ | H | —Ph | 2 | 2 |
| H | -pyrazolyl | —OCH$_3$ | H | —(CH$_2$)$_2$CH$_3$ | | —CH$_3$ | H | —Ph | 2 | 3 |
| H | -pyrazolyl | —OCH$_3$ | H | —(CH$_2$)$_3$CH$_3$ | | —CH$_3$ | H | —Ph | 2 | 3 |
| H | -pyrazolyl | —OCH$_3$ | H | —(CH$_2$)$_4$CH$_3$ | | —CH$_3$ | H | —Ph | 2 | 3 |
| -pyrazolyl | H | H | H | -cyclobutyl | | —CH$_3$ | H | —Ph | 1 | 2 |
| -pyrazolyl | H | H | H | -cyclopentyl | | —CH$_3$ | H | —Ph | 1 | 2 |
| -pyrazolyl | H | H | H | -cyclohexyl | | —CH$_3$ | H | —Ph | 1 | 2 |
| H | -pyrazolyl | H | H | -cyclobutyl | | —CH$_3$ | H | —Ph | 1 | 2 |
| H | -pyrazolyl | H | H | -cyclopentyl | | —CH$_3$ | H | —Ph | 1 | 2 |
| H | -pyrazolyl | H | H | -cyclohexyl | | —CH$_3$ | H | —Ph | 1 | 2 |
| H | H | -pyrazolyl | H | -cyclobutyl | | —CH$_3$ | H | —Ph | 1 | 2 |
| H | H | -pyrazolyl | H | -cyclopentyl | | —CH$_3$ | H | —Ph | 1 | 2 |
| H | H | -pyrazolyl | H | -cyclohexyl | | —CH$_3$ | H | —Ph | 1 | 2 |
| -pyrazolyl | H | H | H | -cyclobutyl | | —CH$_3$ | H | —Ph | 1 | 3 |
| -pyrazolyl | H | H | H | -cyclopentyl | | —CH$_3$ | H | —Ph | 1 | 3 |
| -pyrazolyl | H | H | H | -cyclohexyl | | —CH$_3$ | H | —Ph | 1 | 3 |
| H | -pyrazolyl | H | H | -cyclobutyl | | —CH$_3$ | H | —Ph | 1 | 3 |
| H | -pyrazolyl | H | H | -cyclopentyl | | —CH$_3$ | H | —Ph | 1 | 3 |
| H | -pyrazolyl | H | H | -cyclohexyl | | —CH$_3$ | H | —Ph | 1 | 3 |
| H | H | -pyrazolyl | H | -cyclobutyl | | —CH$_3$ | H | —Ph | 1 | 3 |
| H | H | -pyrazolyl | H | -cyclopentyl | | —CH$_3$ | H | —Ph | 1 | 3 |
| H | H | -pyrazolyl | H | -cyclohexyl | | —CH$_3$ | H | —Ph | 1 | 3 |
| H | —OCH$_3$ | -pyrazolyl | H | -cyclobutyl | | —CH$_3$ | H | —Ph | 1 | 2 |
| H | —OCH$_3$ | -pyrazolyl | H | -cyclopentyl | | —CH$_3$ | H | —Ph | 1 | 2 |
| H | —OCH$_3$ | -pyrazolyl | H | -cyclohexyl | | —CH$_3$ | H | —Ph | 1 | 2 |
| H | —OCH$_3$ | -pyrazolyl | H | -cyclobutyl | | —CH$_3$ | H | —Ph | 1 | 3 |
| H | —OCH$_3$ | -pyrazolyl | H | -cyclopentyl | | —CH$_3$ | H | —Ph | 1 | 3 |
| H | —OCH$_3$ | -pyrazolyl | H | -cyclohexyl | | —CH$_3$ | H | —Ph | 1 | 3 |
| -pyrazolyl | H | H | —OCH$_3$ | -cyclobutyl | | —CH$_3$ | H | —Ph | 1 | 2 |
| -pyrazolyl | H | H | —OCH$_3$ | -cyclopentyl | | —CH$_3$ | H | —Ph | 1 | 2 |
| -pyrazolyl | H | H | —OCH$_3$ | -cyclohexyl | | —CH$_3$ | H | —Ph | 1 | 2 |
| -pyrazolyl | H | H | —OCH$_3$ | -cyclobutyl | | —CH$_3$ | H | —Ph | 1 | 3 |
| -pyrazolyl | H | H | —OCH$_3$ | -cyclopentyl | | —CH$_3$ | H | —Ph | 1 | 3 |
| -pyrazolyl | H | H | —OCH$_3$ | -cyclohexyl | | —CH$_3$ | H | —Ph | 1 | 3 |
| | 2-OCH$_2$O-3 | H | | -pyrazolyl | -cyclobutyl | —CH$_3$ | H | —Ph | 1 | 2 |
| | 2-OCH$_2$O-3 | H | | -pyrazolyl | -cyclopentyl | —CH$_3$ | H | —Ph | 1 | 2 |
| | 2-OCH$_2$O-3 | H | | -pyrazolyl | -cyclohexyl | —CH$_3$ | H | —Ph | 1 | 2 |
| | 2-OCH$_2$O-3 | H | | -pyrazolyl | -cyclobutyl | —CH$_3$ | H | —Ph | 1 | 3 |
| | 2-OCH$_2$O-3 | H | | -pyrazolyl | -cyclopentyl | —CH$_3$ | H | —Ph | 1 | 3 |
| | 2-OCH$_2$O-3 | H | | -pyrazolyl | -cyclohexyl | —CH$_3$ | H | —Ph | 1 | 3 |
| —OCH$_3$ | —OCH$_3$ | H | | -pyrazolyl | -cyclobutyl | —CH$_3$ | H | —Ph | 1 | 2 |
| —OCH$_3$ | —OCH$_3$ | H | | -pyrazolyl | -cyclopentyl | —CH$_3$ | H | —Ph | 1 | 2 |
| —OCH$_3$ | —OCH$_3$ | H | | -pyrazolyl | -cyclohexyl | —CH$_3$ | H | —Ph | 1 | 2 |
| —OCH$_3$ | —OCH$_3$ | H | | -pyrazolyl | -cyclobutyl | —CH$_3$ | H | —Ph | 1 | 3 |
| —OCH$_3$ | —OCH$_3$ | H | | -pyrazolyl | -cyclopentyl | —CH$_3$ | H | —Ph | 1 | 3 |
| —OCH$_3$ | —OCH$_3$ | H | | -pyrazolyl | -cyclohexyl | —CH$_3$ | H | —Ph | 1 | 3 |
| —OCH$_3$ | H | H | | -pyrazolyl | -cyclobutyl | —CH$_3$ | H | —Ph | 1 | 2 |
| —OCH$_3$ | H | H | | -pyrazolyl | -cyclopentyl | —CH$_3$ | H | —Ph | 1 | 2 |
| —OCH$_3$ | H | H | | -pyrazolyl | -cyclohexyl | —CH$_3$ | H | —Ph | 1 | 2 |
| —OCH$_3$ | H | H | | -pyrazolyl | -cyclobutyl | —CH$_3$ | H | —Ph | 1 | 3 |
| —OCH$_3$ | H | H | | -pyrazolyl | -cyclopentyl | —CH$_3$ | H | —Ph | 1 | 3 |
| —OCH$_3$ | H | H | | -pyrazolyl | -cyclohexyl | —CH$_3$ | H | —Ph | 1 | 3 |
| H | -pyrazolyl | —OCH$_3$ | H | -cyclobutyl | | —CH$_3$ | H | —Ph | 1 | 2 |
| H | -pyrazolyl | —OCH$_3$ | H | -cyclopentyl | | —CH$_3$ | H | —Ph | 1 | 2 |
| H | -pyrazolyl | —OCH$_3$ | H | -cyclohexyl | | —CH$_3$ | H | —Ph | 1 | 2 |
| H | -pyrazolyl | —OCH$_3$ | H | -cyclobutyl | | —CH$_3$ | H | —Ph | 1 | 3 |
| H | -pyrazolyl | —OCH$_3$ | H | -cyclopentyl | | —CH$_3$ | H | —Ph | 1 | 3 |
| H | -pyrazolyl | —OCH$_3$ | H | -cyclohexyl | | —CH$_3$ | H | —Ph | 1 | 3 |
| -pyrazolyl | H | H | H | -cyclobutyl | | —CH$_3$ | H | —Ph | 2 | 2 |
| -pyrazolyl | H | H | H | -cyclopentyl | | —CH$_3$ | H | —Ph | 2 | 2 |
| -pyrazolyl | H | H | H | -cyclohexyl | | —CH$_3$ | H | —Ph | 2 | 2 |
| H | -pyrazolyl | H | H | -cyclobutyl | | —CH$_3$ | H | —Ph | 2 | 2 |
| H | -pyrazolyl | H | H | -cyclopentyl | | —CH$_3$ | H | —Ph | 2 | 2 |
| H | -pyrazolyl | H | H | -cyclohexyl | | —CH$_3$ | H | —Ph | 2 | 2 |
| H | H | -pyrazolyl | H | -cyclobutyl | | —CH$_3$ | H | —Ph | 2 | 2 |
| H | H | -pyrazolyl | H | -cyclopentyl | | —CH$_3$ | H | —Ph | 2 | 2 |
| H | H | -pyrazolyl | H | -cyclohexyl | | —CH$_3$ | H | —Ph | 2 | 2 |
| -pyrazolyl | H | H | H | -cyclobutyl | | —CH$_3$ | H | —Ph | 2 | 3 |

TABLE 1-continued

| Positions of $R_1$, $R_2$, $R_3$ on the phenyl nucleus | | | | | | | | | | |
|---|---|---|---|---|---|---|---|---|---|---|
| 2- | 3- | 4- | 5- | $R_4$ | $R_5$ | $R_6$ | Y | k | l | |
| -pyrazolyl | H | H | H | -cyclopentyl | —$CH_3$ | H | —Ph | 2 | 3 | |
| -pyrazolyl | H | H | H | -cyclohexyl | —$CH_3$ | H | —Ph | 2 | 3 | |
| H | -pyrazolyl | H | H | -cyclobutyl | —$CH_3$ | H | —Ph | 2 | 3 | |
| H | -pyrazolyl | H | H | -cyclopentyl | —$CH_3$ | H | —Ph | 2 | 3 | |
| H | -pyrazolyl | H | H | -cyclohexyl | —$CH_3$ | H | —Ph | 2 | 3 | |
| H | H | -pyrazolyl | H | -cyclobutyl | —$CH_3$ | H | —Ph | 2 | 3 | |
| H | H | -pyrazolyl | H | -cyclopentyl | —$CH_3$ | H | —Ph | 2 | 3 | |
| H | H | -pyrazolyl | H | -cyclohexyl | —$CH_3$ | H | —Ph | 2 | 3 | |
| H | —$OCH_3$ | -pyrazolyl | H | -cyclobutyl | —$CH_3$ | H | —Ph | 2 | 2 | |
| H | —$OCH_3$ | -pyrazolyl | H | -cyclopentyl | —$CH_3$ | H | —Ph | 2 | 2 | |
| H | —$OCH_3$ | -pyrazolyl | H | -cyclohexyl | —$CH_3$ | H | —Ph | 2 | 2 | |
| H | —$OCH_3$ | -pyrazolyl | H | -cyclobutyl | —$CH_3$ | H | —Ph | 2 | 3 | |
| H | —$OCH_3$ | -pyrazolyl | H | -cyclopentyl | —$CH_3$ | H | —Ph | 2 | 3 | |
| H | —$OCH_3$ | -pyrazolyl | H | -cyclohexyl | —$CH_3$ | H | —Ph | 2 | 3 | |
| -pyrazolyl | H | H | —$OCH_3$ | -cyclobutyl | —$CH_3$ | H | —Ph | 2 | 2 | |
| -pyrazolyl | H | H | —$OCH_3$ | -cyclopentyl | —$CH_3$ | H | —Ph | 2 | 2 | |
| -pyrazolyl | H | H | —$OCH_3$ | -cyclohexyl | —$CH_3$ | H | —Ph | 2 | 2 | |
| -pyrazolyl | H | H | —$OCH_3$ | -cyclobutyl | —$CH_3$ | H | —Ph | 2 | 3 | |
| -pyrazolyl | H | H | —$OCH_3$ | -cyclopentyl | —$CH_3$ | H | —Ph | 2 | 3 | |
| -pyrazolyl | H | H | —$OCH_3$ | -cyclohexyl | —$CH_3$ | H | —Ph | 2 | 3 | |
| | 2-$OCH_2$O-3 | H | | -pyrazolyl | -cyclobutyl | —$CH_3$ | H | —Ph | 2 | 2 |
| | 2-$OCH_2$O-3 | H | | -pyrazolyl | -cyclopentyl | —$CH_3$ | H | —Ph | 2 | 2 |
| | 2-$OCH_2$O-3 | H | | -pyrazolyl | -cyclohexyl | —$CH_3$ | H | —Ph | 2 | 2 |
| | 2-$OCH_2$O-3 | H | | -pyrazolyl | -cyclobutyl | —$CH_3$ | H | —Ph | 2 | 3 |
| | 2-$OCH_2$O-3 | H | | -pyrazolyl | -cyclopentyl | —$CH_3$ | H | —Ph | 2 | 3 |
| | 2-$OCH_2$O-3 | H | | -pyrazolyl | -cyclohexyl | —$CH_3$ | H | —Ph | 2 | 3 |
| —$OCH_3$ | —$OCH_3$ | H | -pyrazolyl | -cyclobutyl | —$CH_3$ | H | —Ph | 2 | 2 | |
| —$OCH_3$ | —$OCH_3$ | H | -pyrazolyl | -cyclopentyl | —$CH_3$ | H | —Ph | 2 | 2 | |
| —$OCH_3$ | —$OCH_3$ | H | -pyrazolyl | -cyclohexyl | —$CH_3$ | H | —Ph | 2 | 2 | |
| —$OCH_3$ | —$OCH_3$ | H | -pyrazolyl | -cyclobutyl | —$CH_3$ | H | —Ph | 2 | 3 | |
| —$OCH_3$ | —$OCH_3$ | H | -pyrazolyl | -cyclopentyl | —$CH_3$ | H | —Ph | 2 | 3 | |
| —$OCH_3$ | —$OCH_3$ | H | -pyrazolyl | -cyclohexyl | —$CH_3$ | H | —Ph | 2 | 3 | |
| —$OCH_3$ | H | H | -pyrazolyl | -cyclobutyl | —$CH_3$ | H | —Ph | 2 | 2 | |
| —$OCH_3$ | H | H | -pyrazolyl | -cyclopentyl | —$CH_3$ | H | —Ph | 2 | 2 | |
| —$OCH_3$ | H | H | -pyrazolyl | -cyclohexyl | —$CH_3$ | H | —Ph | 2 | 2 | |
| —$OCH_3$ | H | H | -pyrazolyl | -cyclobutyl | —$CH_3$ | H | —Ph | 2 | 3 | |
| —$OCH_3$ | H | H | -pyrazolyl | -cyclopentyl | —$CH_3$ | H | —Ph | 2 | 3 | |
| —$OCH_3$ | H | H | -pyrazolyl | -cyclohexyl | —$CH_3$ | H | —Ph | 2 | 3 | |
| H | -pyrazolyl | —$OCH_3$ | H | -cyclobutyl | —$CH_3$ | H | —Ph | 2 | 2 | |
| H | -pyrazolyl | —$OCH_3$ | H | -cyclopentyl | —$CH_3$ | H | —Ph | 2 | 2 | |
| H | -pyrazolyl | —$OCH_3$ | H | -cyclohexyl | —$CH_3$ | H | —Ph | 2 | 2 | |
| H | -pyrazolyl | —$OCH_3$ | H | -cyclobutyl | —$CH_3$ | H | —Ph | 2 | 3 | |
| H | -pyrazolyl | —$OCH_3$ | H | -cyclopentyl | —$CH_3$ | H | —Ph | 2 | 3 | |
| H | -pyrazolyl | —$OCH_3$ | H | -cyclohexyl | —$CH_3$ | H | —Ph | 2 | 3 | |
| -triazolyl | H | H | H | —$(CH_2)_2CH_3$ | —$CH_3$ | H | —Ph | 1 | 2 | |
| -triazolyl | H | H | H | —$(CH_2)_3CH_3$ | —$CH_3$ | H | —Ph | 1 | 2 | |
| -triazolyl | H | H | H | —$(CH_2)_4CH_3$ | —$CH_3$ | H | —Ph | 1 | 2 | |
| H | -triazolyl | H | H | —$(CH_2)_2CH_3$ | —$CH_3$ | H | —Ph | 1 | 2 | |
| H | -triazolyl | H | H | —$(CH_2)_3CH_3$ | —$CH_3$ | H | —Ph | 1 | 2 | |
| H | -triazolyl | H | H | —$(CH_2)_4CH_3$ | —$CH_3$ | H | —Ph | 1 | 2 | |
| H | H | -triazolyl | H | —$(CH_2)_2CH_3$ | —$CH_3$ | H | —Ph | 1 | 2 | |
| H | H | -triazolyl | H | —$(CH_2)_3CH_3$ | —$CH_3$ | H | —Ph | 1 | 2 | |
| H | H | -triazolyl | H | —$(CH_2)_4CH_3$ | —$CH_3$ | H | —Ph | 1 | 2 | |
| -triazolyl | H | H | H | —$(CH_2)_2CH_3$ | —$CH_3$ | H | —Ph | 1 | 3 | |
| -triazolyl | H | H | H | —$(CH_2)_3CH_3$ | —$CH_3$ | H | —Ph | 1 | 3 | |
| -triazolyl | H | H | H | —$(CH_2)_4CH_3$ | —$CH_3$ | H | —Ph | 1 | 3 | |
| H | -triazolyl | H | H | —$(CH_2)_2CH_3$ | —$CH_3$ | H | —Ph | 1 | 3 | |
| H | -triazolyl | H | H | —$(CH_2)_3CH_3$ | —$CH_3$ | H | —Ph | 1 | 3 | |
| H | -triazolyl | H | H | —$(CH_2)_4CH_3$ | —$CH_3$ | H | —Ph | 1 | 3 | |
| H | H | -triazolyl | H | —$(CH_2)_2CH_3$ | —$CH_3$ | H | —Ph | 1 | 3 | |
| H | H | -triazolyl | H | —$(CH_2)_3CH_3$ | —$CH_3$ | H | —Ph | 1 | 3 | |
| H | H | -triazolyl | H | —$(CH_2)_4CH_3$ | —$CH_3$ | H | —Ph | 1 | 3 | |
| H | —$OCH_3$ | -triazolyl | H | —$(CH_2)_2CH_3$ | —$CH_3$ | H | —Ph | 1 | 2 | |
| H | —$OCH_3$ | -triazolyl | H | —$(CH_2)_3CH_3$ | —$CH_3$ | H | —Ph | 1 | 2 | |
| H | —$OCH_3$ | -triazolyl | H | —$(CH_2)_4CH_3$ | —$CH_3$ | H | —Ph | 1 | 2 | |
| H | —$OCH_3$ | -triazolyl | H | —$(CH_2)_2CH_3$ | —$CH_3$ | H | —Ph | 1 | 3 | |
| H | —$OCH_3$ | -triazolyl | H | —$(CH_2)_3CH_3$ | —$CH_3$ | H | —Ph | 1 | 3 | |
| H | —$OCH_3$ | -triazolyl | H | —$(CH_2)_4CH_3$ | —$CH_3$ | H | —Ph | 1 | 3 | |
| -triazolyl | H | H | —$OCH_3$ | —$(CH_2)_2CH_3$ | —$CH_3$ | H | —Ph | 1 | 2 | |
| -triazolyl | H | H | —$OCH_3$ | —$(CH_2)_3CH_3$ | —$CH_3$ | H | —Ph | 1 | 2 | |
| -triazolyl | H | H | —$OCH_3$ | —$(CH_2)_4CH_3$ | —$CH_3$ | H | —Ph | 1 | 2 | |
| -triazolyl | H | H | —$OCH_3$ | —$(CH_2)_2CH_3$ | —$CH_3$ | H | —Ph | 1 | 3 | |
| -triazolyl | H | H | —$OCH_3$ | —$(CH_2)_3CH_3$ | —$CH_3$ | H | —Ph | 1 | 3 | |
| -triazolyl | H | H | —$OCH_3$ | —$(CH_2)_4CH_3$ | —$CH_3$ | H | —Ph | 1 | 3 | |
| | 2-$OCH_2$O-3 | H | | -triazolyl | —$(CH_2)_2CH_3$ | —$CH_3$ | H | —Ph | 1 | 2 |

TABLE 1-continued

| Positions of $R_1$, $R_2$, $R_3$ on the phenyl nucleus | | | | | | | | | | |
|---|---|---|---|---|---|---|---|---|---|---|
| 2- | 3- | 4- | 5- | $R_4$ | | $R_5$ | $R_6$ | Y | k | l |
|  | 2-OCH$_2$O-3 | H | -triazolyl | —(CH$_2$)$_2$CH$_3$ | | —CH$_3$ | H | —Ph | 1 | 2 |
|  | 2-OCH$_2$O-3 | H | -triazolyl | —(CH$_2$)$_2$CH$_3$ | | —CH$_3$ | H | —Ph | 1 | 3 |
|  | 2-OCH$_2$O-3 | H | -triazolyl | —(CH$_2$)$_4$CH$_3$ | | —CH$_3$ | H | —Ph | 1 | 3 |
| —OCH$_3$ | —OCH$_3$ | H | -triazolyl | —(CH$_2$)$_2$CH$_3$ | | —CH$_3$ | H | —Ph | 1 | 2 |
| —OCH$_3$ | —OCH$_3$ | H | -triazolyl | —(CH$_2$)$_4$CH$_3$ | | —CH$_3$ | H | —Ph | 1 | 2 |
| —OCH$_3$ | —OCH$_3$ | H | -triazolyl | —(CH$_2$)$_2$CH$_3$ | | —CH$_3$ | H | —Ph | 1 | 3 |
| —OCH$_3$ | —OCH$_3$ | H | -triazolyl | —(CH$_2$)$_4$CH$_3$ | | —CH$_3$ | H | —Ph | 1 | 3 |
| —OCH$_3$ | H | H | -triazolyl | —(CH$_2$)$_2$CH$_3$ | | —CH$_3$ | H | —Ph | 1 | 2 |
| —OCH$_3$ | H | H | -triazolyl | —(CH$_2$)$_3$CH$_3$ | | —CH$_3$ | H | —Ph | 1 | 2 |
| —OCH$_3$ | H | H | -triazolyl | —(CH$_2$)$_4$CH$_3$ | | —CH$_3$ | H | —Ph | 1 | 2 |
| —OCH$_3$ | H | H | -triazolyl | —(CH$_2$)$_2$CH$_3$ | | —CH$_3$ | H | —Ph | 1 | 3 |
| —OCH$_3$ | H | H | -triazolyl | —(CH$_2$)$_3$CH$_3$ | | —CH$_3$ | H | —Ph | 1 | 3 |
| —OCH$_3$ | H | H | -triazolyl | —(CH$_2$)$_4$CH$_3$ | | —CH$_3$ | H | —Ph | 1 | 3 |
| H | -triazolyl | —OCH$_3$ | H | —(CH$_2$)$_2$CH$_3$ | | —CH$_3$ | H | —Ph | 1 | 2 |
| H | -triazolyl | —OCH$_3$ | H | —(CH$_2$)$_3$CH$_3$ | | —CH$_3$ | H | —Ph | 1 | 2 |
| H | -triazolyl | —OCH$_3$ | H | —(CH$_2$)$_4$CH$_3$ | | —CH$_3$ | H | —Ph | 1 | 2 |
| H | -triazolyl | —OCH$_3$ | H | —(CH$_2$)$_2$CH$_3$ | | —CH$_3$ | H | —Ph | 1 | 3 |
| H | -triazolyl | —OCH$_3$ | H | —(CH$_2$)$_3$CH$_3$ | | —CH$_3$ | H | —Ph | 1 | 3 |
| H | -triazolyl | —OCH$_3$ | H | —(CH$_2$)$_4$CH$_3$ | | —CH$_3$ | H | —Ph | 1 | 3 |
| -triazolyl | H | H | H | —(CH$_2$)$_2$CH$_3$ | | —CH$_3$ | H | —Ph | 2 | 2 |
| -triazolyl | H | H | H | —(CH$_2$)$_3$CH$_3$ | | —CH$_3$ | H | —Ph | 2 | 2 |
| -triazolyl | H | H | H | —(CH$_2$)$_4$CH$_3$ | | —CH$_3$ | H | —Ph | 2 | 2 |
| H | -triazolyl | H | H | —(CH$_2$)$_2$CH$_3$ | | —CH$_3$ | H | —Ph | 2 | 2 |
| H | -triazolyl | H | H | —(CH$_2$)$_3$CH$_3$ | | —CH$_3$ | H | —Ph | 2 | 2 |
| H | -triazolyl | H | H | —(CH$_2$)$_4$CH$_3$ | | —CH$_3$ | H | —Ph | 2 | 2 |
| H | H | -triazolyl | H | —(CH$_2$)$_2$CH$_3$ | | —CH$_3$ | H | —Ph | 2 | 2 |
| H | H | -triazolyl | H | —(CH$_2$)$_3$CH$_3$ | | —CH$_3$ | H | —Ph | 2 | 2 |
| H | H | -triazolyl | H | —(CH$_2$)$_4$CH$_3$ | | —CH$_3$ | H | —Ph | 2 | 2 |
| -triazolyl | H | H | H | —(CH$_2$)$_2$CH$_3$ | | —CH$_3$ | H | —Ph | 2 | 3 |
| -triazolyl | H | H | H | —(CH$_2$)$_3$CH$_3$ | | —CH$_3$ | H | —Ph | 2 | 3 |
| -triazolyl | H | H | H | —(CH$_2$)$_4$CH$_3$ | | —CH$_3$ | H | —Ph | 2 | 3 |
| H | -triazolyl | H | H | —(CH$_2$)$_2$CH$_3$ | | —CH$_3$ | H | —Ph | 2 | 3 |
| H | -triazolyl | H | H | —(CH$_2$)$_3$CH$_3$ | | —CH$_3$ | H | —Ph | 2 | 3 |
| H | -triazolyl | H | H | —(CH$_2$)$_4$CH$_3$ | | —CH$_3$ | H | —Ph | 2 | 3 |
| H | H | -triazolyl | H | —(CH$_2$)$_2$CH$_3$ | | —CH$_3$ | H | —Ph | 2 | 3 |
| H | H | -triazolyl | H | —(CH$_2$)$_3$CH$_3$ | | —CH$_3$ | H | —Ph | 2 | 3 |
| H | H | -triazolyl | H | —(CH$_2$)$_4$CH$_3$ | | —CH$_3$ | H | —Ph | 2 | 3 |
| H | —OCH$_3$ | -triazolyl | H | —(CH$_2$)$_2$CH$_3$ | | —CH$_3$ | H | —Ph | 2 | 2 |
| H | —OCH$_3$ | -triazolyl | H | —(CH$_2$)$_3$CH$_3$ | | —CH$_3$ | H | —Ph | 2 | 2 |
| H | —OCH$_3$ | -triazolyl | H | —(CH$_2$)$_4$CH$_3$ | | —CH$_3$ | H | —Ph | 2 | 2 |
| H | —OCH$_3$ | -triazolyl | H | —(CH$_2$)$_2$CH$_3$ | | —CH$_3$ | H | —Ph | 2 | 3 |
| H | —OCH$_3$ | -triazolyl | H | —(CH$_2$)$_3$CH$_3$ | | —CH$_3$ | H | —Ph | 2 | 3 |
| H | —OCH$_3$ | -triazolyl | H | —(CH$_2$)$_4$CH$_3$ | | —CH$_3$ | H | —Ph | 2 | 3 |
| -triazolyl | H | H | —OCH$_3$ | —(CH$_2$)$_2$CH$_3$ | | —CH$_3$ | H | —Ph | 2 | 2 |
| -triazolyl | H | H | —OCH$_3$ | —(CH$_2$)$_3$CH$_3$ | | —CH$_3$ | H | —Ph | 2 | 2 |
| -triazolyl | H | H | —OCH$_3$ | —(CH$_2$)$_4$CH$_3$ | | —CH$_3$ | H | —Ph | 2 | 2 |
| -triazolyl | H | H | —OCH$_3$ | —(CH$_2$)$_2$CH$_3$ | | —CH$_3$ | H | —Ph | 2 | 3 |
| -triazolyl | H | H | —OCH$_3$ | —(CH$_2$)$_3$CH$_3$ | | —CH$_3$ | H | —Ph | 2 | 3 |
| -triazolyl | H | H | —OCH$_3$ | —(CH$_2$)$_4$CH$_3$ | | —CH$_3$ | H | —Ph | 2 | 3 |
|  | 2-OCH$_2$O-3 | H | -triazolyl | —(CH$_2$)$_2$CH$_3$ | | —CH$_3$ | H | —Ph | 2 | 2 |
|  | 2-OCH$_2$O-3 | H | -triazolyl | —(CH$_2$)$_4$CH$_3$ | | —CH$_3$ | H | —Ph | 2 | 2 |
|  | 2-OCH$_2$O-3 | H | -triazolyl | —(CH$_2$)$_2$CH$_3$ | | —CH$_3$ | H | —Ph | 2 | 3 |
|  | 2-OCH$_2$O-3 | H | -triazolyl | —(CH$_2$)$_4$CH$_3$ | | —CH$_3$ | H | —Ph | 2 | 3 |
| —OCH$_3$ | —OCH$_3$ | H | -triazolyl | —(CH$_2$)$_2$CH$_3$ | | —CH$_3$ | H | —Ph | 2 | 2 |
| —OCH$_3$ | —OCH$_3$ | H | -triazolyl | —(CH$_2$)$_4$CH$_3$ | | —CH$_3$ | H | —Ph | 2 | 2 |
| —OCH$_3$ | —OCH$_3$ | H | -triazolyl | —(CH$_2$)$_2$CH$_3$ | | —CH$_3$ | H | —Ph | 2 | 3 |
| —OCH$_3$ | —OCH$_3$ | H | -triazolyl | —(CH$_2$)$_4$CH$_3$ | | —CH$_3$ | H | —Ph | 2 | 3 |
| —OCH$_3$ | H | H | -triazolyl | —(CH$_2$)$_2$CH$_3$ | | —CH$_3$ | H | —Ph | 2 | 2 |
| —OCH$_3$ | H | H | -triazolyl | —(CH$_2$)$_3$CH$_3$ | | —CH$_3$ | H | —Ph | 2 | 2 |
| —OCH$_3$ | H | H | -triazolyl | —(CH$_2$)$_4$CH$_3$ | | —CH$_3$ | H | —Ph | 2 | 2 |
| —OCH$_3$ | H | H | -triazolyl | —(CH$_2$)$_2$CH$_3$ | | —CH$_3$ | H | —Ph | 2 | 3 |
| —OCH$_3$ | H | H | -triazolyl | —(CH$_2$)$_3$CH$_3$ | | —CH$_3$ | H | —Ph | 2 | 3 |
| —OCH$_3$ | H | H | -triazolyl | —(CH$_2$)$_4$CH$_3$ | | —CH$_3$ | H | —Ph | 2 | 3 |
| H | -triazolyl | —OCH$_3$ | H | —(CH$_2$)$_2$CH$_3$ | | —CH$_3$ | H | —Ph | 2 | 2 |
| H | -triazolyl | —OCH$_3$ | H | —(CH$_2$)$_3$CH$_3$ | | —CH$_3$ | H | —Ph | 2 | 2 |
| H | -triazolyl | —OCH$_3$ | H | —(CH$_2$)$_4$CH$_3$ | | —CH$_3$ | H | —Ph | 2 | 2 |
| H | -triazolyl | —OCH$_3$ | H | —(CH$_2$)$_2$CH$_3$ | | —CH$_3$ | H | —Ph | 2 | 3 |
| H | -triazolyl | —OCH$_3$ | H | —(CH$_2$)$_3$CH$_3$ | | —CH$_3$ | H | —Ph | 2 | 3 |
| H | -triazolyl | —OCH$_3$ | H | —(CH$_2$)$_4$CH$_3$ | | —CH$_3$ | H | —Ph | 2 | 3 |
| -triazolyl | H | H | H | -cyclobutyl | | —CH$_3$ | H | —Ph | 1 | 2 |
| -triazolyl | H | H | H | -cyclopentyl | | —CH$_3$ | H | —Ph | 1 | 2 |
| -triazolyl | H | H | H | -cyclohexyl | | —CH$_3$ | H | —Ph | 1 | 2 |
| H | -triazolyl | H | H | -cyclobutyl | | —CH$_3$ | H | —Ph | 1 | 2 |
| H | -triazolyl | H | H | -cyclopentyl | | —CH$_3$ | H | —Ph | 1 | 2 |
| H | -triazolyl | H | H | -cyclohexyl | | —CH$_3$ | H | —Ph | 1 | 2 |

TABLE 1-continued

| Positions of $R_1$, $R_2$, $R_3$ on the phenyl nucleus | | | | | | | | | | |
|---|---|---|---|---|---|---|---|---|---|---|
| 2- | 3- | 4- | 5- | $R_4$ | | $R_5$ | $R_6$ | Y | k | l |
| H | H | -triazolyl | H | -cyclobutyl | | —$CH_3$ | H | —Ph | 1 | 2 |
| H | H | -triazolyl | H | -cyclopentyl | | —$CH_3$ | H | —Ph | 1 | 2 |
| H | H | -triazolyl | H | -cyclohexyl | | —$CH_3$ | H | —Ph | 1 | 2 |
| -triazolyl | H | H | H | -cyclobutyl | | —$CH_3$ | H | —Ph | 1 | 3 |
| -triazolyl | H | H | H | -cyclopentyl | | —$CH_3$ | H | —Ph | 1 | 3 |
| -triazolyl | H | H | H | -cyclohexyl | | —$CH_3$ | H | —Ph | 1 | 3 |
| H | -triazolyl | H | H | -cyclobutyl | | —$CH_3$ | H | —Ph | 1 | 3 |
| H | -triazolyl | H | H | -cyclopentyl | | —$CH_3$ | H | —Ph | 1 | 3 |
| H | -triazolyl | H | H | -cyclohexyl | | —$CH_3$ | H | —Ph | 1 | 3 |
| H | H | -triazolyl | H | -cyclobutyl | | —$CH_3$ | H | —Ph | 1 | 3 |
| H | H | -triazolyl | H | -cyclopentyl | | —$CH_3$ | H | —Ph | 1 | 3 |
| H | H | -triazolyl | H | -cyclohexyl | | —$CH_3$ | H | —Ph | 1 | 3 |
| H | —$OCH_3$ | -triazolyl | H | -cyclobutyl | | —$CH_3$ | H | —Ph | 1 | 2 |
| H | —$OCH_3$ | -triazolyl | H | -cyclopentyl | | —$CH_3$ | H | —Ph | 1 | 2 |
| H | —$OCH_3$ | -triazolyl | H | -cyclohexyl | | —$CH_3$ | H | —Ph | 1 | 2 |
| H | —$OCH_3$ | -triazolyl | H | -cyclobutyl | | —$CH_3$ | H | —Ph | 1 | 3 |
| H | —$OCH_3$ | -triazolyl | H | -cyclopentyl | | —$CH_3$ | H | —Ph | 1 | 3 |
| H | —$OCH_3$ | -triazolyl | H | -cyclohexyl | | —$CH_3$ | H | —Ph | 1 | 3 |
| -triazolyl | H | H | —$OCH_3$ | -cyclobutyl | | —$CH_3$ | H | —Ph | 1 | 2 |
| -triazolyl | H | H | —$OCH_3$ | -cyclopentyl | | —$CH_3$ | H | —Ph | 1 | 2 |
| -triazolyl | H | H | —$OCH_3$ | -cyclohexyl | | —$CH_3$ | H | —Ph | 1 | 2 |
| -triazolyl | H | H | —$OCH_3$ | -cyclobutyl | | —$CH_3$ | H | —Ph | 1 | 3 |
| -triazolyl | H | H | —$OCH_3$ | -cyclopentyl | | —$CH_3$ | H | —Ph | 1 | 3 |
| -triazolyl | H | H | —$OCH_3$ | -cyclohexyl | | —$CH_3$ | H | —Ph | 1 | 3 |
| | 2-$OCH_2O$-3 | H | -triazolyl | -cyclobutyl | | —$CH_3$ | H | —Ph | 1 | 2 |
| | 2-$OCH_2O$-3 | H | -triazolyl | -cyclopentyl | | —$CH_3$ | H | —Ph | 1 | 2 |
| | 2-$OCH_2O$-3 | H | -triazolyl | -cyclohexyl | | —$CH_3$ | H | —Ph | 1 | 2 |
| | 2-$OCH_2O$-3 | H | -triazolyl | -cyclobutyl | | —$CH_3$ | H | —Ph | 1 | 3 |
| | 2-$OCH_2O$-3 | H | -triazolyl | -cyclopentyl | | —$CH_3$ | H | —Ph | 1 | 3 |
| | 2-$OCH_2O$-3 | H | -triazolyl | -cyclohexyl | | —$CH_3$ | H | —Ph | 1 | 3 |
| —$OCH_3$ | —$OCH_3$ | H | -triazolyl | -cyclobutyl | | —$CH_3$ | H | —Ph | 1 | 2 |
| —$OCH_3$ | —$OCH_3$ | H | -triazolyl | -cyclopentyl | | —$CH_3$ | H | —Ph | 1 | 2 |
| —$OCH_3$ | —$OCH_3$ | H | -triazolyl | -cyclohexyl | | —$CH_3$ | H | —Ph | 1 | 2 |
| —$OCH_3$ | —$OCH_3$ | H | -triazolyl | -cyclobutyl | | —$CH_3$ | H | —Ph | 1 | 3 |
| —$OCH_3$ | —$OCH_3$ | H | -triazolyl | -cyclopentyl | | —$CH_3$ | H | —Ph | 1 | 3 |
| —$OCH_3$ | —$OCH_3$ | H | -triazolyl | -cyclohexyl | | —$CH_3$ | H | —Ph | 1 | 3 |
| —$OCH_3$ | H | H | -triazolyl | -cyclobutyl | | —$CH_3$ | H | —Ph | 1 | 2 |
| —$OCH_3$ | H | H | -triazolyl | -cyclopentyl | | —$CH_3$ | H | —Ph | 1 | 2 |
| —$OCH_3$ | H | H | -triazolyl | -cyclohexyl | | —$CH_3$ | H | —Ph | 1 | 2 |
| —$OCH_3$ | H | H | -triazolyl | -cyclobutyl | | —$CH_3$ | H | —Ph | 1 | 3 |
| —$OCH_3$ | H | H | -triazolyl | -cyclopentyl | | —$CH_3$ | H | —Ph | 1 | 3 |
| —$OCH_3$ | H | H | -triazolyl | -cyclohexyl | | —$CH_3$ | H | —Ph | 1 | 3 |
| H | -triazolyl | —$OCH_3$ | H | -cyclobutyl | | —$CH_3$ | H | —Ph | 1 | 2 |
| H | -triazolyl | —$OCH_3$ | H | -cyclopentyl | | —$CH_3$ | H | —Ph | 1 | 2 |
| H | -triazolyl | —$OCH_3$ | H | -cyclohexyl | | —$CH_3$ | H | —Ph | 1 | 2 |
| H | -triazolyl | —$OCH_3$ | H | -cyclobutyl | | —$CH_3$ | H | —Ph | 1 | 3 |
| H | -triazolyl | —$OCH_3$ | H | -cyclopentyl | | —$CH_3$ | H | —Ph | 1 | 3 |
| H | -triazolyl | —$OCH_3$ | H | -cyclohexyl | | —$CH_3$ | H | —Ph | 1 | 3 |
| -triazolyl | H | H | H | -cyclobutyl | | —$CH_3$ | H | —Ph | 2 | 3 |
| -triazolyl | H | H | H | -cyclopentyl | | —$CH_3$ | H | —Ph | 2 | 3 |
| -triazolyl | H | H | H | -cyclohexyl | | —$CH_3$ | H | —Ph | 2 | 3 |
| H | -triazolyl | H | H | -cyclobutyl | | —$CH_3$ | H | —Ph | 2 | 3 |
| H | -triazolyl | H | H | -cyclopentyl | | —$CH_3$ | H | —Ph | 2 | 3 |
| H | -triazolyl | H | H | -cyclohexyl | | —$CH_3$ | H | —Ph | 2 | 3 |
| H | H | -triazolyl | H | -cyclobutyl | | —$CH_3$ | H | —Ph | 2 | 3 |
| H | H | -triazolyl | H | -cyclopentyl | | —$CH_3$ | H | —Ph | 2 | 3 |
| H | H | -triazolyl | H | -cyclohexyl | | —$CH_3$ | H | —Ph | 2 | 3 |
| -triazolyl | H | H | H | -cyclobutyl | | —$CH_3$ | H | —Ph | 2 | 2 |
| -triazolyl | H | H | H | -cyclopentyl | | —$CH_3$ | H | —Ph | 2 | 2 |
| -triazolyl | H | H | H | -cyclohexyl | | —$CH_3$ | H | —Ph | 2 | 2 |
| H | -triazolyl | H | H | -cyclobutyl | | —$CH_3$ | H | —Ph | 2 | 2 |
| H | -triazolyl | H | H | -cyclopentyl | | —$CH_3$ | H | —Ph | 2 | 2 |
| H | -triazolyl | H | H | -cyclohexyl | | —$CH_3$ | H | —Ph | 2 | 2 |
| H | H | -triazolyl | H | -cyclobutyl | | —$CH_3$ | H | —Ph | 2 | 2 |
| H | H | -triazolyl | H | -cyclopentyl | | —$CH_3$ | H | —Ph | 2 | 2 |
| H | H | -triazolyl | H | -cyclohexyl | | —$CH_3$ | H | —Ph | 2 | 2 |
| H | —$OCH_3$ | -triazolyl | H | -cyclobutyl | | —$CH_3$ | H | —Ph | 2 | 2 |
| H | —$OCH_3$ | -triazolyl | H | -cyclopentyl | | —$CH_3$ | H | —Ph | 2 | 2 |
| H | —$OCH_3$ | -triazolyl | H | -cyclohexyl | | —$CH_3$ | H | —Ph | 2 | 2 |
| H | —$OCH_3$ | -triazolyl | H | -cyclobutyl | | —$CH_3$ | H | —Ph | 2 | 3 |
| H | —$OCH_3$ | -triazolyl | H | -cyclopentyl | | —$CH_3$ | H | —Ph | 2 | 3 |
| H | —$OCH_3$ | -triazolyl | H | -cyclohexyl | | —$CH_3$ | H | —Ph | 2 | 3 |
| -triazolyl | H | H | —$OCH_3$ | -cyclobutyl | | —$CH_3$ | H | —Ph | 2 | 2 |
| -triazolyl | H | H | —$OCH_3$ | -cyclopentyl | | —$CH_3$ | H | —Ph | 2 | 2 |
| -triazolyl | H | H | —$OCH_3$ | -cyclohexyl | | —$CH_3$ | H | —Ph | 2 | 2 |

TABLE 1-continued

| Positions of $R_1$, $R_2$, $R_3$ on the phenyl nucleus | | | | | | | | | | |
|---|---|---|---|---|---|---|---|---|---|---|
| 2- | 3- | 4- | 5- | $R_4$ | $R_5$ | $R_6$ | Y | k | l | |
| -triazolyl | H | H | —OCH₃ | -cyclobutyl | —CH₃ | H | —Ph | 2 | 3 | |
| -triazolyl | H | H | —OCH₃ | -cyclopentyl | —CH₃ | H | —Ph | 2 | 3 | |
| -triazolyl | H | H | —OCH₃ | -cyclohexyl | —CH₃ | H | —Ph | 2 | 3 | |
| | 2-OCH₂O-3 | H | -triazolyl | -cyclobutyl | —CH₃ | H | —Ph | 2 | 2 | |
| | 2-OCH₂O-3 | H | -triazolyl | -cyclopentyl | —CH₃ | H | —Ph | 2 | 2 | |
| | 2-OCH₂O-3 | H | -triazolyl | -cyclohexyl | —CH₃ | H | —Ph | 2 | 2 | |
| | 2-OCH₂O-3 | H | -triazolyl | -cyclobutyl | —CH₃ | H | —Ph | 2 | 3 | |
| | 2-OCH₂O-3 | H | -triazolyl | -cyclopentyl | —CH₃ | H | —Ph | 2 | 3 | |
| | 2-OCH₂O-3 | H | -triazolyl | -cyclohexyl | —CH₃ | H | —Ph | 2 | 3 | |
| —OCH₃ | —OCH₃ | H | -triazolyl | -cyclobutyl | —CH₃ | H | —Ph | 2 | 2 | |
| —OCH₃ | —OCH₃ | H | -triazolyl | -cyclopentyl | —CH₃ | H | —Ph | 2 | 2 | |
| —OCH₃ | —OCH₃ | H | -triazolyl | -cyclohexyl | —CH₃ | H | —Ph | 2 | 2 | |
| —OCH₃ | —OCH₃ | H | -triazolyl | -cyclobutyl | —CH₃ | H | —Ph | 2 | 3 | |
| —OCH₃ | —OCH₃ | H | -triazolyl | -cyclopentyl | —CH₃ | H | —Ph | 2 | 3 | |
| —OCH₃ | —OCH₃ | H | -triazolyl | -cyclohexyl | —CH₃ | H | —Ph | 2 | 3 | |
| H | -pyrolyl | H | H | —(CH₂)₂CH₃ | —CH₃ | H | —Ph | 2 | 2 | |
| H | -pyrolyl | H | H | —(CH₂)₃CH₃ | —CH₃ | H | —Ph | 2 | 2 | |
| H | -pyrolyl | H | H | —(CH₂)₄CH₃ | —CH₃ | H | —Ph | 2 | 2 | |
| H | H | -pyrolyl | H | —(CH₂)₂CH₃ | —CH₃ | H | —Ph | 2 | 2 | |
| H | H | -pyrolyl | H | —(CH₂)₃CH₃ | —CH₃ | H | —Ph | 2 | 2 | |
| H | H | -pyrolyl | H | —(CH₂)₄CH₃ | —CH₃ | H | —Ph | 2 | 2 | |
| H | -pyrolyl | H | H | —(CH₂)₂CH₃ | —CH₃ | H | —Ph | 2 | 3 | |
| H | -pyrolyl | H | H | —(CH₂)₃CH₃ | —CH₃ | H | —Ph | 2 | 3 | |
| H | -pyrolyl | H | H | —(CH₂)₄CH₃ | —CH₃ | H | —Ph | 2 | 3 | |
| H | H | -pyrolyl | H | —(CH₂)₂CH₃ | —CH₃ | H | —Ph | 2 | 3 | |
| H | H | -pyrolyl | H | —(CH₂)₃CH₃ | —CH₃ | H | —Ph | 2 | 3 | |
| H | H | -pyrolyl | H | —(CH₂)₄CH₃ | —CH₃ | H | —Ph | 2 | 3 | |
| —OCH₃ | H | H | -pyrolyl | -cyclobutyl | —CH₃ | H | —Ph | 1 | 2 | |
| —OCH₃ | H | H | -pyrolyl | -cyclopentyl | —CH₃ | H | —Ph | 1 | 2 | |
| —OCH₃ | H | H | -pyrolyl | -cyclohexyl | —CH₃ | H | —Ph | 1 | 2 | |
| —OCH₃ | H | H | -pyrolyl | -cyclobutyl | —CH₃ | H | —Ph | 1 | 3 | |
| —OCH₃ | H | H | -pyrolyl | -cyclopentyl | —CH₃ | H | —Ph | 1 | 3 | |
| —OCH₃ | H | H | -pyrolyl | -cyclohexyl | —CH₃ | H | —Ph | 1 | 3 | |
| —OCH₃ | H | H | -pyrolyl | -cyclobutyl | —CH₃ | H | —Ph | 2 | 2 | |
| —OCH₃ | H | H | -pyrolyl | -cyclopentyl | —CH₃ | H | —Ph | 2 | 2 | |
| —OCH₃ | H | H | -pyrolyl | -cyclohexyl | —CH₃ | H | —Ph | 2 | 2 | |
| —OCH₃ | H | H | -pyrolyl | -cyclobutyl | —CH₃ | H | —Ph | 2 | 3 | |
| —OCH₃ | H | H | -pyrolyl | -cyclopentyl | —CH₃ | H | —Ph | 2 | 3 | |
| —OCH₃ | H | H | -pyrolyl | -cyclohexyl | —CH₃ | H | —Ph | 2 | 3 | |
| H | -pyrolyl | H | H | —(CH₂)₂CH₃ | —CH₃ | H | —Ph | 1 | 2 | |
| H | -pyrolyl | H | H | —(CH₂)₃CH₃ | —CH₃ | H | —Ph | 1 | 2 | |
| H | -pyrolyl | H | H | —(CH₂)₄CH₃ | —CH₃ | H | —Ph | 1 | 2 | |
| H | H | -pyrolyl | H | —(CH₂)₂CH₃ | —CH₃ | H | —Ph | 1 | 2 | |
| H | H | -pyrolyl | H | —(CH₂)₃CH₃ | —CH₃ | H | —Ph | 1 | 2 | |
| H | H | -pyrolyl | H | —(CH₂)₄CH₃ | —CH₃ | H | —Ph | 1 | 2 | |
| H | -pyrolyl | H | H | —(CH₂)₂CH₃ | —CH₃ | H | —Ph | 1 | 3 | |
| H | -pyrolyl | H | H | —(CH₂)₃CH₃ | —CH₃ | H | —Ph | 1 | 3 | |
| H | -pyrolyl | H | H | —(CH₂)₄CH₃ | —CH₃ | H | —Ph | 1 | 3 | |
| H | H | -pyrolyl | H | —(CH₂)₂CH₃ | —CH₃ | H | —Ph | 1 | 3 | |
| H | H | -pyrolyl | H | —(CH₂)₃CH₃ | —CH₃ | H | —Ph | 1 | 3 | |
| H | H | -pyrolyl | H | —(CH₂)₄CH₃ | —CH₃ | H | —Ph | 1 | 3 | |
| —OCH₃ | H | H | -triazolyl | -cyclobutyl | —CH₃ | H | —Ph | 2 | 2 | |
| —OCH₃ | H | H | -triazolyl | -cyclopentyl | —CH₃ | H | —Ph | 2 | 2 | |
| —OCH₃ | H | H | -triazolyl | -cyclohexyl | —CH₃ | H | —Ph | 2 | 2 | |
| —OCH₃ | H | H | -triazolyl | -cyclobutyl | —CH₃ | H | —Ph | 2 | 3 | |
| —OCH₃ | H | H | -triazolyl | -cyclopentyl | —CH₃ | H | —Ph | 2 | 3 | |
| —OCH₃ | H | H | -triazolyl | -cyclohexyl | —CH₃ | H | —Ph | 2 | 3 | |
| H | -triazolyl | —OCH₃ | H | -cyclobutyl | —CH₃ | H | —Ph | 2 | 2 | |
| H | -triazolyl | —OCH₃ | H | -cyclopentyl | —CH₃ | H | —Ph | 2 | 2 | |
| H | -triazolyl | —OCH₃ | H | -cyclohexyl | —CH₃ | H | —Ph | 2 | 2 | |
| H | -triazolyl | —OCH₃ | H | -cyclobutyl | —CH₃ | H | —Ph | 2 | 3 | |
| H | -triazolyl | —OCH₃ | H | -cyclopentyl | —CH₃ | H | —Ph | 2 | 3 | |
| H | -triazolyl | —OCH₃ | H | -cyclohexyl | —CH₃ | H | —Ph | 2 | 3 | |
| —OCH₃ | H | H | -pyrolyl | —(CH₂)₂CH₃ | —CH₃ | H | —Ph | 1 | 2 | |
| —OCH₃ | H | H | -pyrolyl | —(CH₂)₃CH₃ | —CH₃ | H | —Ph | 1 | 2 | |
| —OCH₃ | H | H | -pyrolyl | —(CH₂)₄CH₃ | —CH₃ | H | —Ph | 1 | 2 | |
| —OCH₃ | H | H | -pyrolyl | —(CH₂)₂CH₃ | —CH₃ | H | —Ph | 1 | 3 | |
| —OCH₃ | H | H | -pyrolyl | —(CH₂)₃CH₃ | —CH₃ | H | —Ph | 1 | 3 | |
| —OCH₃ | H | H | -pyrolyl | —(CH₂)₄CH₃ | —CH₃ | H | —Ph | 1 | 3 | |
| —OCH₃ | H | H | -pyrolyl | —(CH₂)₂CH₃ | —CH₃ | H | —Ph | 2 | 2 | |
| —OCH₃ | H | H | -pyrolyl | —(CH₂)₃CH₃ | —CH₃ | H | —Ph | 2 | 2 | |
| —OCH₃ | H | H | -pyrolyl | —(CH₂)₄CH₃ | —CH₃ | H | —Ph | 2 | 2 | |
| —OCH₃ | H | H | -pyrolyl | —(CH₂)₂CH₃ | —CH₃ | H | —Ph | 2 | 3 | |
| —OCH₃ | H | H | -pyrolyl | —(CH₂)₃CH₃ | —CH₃ | H | —Ph | 2 | 3 | |
| —OCH₃ | H | H | -pyrolyl | —(CH₂)₄CH₃ | —CH₃ | H | —Ph | 2 | 3 | |

TABLE 1-continued

| Positions of $R_1$, $R_2$, $R_3$ on the phenyl nucleus | | | | $R_4$ | $R_5$ | $R_6$ | Y | k | l |
|---|---|---|---|---|---|---|---|---|---|
| 2- | 3- | 4- | 5- | | | | | | |
| —O—CH$_2$-2-Py | H | H | H | —CH$_3$ | —CH$_3$ | H | —Ph | 1 | 3 |
| —O—CH$_2$-2-Py | H | H | H | —(CH$_2$)$_2$CH$_3$ | —CH$_3$ | H | —Ph | 1 | 3 |
| —O—CH$_2$-2-Py | H | H | H | —(CH$_2$)$_4$CH$_3$ | —CH$_3$ | H | —Ph | 1 | 3 |
| —O—CH$_2$-2-Py | H | H | H | —(CH$_2$)$_6$CH$_3$ | —CH$_3$ | H | —Ph | 1 | 3 |
| —O—CH$_2$-2-Py | H | H | H | -benzyl | —CH$_3$ | H | —Ph | 1 | 3 |
| —O—CH$_2$-2-Py | H | H | H | —(CH$_2$)$_2$—Ph | —CH$_3$ | H | —Ph | 1 | 3 |
| —O—CH$_2$-2-Py | H | H | H | —(CH$_2$)$_3$—Ph | —CH$_3$ | H | —Ph | 1 | 3 |
| —O—CH$_2$-2-Py | H | H | H | —CH$_3$ | —(CH$_2$)$_4$— | | —Ph | 1 | 3 |
| —O—CH$_2$-2-Py | H | H | H | —(CH$_2$)$_2$CH$_3$ | —(CH$_2$)$_4$— | | —Ph | 1 | 3 |
| —O—CH$_2$-2-Py | H | H | H | —(CH$_2$)$_4$CH$_3$ | —(CH$_2$)$_4$— | | —Ph | 1 | 3 |
| —O—CH$_2$-2-Py | H | H | H | —(CH$_2$)$_6$CH$_3$ | —(CH$_2$)$_4$— | | —Ph | 1 | 3 |
| —O—CH$_2$-2-Py | H | H | H | -benzyl | —(CH$_2$)$_4$— | | —Ph | 1 | 3 |
| —O—CH$_2$-2-Py | H | H | H | —(CH$_2$)$_3$—Ph | —(CH$_2$)$_4$— | | —Ph | 1 | 3 |
| —O—CH$_2$-2-Py | H | H | H | —(CH$_2$)$_3$—Ph | —(CH$_2$)$_4$— | | —Ph | 1 | 3 |
| —O—CH$_2$-2-Py | H | H | H | —(CH$_2$)$_2$CH$_3$ | —CH$_3$ | H | —Ph | 1 | 2 |
| —O—CH$_2$-2-Py | H | H | H | —(CH$_2$)$_4$CH$_3$ | —CH$_3$ | H | —Ph | 1 | 2 |
| —O—CH$_2$-2-Py | H | H | H | —(CH$_2$)$_2$CH$_3$ | —CH$_3$ | H | —Ph | 2 | 2 |
| —O—CH$_2$-2-Py | H | H | H | —(CH$_2$)$_4$CH$_3$ | —CH$_3$ | H | —Ph | 2 | 2 |
| —O—CH$_2$-2-Py | H | H | H | —(CH$_2$)$_2$CH$_3$ | —CH$_3$ | H | —Ph | 2 | 3 |
| —O—CH$_2$-2-Py | H | H | H | —(CH$_2$)$_4$CH$_3$ | —CH$_3$ | H | —Ph | 2 | 3 |
| —O—CH$_2$-2-Py | H | H | H | —(CH$_2$)$_2$CH$_3$ | —(CH$_2$)$_4$— | | —Ph | 1 | 3 |
| —O—CH$_2$-2-Py | H | H | H | —(CH$_2$)$_2$CH$_3$ | —(CH$_2$)$_4$— | | —Ph | 1 | 3 |
| —O-benzyl | H | H | H | —(CH$_2$)$_6$CH$_3$ | —(CH$_2$)$_4$— | | —Ph | 1 | 3 |
| —O-benzyl | H | H | H | —(CH$_2$)$_3$—Ph | —(CH$_2$)$_4$— | | —Ph | 1 | 3 |
| H | —O—CH$_2$-2-Py | H | H | —(CH$_2$)$_2$CH$_3$ | —CH$_3$ | H | —Ph | 1 | 3 |
| H | —O—CH$_2$-2-Py | H | H | —(CH$_2$)$_4$CH$_3$ | —CH$_3$ | H | —Ph | 1 | 3 |
| H | —O—CH$_2$-2-Py | H | H | —(CH$_2$)$_2$CH$_3$ | —CH$_3$ | H | —Ph | 1 | 2 |
| H | —O—CH$_2$-2-Py | H | H | —(CH$_2$)$_4$CH$_3$ | —CH$_3$ | H | —Ph | 1 | 2 |
| H | —O—CH$_2$-2-Py | H | H | —(CH$_2$)$_2$CH$_3$ | —CH$_3$ | H | —Ph | 2 | 2 |
| H | —O—CH$_2$-2-Py | H | H | —(CH$_2$)$_4$CH$_3$ | —CH$_3$ | H | —Ph | 2 | 2 |
| H | —O—CH$_2$-2-Py | H | H | —(CH$_2$)$_2$CH$_3$ | —CH$_3$ | H | —Ph | 2 | 3 |
| H | —O—CH$_2$-2-Py | H | H | —(CH$_2$)$_4$CH$_3$ | —CH$_3$ | H | —Ph | 2 | 3 |
| H | H | —O—CH$_2$-2-Py | H | —(CH$_2$)$_2$CH$_3$ | —CH$_3$ | H | —Ph | 1 | 3 |
| H | H | —O—CH$_2$-2-Py | H | —(CH$_2$)$_4$CH$_3$ | —CH$_3$ | H | —Ph | 1 | 3 |
| H | H | —O—CH$_2$-2-Py | H | —(CH$_2$)$_2$CH$_3$ | —CH$_3$ | H | —Ph | 1 | 2 |
| H | H | —O—CH$_2$-2-Py | H | —(CH$_2$)$_4$CH$_3$ | —CH$_3$ | H | —Ph | 1 | 2 |
| H | H | —O—CH$_2$-2-Py | H | —(CH$_2$)$_2$CH$_3$ | —CH$_3$ | H | —Ph | 2 | 2 |
| H | H | —O—CH$_2$-2-Py | H | —(CH$_2$)$_4$CH$_3$ | —CH$_3$ | H | —Ph | 2 | 2 |
| H | H | —O—CH$_2$-2-Py | H | —(CH$_2$)$_2$CH$_3$ | —CH$_3$ | H | —Ph | 2 | 3 |
| H | H | —O—CH$_2$-2-Py | H | —(CH$_2$)$_4$CH$_3$ | —CH$_3$ | H | —Ph | 2 | 3 |
| —O—CH$_2$-2-Py | —OCH$_3$ | H | H | —(CH$_2$)$_2$CH$_3$ | —CH$_3$ | H | —Ph | 1 | 3 |
| —O—CH$_2$-2-Py | —OCH$_3$ | H | H | —(CH$_2$)$_4$CH$_3$ | —CH$_3$ | H | —Ph | 1 | 3 |
| —O—CH$_2$-2-Py | —OCH$_3$ | H | H | —(CH$_2$)$_4$CH$_3$ | —CH$_3$ | H | —Ph | 2 | 3 |
| —O—CH$_2$-2-Py | —OCH$_3$ | H | H | —(CH$_2$)$_4$CH$_3$ | —(CH$_2$)$_4$— | | —Ph | 1 | 3 |
| —O—CH$_2$-2-Py | —OCH$_3$ | H | H | —(CH$_2$)$_6$CH$_3$ | —(CH$_2$)$_4$— | | —Ph | 2 | 3 |
| —O—CH$_2$-2-Py | H | —OCH$_3$ | H | —(CH$_2$)$_2$CH$_3$ | —CH$_3$ | H | —Ph | 1 | 3 |
| —O—CH$_2$-2-Py | H | —OCH$_3$ | H | —(CH$_2$)$_4$CH$_3$ | —CH$_3$ | H | —Ph | 1 | 3 |
| H | —O—CH$_2$-2-Py | —OCH$_3$ | H | —(CH$_2$)$_2$CH$_3$ | —CH$_3$ | H | —Ph | 1 | 3 |
| H | —O—CH$_2$-2-Py | —OCH$_3$ | H | —(CH$_2$)$_4$CH$_3$ | —CH$_3$ | H | —Ph | 1 | 3 |
| H | —OCH$_3$ | —O—CH$_2$-2-Py | H | —(CH$_2$)$_2$CH$_3$ | —CH$_3$ | H | —Ph | 1 | 3 |
| H | —OCH$_3$ | —O—CH$_2$-2-Py | H | —(CH$_2$)$_4$CH$_3$ | —CH$_3$ | H | —Ph | 1 | 3 |
| H | —OCH$_3$ | —O—CH$_2$-2-Py | H | —(CH$_2$)$_2$CH$_3$ | —CH$_3$ | H | —Ph | 1 | 2 |
| H | —OCH$_3$ | —O—CH$_2$-2-Py | H | —(CH$_2$)$_4$CH$_3$ | —CH$_3$ | H | —Ph | 1 | 2 |
| H | —OCH$_3$ | —O—CH$_2$-2-Py | H | —(CH$_2$)$_2$CH$_3$ | —CH$_3$ | H | —Ph | 2 | 2 |
| H | —OCH$_3$ | —O—CH$_2$-2-Py | H | —(CH$_2$)$_4$CH$_3$ | —CH$_3$ | H | —Ph | 2 | 2 |
| H | —OCH$_3$ | —O—CH$_2$-2-Py | H | —(CH$_2$)$_2$CH$_3$ | —CH$_3$ | H | —Ph | 2 | 3 |
| H | —OCH$_3$ | —O—CH$_2$-2-Py | H | —(CH$_2$)$_4$CH$_3$ | —CH$_3$ | H | —Ph | 2 | 3 |
| —O-CH$_2$-2-Py | H | H | -imidazolyl | —(CH$_2$)$_2$CH$_3$ | —CH$_3$ | H | —Ph | 1 | 3 |
| —O-CH$_2$-2-Py | H | H | -imidazolyl | —(CH$_2$)$_4$CH$_3$ | —CH$_3$ | H | —Ph | 1 | 3 |
| —O-CH$_2$-2-Py | H | H | -imidazolyl | —(CH$_2$)$_2$CH$_3$ | —CH$_3$ | H | —Ph | 1 | 2 |
| —O-CH$_2$-2-Py | H | H | -imidazolyl | —(CH$_2$)$_4$CH$_3$ | —CH$_3$ | H | —Ph | 1 | 2 |
| —O-CH$_2$-2-Py | H | H | -imidazolyl | —(CH$_2$)$_2$CH$_3$ | —CH$_3$ | H | —Ph | 2 | 2 |
| —O-CH$_2$-2-Py | H | H | -imidazolyl | —(CH$_2$)$_4$CH$_3$ | —CH$_3$ | H | —Ph | 2 | 2 |
| —O-CH$_2$-2-Py | H | H | -imidazolyl | —(CH$_2$)$_2$CH$_3$ | —CH$_3$ | H | —Ph | 2 | 3 |
| —O-CH$_2$-2-Py | H | H | -imidazolyl | —(CH$_2$)$_4$CH$_3$ | —CH$_3$ | H | —Ph | 2 | 3 |
| —OCH$_3$ | H | H | -imidazolyl | —CH$_2$CH$_3$ | —CH$_3$ | H | —CH$_3$ | 1 | 3 |
| —OCH$_3$ | H | H | -imidazolyl | —(CH$_2$)$_4$CH$_3$ | —CH$_3$ | H | —CH$_3$ | 1 | 3 |
| —OCH$_3$ | H | H | -imidazolyl | —CH$_2$CH$_3$ | —CH$_3$ | H | -2-Py | 1 | 3 |
| —OCH$_3$ | H | H | -imidazolyl | —(CH$_2$)$_4$CH$_3$ | —CH$_3$ | H | -2-Py | 1 | 3 |
| —OCH$_3$ | H | H | -imidazolyl | —CH$_2$CH$_3$ | —CH$_3$ | H | -2-Py | 2 | 3 |
| —OCH$_3$ | H | H | -imidazolyl | —(CH$_2$)$_4$CH$_3$ | —CH$_3$ | H | -2-Py | 2 | 3 |
| —OCH$_3$ | H | H | -imidazolyl | —CH$_2$CH$_3$ | —CH$_3$ | H | -pyrimidyl | 1 | 3 |
| —OCH$_3$ | H | H | -imidazolyl | —(CH$_2$)$_4$CH$_3$ | —CH$_3$ | H | -pyrimidyl | 1 | 3 |
| —OCH$_3$ | H | H | -imidazolyl | —CH$_2$CH$_3$ | —CH$_3$ | H | -pyrimidyl | 2 | 3 |
| —OCH$_3$ | H | H | -imidazolyl | —(CH$_2$)$_4$CH$_3$ | —CH$_3$ | H | -pyrimidyl | 2 | 3 |

TABLE 1-continued

| Positions of $R_1$, $R_2$, $R_3$ on the phenyl nucleus | | | | | | | | | |
|---|---|---|---|---|---|---|---|---|---|
| 2- | 3- | 4- | 5- | $R_4$ | $R_5$ | $R_6$ | Y | k | l |
| —OH | —OCH$_3$ | H | H | —(CH$_2$)$_2$CH$_3$ | —CH$_3$ | H | —Ph | 1 | 3 |
| —OH | —OCH$_3$ | H | H | —(CH$_2$)$_4$CH$_3$ | —CH$_3$ | H | —Ph | 1 | 3 |
| —OH | —OCH$_3$ | H | H | —(CH$_2$)$_4$CH$_3$ | —CH$_3$ | H | —Ph | 2 | 3 |
| —OH | —OCH$_3$ | H | H | —(CH$_2$)$_4$CH$_3$ | —(CH$_2$)$_4$— | | —Ph | 1 | 3 |
| —OH | —OCH$_3$ | H | H | —(CH$_2$)$_6$CH$_3$ | —(CH$_2$)$_4$— | | —Ph | 2 | 3 |

Among the compounds mentioned above, preferred compounds are those where $R_1$, $R_2$, and $R_3$ are independently hydrogen atom, methoxy group, imidazolyl group, pyrazolyl group, or triazolyl group; $R_4$ is n-propyl group, isopropyl group, n-butyl group, isobutyl group, sec-butyl group, t-butyl group, n-pentyl group, isopentyl group, sec-pentyl group, t-pentyl group, neopentyl group, cyclopropyl group, cyclobutyl group, or cyclopentyl group; $R_5$ is methyl group; $R_6$ is hydrogen atom; Y is phenyl group; k is 1 or 2; and l is 2 or 3. As for salts of the compounds of the present invention, hydrochlorides, sulfates, succinates, tartarates, and methanesulfonates are preferred.

Preparation methods of the compounds of the present invention will be explained below.

<Preparation Method A>

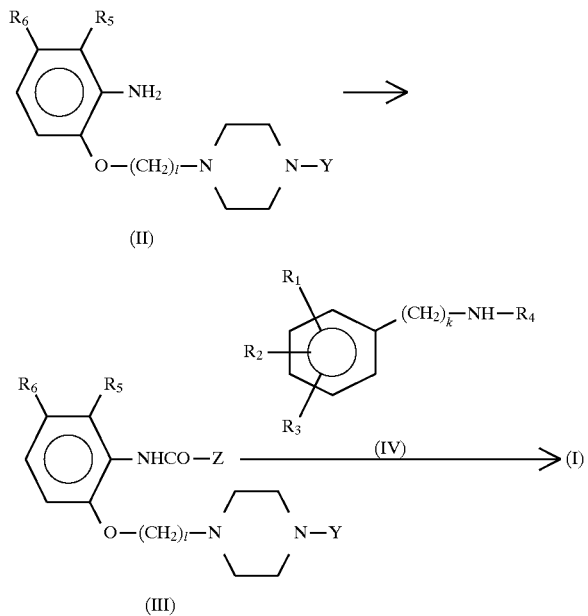

(In the scheme, $R_1$, $R_2$, $R_3$, $R_4$, $R_5$, $R_6$, k, l, and Y are the same as those defined in the above formula (I), and Z represents leaving groups such as a halogen atom, aryloxy group, or alkyloxy group.)

The compound (I) of the present invention can be obtained by converting the aniline derivative (II) to the reactive intermediate (III) and then reacting the intermediate (III) with the amine derivative (IV). Examples of the above reactive intermediates (III) include, for example, carbamoyl chlorides (symbol "Z" in the scheme is a chlorine atom) obtained by reacting the aniline derivative (II) with phosgene, trichloromethyl chloroformate, bis (trichloromethyl) carbonate or the like, and carbamoylaryl esters or carbamoylalkyl esters (symbol "Z" in the scheme is an aryloxy group or an alkyloxy group) obtained by reacting the aniline derivative (II) with aryl chloroformate or alkyl chloroformate. Solvents used for the preparation of the reactive intermediate (III) are not particularly limited so far as they are inert in the reaction. Examples of the solvent include, for example, benzene, toluene, hexane, heptane, diethyl ether, tetrahydrofuran, dioxane, ethyl acetate, methylene chloride, chloroform, 1,2-dichloroethane. The reaction may be efficiently carried out in the presence of an inert organic amine such as triethylamine, pyridine, or 1,8-diazabicyclo[5.4.0.]undec-7-en (DBU), or an inorganic base such as sodium hydrogen carbonate, potassium carbonate, or sodium carbonate. The reaction temperature may be from −15° C. to the boiling point of the solvent used.

The reactive intermediate (III) can be reacted, without isolation, with the amine derivative (IV) to give the compound (I) of the present invention. This reaction can also be efficiently carried out in the presence of an inert organic amine such as triethylamine, pyridine, or 1,8-diazabicyclo [5.4.0.]undec-7-en (DBU), or an inorganic base such as sodium hydrogen carbonate, potassium carbonate, or sodium carbonate. The reaction temperature may be from −15° C. to the boiling point of the solvent used.

<Preparation Method B> where $R_3$ is pyridylmethyloxy group.

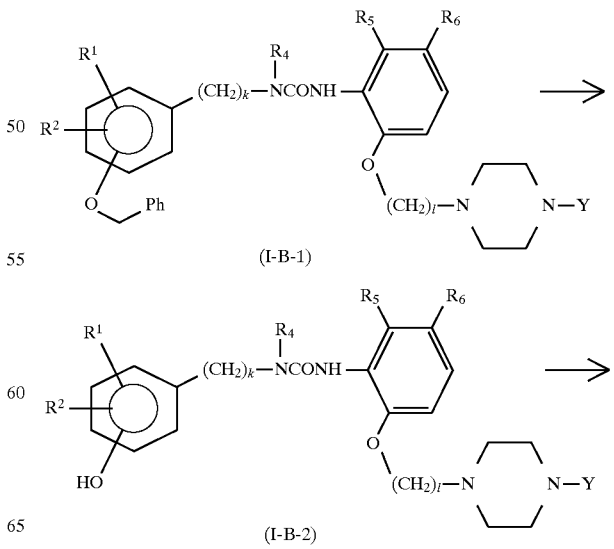

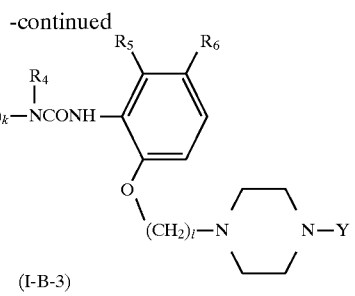

(I-B-3)

(In the scheme, $R_1$, $R_2$, $R_4$, $R_5$, $R_6$, k, l and Y are the same as those defined in the formula (I) and Py represents pyridyl group.)

The urea derivative (I-B-1) (the compounds of the formula (I) wherein $R_3$ is benzyloxy group) obtained according to method A is converted to the phenol derivative (I-B-2) through hydrogenolysis or the like in the presence of Pd/carbon catalyst, and then the phenol derivative is reacted with, for example, a chloromethylpyridine hydrochloride in the presence of a base to give the compounds of the present invention (I-B-3). Solvents used for the preparation of the compounds of the present invention (I-B-3) from the phenol derivative (I-B-2) are not particularly limited so far as they are inert in the reaction. Examples include benzene, toluene, hexane, heptane, diethyl ether, tetrahydrofuran, dioxane, ethyl acetate, methylene chloride, chloroform, 1,2-dichloroethane, N,N-dimethylformamide, dimethyl sulfoxide, N-methylpyrrolidone or the like. Examples of the base include, for example, inert organic amines such as triethylamine, pyridine, or 1,8-diazabicyclo[5.4.0.]undec-7-en (DBU), or inorganic bases such as sodium hydrogen carbonate, potassium carbonate, or sodium carbonate.

The above-mentioned amine derivative (IV) can also be prepared by the method set out below.

<Preparation Method C>

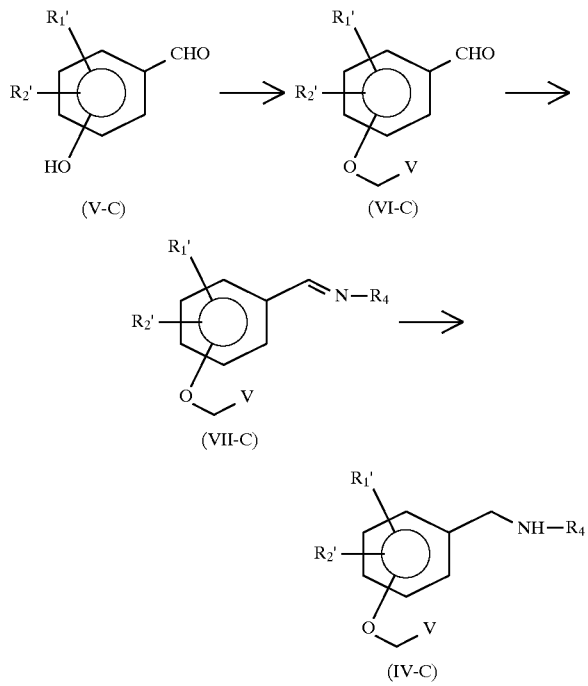

(In the scheme, $R_1'$ and $R_2'$ represent independently hydrogen atom or a $C_1$–$C_3$ alkoxy group, or alternatively, $R_1'$ and $R_2'$ form together to represent —O—$(CH_2)_n$—O— wherein n represents an integer of 1 to 3; V represents phenyl group or pyridyl group; and $R_4$ is the same as that defined in the formula (I).)

The benzaldehyde derivative (VI-C) can be obtained by reacting, in the presence of a base, the hydroxybenzaldehyde derivative (V-C) with benzyl chloride, benzyl bromide or the like where V is phenyl group, and by reacting with chloromethylpyridine hydrochloride or the like where V is pyridyl group. Solvents used for the reaction are not particularly limited so far as they are inert in the reaction, and examples include benzene, toluene, tetrahydrofuran, dioxane, chloroform, acetone, N,N-dimethylformamide, dimethyl sulfoxide, and N-methylpyrrolidone. Examples of the base include, for example, inert organic amines such as triethylamine, pyridine, or 1,8-diazabicyclo[5.4.0.]undec-7-en (DBU), or inorganic bases such as sodium hydrogen carbonate, potassium carbonate, and sodium carbonate. The reaction temperature may be from 10° C. to the boiling point of the solvent used, and the reaction time may be from 1 to 20 hours.

The resulting benzaldehyde derivative (VI-C) can then be reacted with $R_4$—$NH_2$ ($R_4$ is the same as that defined in the formula (I)) in an alcoholic solvent such as methyl alcohol, ethyl alcohol, or isopropyl alcohol for 1 to 24 hours at a reaction temperature of –10° C. to the boiling temperature of the solvent to give the imine derivative (VII-C), and the crude product without isolation can be subjected to reduction using a reducing agent such as sodium borohydride to give the amine derivative (IV-C). The reaction temperature may be from –10° C. to the boiling point of the solvent used, and the reaction time may be from 1 to 10 hours.

<Preparation Method D>

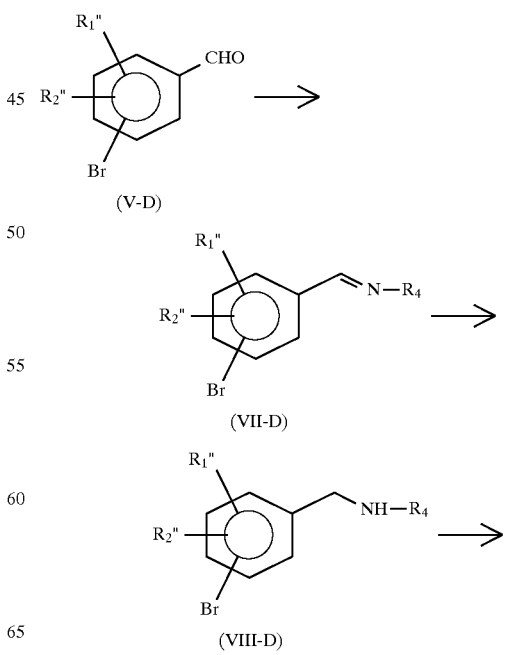

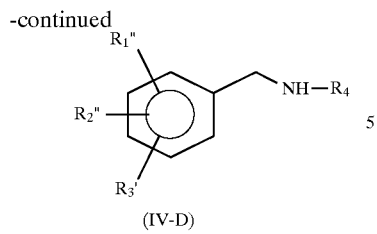

(IV-D)

(In the scheme, $R_1''$ and $R_2''$ represent independently hydrogen atom, a $C_1$–$C_3$ alkoxy group, Het-$(CH_2)_m$—O— (Het and m are the same as those defined above), or a $C_7$–$C_9$ aralkyloxy group, or alternatively, $R_1''$ and $R_2''$ may form together to represent —O—$(CH_2)_n$—O— (n represents an integer of 1 to 3); $R_2'$ represents a heterocyclic group containing from 1 to 4 nitrogen atoms and having 5 or 6 ring-membered atoms; and $R_4$ is the same as that defined in the formula (I).)

The bromobenzaldehyde derivative (V-D) can be reacted with $R_4$—$NH_2$ ($R_4$ is the same as that defined in the formula (I)) in alcoholic solvents such as methyl alcohol, ethyl alcohol, or isopropyl alcohol for 1 to 24 hours at a reaction temperature of −10° C. to the boiling temperature of the solvent used to give the imine derivative (VII-D), and the crude product without isolation can be subjected to reduction using a reducing agent such as sodium borohydride to give the bromobenzylamine derivative (VIII-D). The reaction temperature may be from −10° C. to the boiling point of the solvent used, and the reaction time may be from 1 to 10 hours. The bromobenzylamine derivative (VIII-D) can then be reacted with a heterocyclic compound containing from 1 to 4 nitrogen atoms and having 5 or 6 ring-membered atoms to give the amine derivative (IV-D) according to the coupling reaction of nitrogen-containing heterocyclic compounds using a copper catalyst (Young, S. Lo et al., Journal of Medicinal Chemistry, 1992, vol. 35, No. 26, pp.4790–4794).

<Preparation Method E>

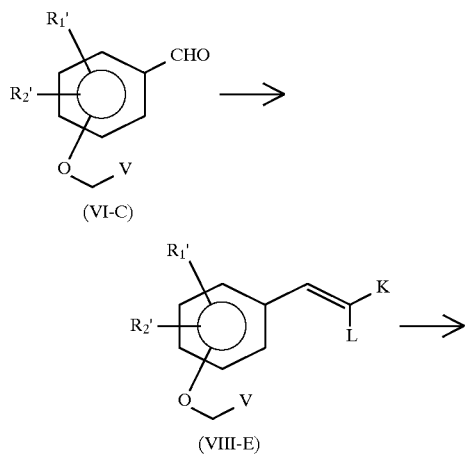

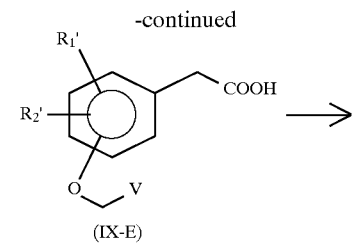

(IX-E)

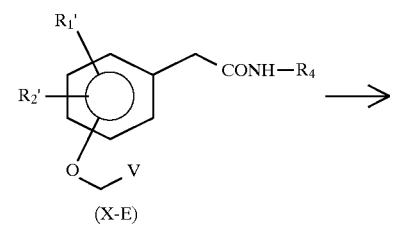

(X-E)

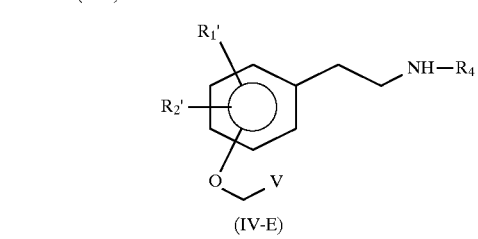

(IV-E)

(In the scheme, $R_1'$ and $R_2'$ represent independently hydrogen atom or a $C_1$–$C_3$ alkoxy group, or $R_1'$ and $R_2'$ may form together to represent —O—$(CH_2)_n$—O— (n represents an integer of 1 to 3); V represents phenyl group or pyridyl group; K represents chlorine atom, bromine atom, or methylthio group; L represents chlorine atom, bromine atom, or methylsulphinyl group; and $R_4$ is the same as that defined in the formula (I).)

The phenylacetic acid derivative (IX-E) can be readily synthesized according to a general method to prepare phenylacetic acid from the benzaldehyde derivative (VI-C) obtained by the preparation method B. For example, the target compound can be obtained by introducing dihalomethylene group by the Wittig reaction (described in "Shin Jikken Kagaku Kohza," Vol. 14, Syntheses and Reactions of Organic Compounds (II), Japan Chemical Society Ed., Maruzen, 1977, p.971), followed by hydrolysing the resulting compound (where K and L are chlorine atoms or bromine atoms). The target compound can also be prepared according to the method described in "Kagaku Sosetsu," No. 19, New Organic Synthetic Reactions, 1978, p.75 or "Yukigosei Kyokai-shi," 37, p.903, 1979, which includes the condensation reaction with methylthiomethyl sulfoxide (FAMSO) in the presence of benzyltrimethylammonium hydroxide (Triton B) (K is methylthio group and L is methylsulfinyl group in the scheme) and then acidic hydrolysis of the resulting compound.

The amide derivative (X-E) can be prepared by a general method, i.e., condensation of the phenylacetic acid derivative (IX-E) with $R_4$—$NH_2$ ($R_4$ is the same as that defined in the above formula (I)) using a condensation agent such as dicyclohexylcarbodiimide (DCC), or alternatively, reaction of $R_4NH_2$ with an acid chloride or mixed acid anhydride which is converted from the phenylacetic acid derivative (IX-E). The amine derivative (IV-E) can be obtained by reduction using sodium borohydride and boron trifluoride ether complex in tetrahydrofuran or dioxane as a solvent. These reactions can be carried out, for example, according to the method described by H. C. Brown and P. Heim et al., Journal of Organic Chemistry, 38, p.912, 1973. The amine derivative can also be obtained by reduction using sodium borohydride and acetic acid in tetrahydrofuran or dioxane as a solvent. These reactions can be carried out, for example, by the method of N. Umino et al. (Tetrahedron Letter, p.763, 1976).

<Preparation Method F>

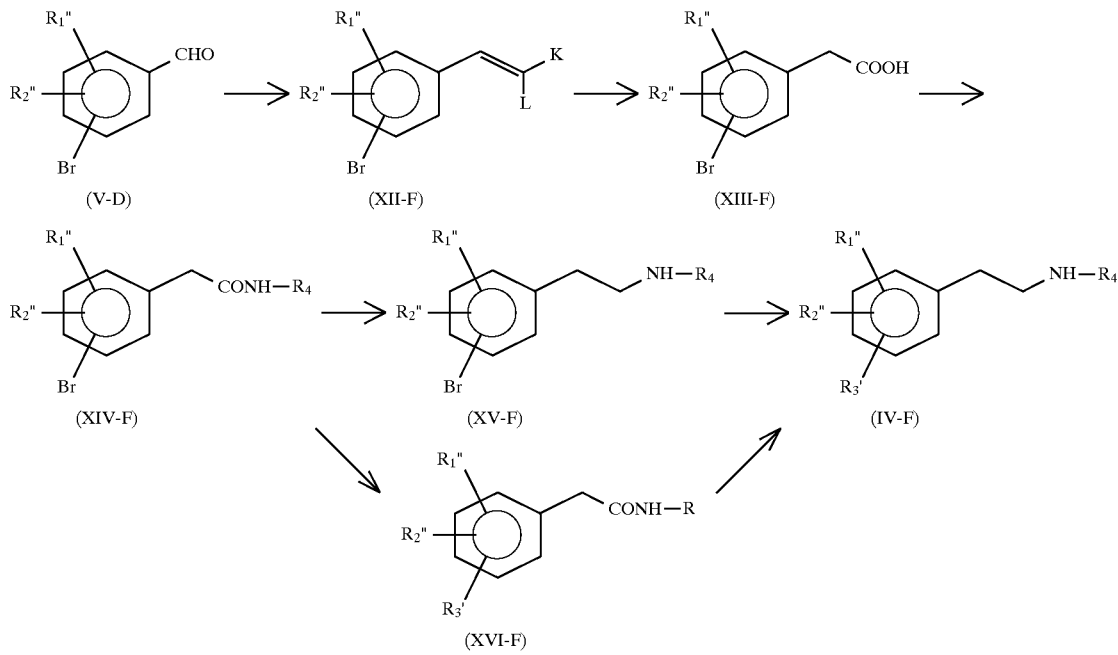

(In the scheme, $R_1''$ and $R_2''$ represent independently hydrogen atom, a $C_1$–$C_3$ alkoxy group, Het-$(CH_2)_m$—O— (Het and m are the same as those defined above) or a $C_7$–$C_9$ aralkyloxy group, or $R_1''$ and $R_2''$ may form together to represent —O—$(CH_2)_n$—O— (n represents an integer of from 1 to 3); K represents chlorine atom, bromine atom, or methylthio group; L represents chlorine atom, bromine atom, or methylsulfinyl group; $R_3'$ represents a heterocyclic group containing from 1 to 4 nitrogen atoms and having 5 or 6 ring-membered atoms; and $R_4$ is the same as that defined in the formula (I).)

The amine derivative (IV-F) can be prepared by converting the bromobenzaldehyde derivative (V-D) to the bromophenethylamine derivative (XV-F) by according to the preparation method E, followed by carrying out the coupling reaction with a nitrogen-containing heterocyclic compound according to the preparation method D. Alternatively, the amine derivative can be also obtained by converting the bromobenzaldehyde derivative (V-D) to the bromoamide derivative (XIV-F) according to the preparation method E, followed by carrying out the coupling reaction with a nitrogen-containing heterocyclic compound according to the preparation method D, and then reducing the amide according to the preparation method E.

<Preparation Method G>

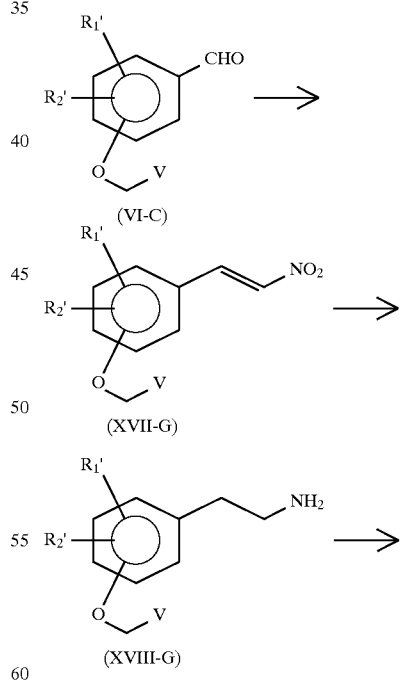

-continued

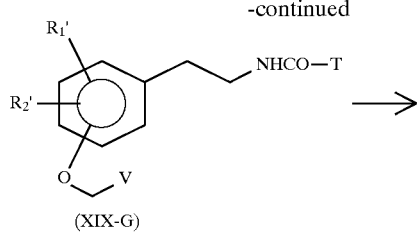

(XIX-G)

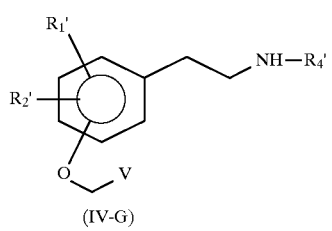

(IV-G)

(In the scheme, $R_1'$ and $R_2'$ represent independently hydrogen atom or a $C_1$–$C_3$ alkoxy group, or $R_1'$ and $R_2'$ may form together to represent —O—$(CH_2)_n$—O— (n represents an integer of 1 to 3); T represents hydrogen atom, a $C_1$–$C_6$ alkyl group or Ar—$(CH_2)_{p'}$— (Ar represents a $C_6$–$C_{10}$ aryl group and p' represents an integer of 0 to 2); $R_4'$ represents a $C_1$–$C_7$ alkyl group or Ar—$(CH_2)_p$— (Ar represents a $C_6$–$C_{10}$ aryl group and p represents an integer of 1 to 3); and V represents phenyl group or pyridyl group.)

The nitrostyrene derivative (XVII-G) can be obtained by reacting the benzaldehyde derivative (VI-C) with nitromethane or the like in the presence of ammonium acetate in a solvent such as toluene. Reduction of the nitrostyrene derivative (XVII-G) using LiAlH$_4$ or the like in tetrahydrofuran or ether can give the phenethylamine derivative (XVIII-G). These reactions can be carried out, for example, according to the method of Macor J E et al. described in Journal of Medicinal Chemistry, vol. 35, No. 20, pp.3625–3632, 1992. The phenethylamine derivative (XVIII-G) can then be converted to the amide derivative (XIX-G) by a conventional method using T-COCl or T-COOH (T is the same as that defined above), and followed by reduction reaction according to the preparation method E to give the amine derivative (IV-G).

The above aniline derivative (II) can be prepared by the method set out below.

<Preparation Method H>

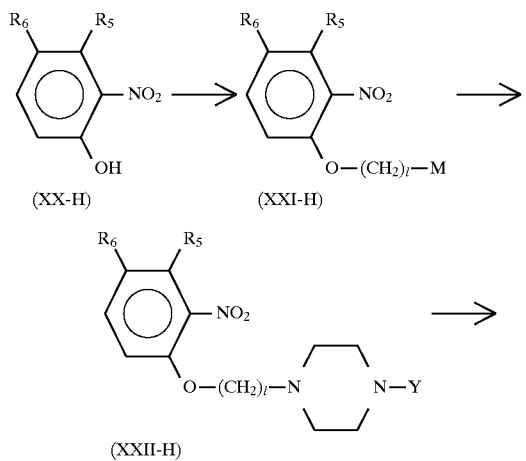

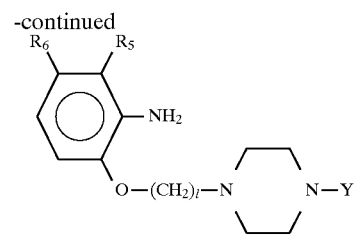

(II-H)

(In the scheme, $R_5$, $R_6$, l, and Y are the same as those defined in the above formula (I); and M represents chlorine atom or bromine atom.)

The nitrobenzene derivative (XXI-H) can be obtained by reacting the nitrophenol derivative (XX-H) with Br(CH$_2$)$_l$Cl, Br(CH$_2$)$_l$Br, or Cl(CH$_2$)$_l$Cl (l is the same as that defined above) in the presence of a base. Solvents used for the reaction are not particularly limited so far as they are inert in the reaction, and examples include benzene, toluene, tetrahydrofuran, dioxane, chloroform, acetone, N,N-dimethylformamide, dimethyl sulfoxide, or N-methylpyrrolidone. Examples of the base include, for example, inert organic amines such as triethylamine, pyridine, or 1,8-diazabicyclo[5.4.0.]undec-7-en (DBU), or inorganic bases such as sodium hydrogen carbonate, potassium carbonate, or sodium carbonate. The reaction temperature may be from 20° C. to the boiling point of the solvent, and the reaction time may be from 1 to 20 hours. Then, the product can be converted to the compound (XXII-H) by reacting with a piperazine derivative under similar conditions to those described above, and the resulting compound can be reduced by a conventional method for reducing nitro group to give the aniline derivative (II-H), e.g. catalytic hydrogenation in the presence of Pd/carbon catalyst in alcoholic solvents, or reduction with iron-acetic acid in an alcohol-water as a solvent.

These reactions can also be carried out according to the methods described by Teiji Kimua, Yasutake Takase et al., Journal of Medicinal Chemistry, vol. 11, No. 36, pp.1630–1640, 1993 and Teiji Kimura, Nobuhisa Watanabe et al., Journal of Medicinal Chemistry, vol. 35, No. 26, pp.1641–1653, 1993. Among the nitrophenol derivatives (XX-H), compounds wherein $R_6$ is hydrogen atom and $R_5$ is a $C_1$–$C_3$ alkyl group are known, per se, or can be readily obtained or manufactured according to known methods (Bulletin of the Chemical Society of Japan, vol. 50(1), pp.276–279, 1977).

Among the nitrophenol derivatives (XX-H), compounds (XX-H-1) wherein $R_5$ and $R_6$ form together to represent —(CH$_2$)$_4$— can be prepared according to the method set out below, i.e., by nitrating the phenol derivative (XXIII-H) using 60% nitric acid in a solvent such as ether for 0.5 to 5 hours at a reaction temperature of from −10° C. to the boiling point of the solvent, and then removing the isomer (XX-H-2) using silica gel chromatography.

<Preparation Method I>

(XXIII-H)

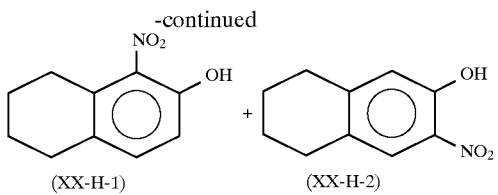

The compounds of the present invention have potent inhibitory activity against ACAT as shown in the following examples in the specification. Therefore, they are expected to be used as a medicine for preventive and/or therapeutic treatment of hyperlipemia, and as a medicine for preventive and/or therapeutic treatment of atherosclerosis.

When the compounds of the present invention are used as preventive and/or therapeutic medicines, the compounds alone or pharmaceutical compositions prepared in combination with a pharmaceutically acceptable carriers may be administered. The components or the compositions may be chosen depending on solubility and chemical properties of the compounds, routes of administration, protocols for administration and the like. For example, pharmaceutical compositions in the forms of, for example, granules, subtilized granules, powders, tablets, hard syrups, soft capsules, syrups, emulsions, suspensions, liposome-encupsulated formulations, or liquids may be prepared and applied to oral administrations, or alternatively, pharmaceutical compositions in the forms of, for example, injections, drips, rectal formulations (suppositories), transdermal formulations, transmucosal formulations, inhalants, ear drops, or nasal drops may be prepared and applied to parenteral administrations.

Examples of the excipients used for the preparation of solid formulations include, for example, lactose, sucrose, starch, talc, cellulose, dextrin, kaolin, calcium carbonate and the like. Liquid formulations for oral administration, e.g., emulsions, syrups, suspensions, and liquids, may contain commonly used inert diluents such as water and vegetable oils. These formulations may also contain, in addition to the inert diluents, various additives such as, for example, lubricants, suspension aids, sweeteners, flavoring agents, colorants, and preservatives. Liquid formulations may be prepared and encapsulated in capsules of absorbable material such as gelatin. Solvents or suspension medium used for the preparation of the formulations for parenteral administration, i.e., injections, may be, for example, water, propylene glycol, polyethylene glycol, benzyl alcohol, oleic acid esters, lecithines and the like. Injections in the form of powder such as lyophilized formulations may be subjected to distribution, and dissolved and formulated before administration by adding appropriate solvent. In addition, organic or inorganic carriers in the form of liquid or solid may be used in combination with the compounds of the present invention which are pharmaceutically acceptable and are suitable for oral, rectal, parenteral, and topical administrations. Pharmaceutical formulations can be prepared by ordinarily used method.

Clinical dose may generally be in the range of 1 to 1,000 mg, preferably 10 to 600 mg per day, as being the weight of the compound of the present invention, for oral administrations for adult. However, it is preferable that the dose may appropriately chosen depending on the age, conditions, and symptoms of the patients, and the use or non-use of co-administered drugs. The daily dose may be administered once in a day, or alternatively, 2 or 3 times a day with adequate intervals. The administration may be carried out intermittently with suspension for 1 to several day. In the case of injection, the dose may be 0.1 to 500 mg, preferably 0.5 to 100 mg per day for adults as being the weight of the compound of the present invention.

EXAMPLES

The present invention will be explained more specifically by examples. However, the scope of the present invention is not limited to these examples.

Reference Example 1

(Preparation Method C)

Synthesis of N-heptyl-(2-benzyloxy-3-methoxyphenyl)methylamine

Ethyl alcohol (30 ml) and n-heptylamine (5.23 g, 45.4 mmol) were added to 2-benzyloxy-3-methoxybenzaldehyde (10 g, 41.3 mmol), and the mixture was heated with stirring under reflux for 2 hours. The reaction mixture was cooled to 5° C., added with sodium borohydride (2.34 g, 61.9 mmol), and then stirred at room temperature for 10 hours. The reaction mixture was added with water (10 ml) and aqueous 6N hydrochloric acid to decompose excess sodium borohydride, and then made alkaline with 25% aqueous sodium hydroxide and extracted with toluene. After the extract was washed with saturated brine and dried over anhydrous sodium sulfate, the solvent was evaporated to give N-heptyl-(2-benzyloxy-3-methoxyphenyl)methylamine (13.5 g) as oil.

$^1$HNMR(CDCl$_3$): δ=0.86 (t, 3H), 1.24(m, 8H), 1.41(t, 2H), 1.58(bs, 1H), 2.49(t, 2H), 3.69(s, 2H), 3.90(s, 3H), 6.85–6.89(m, 2H), 7.03(t, 1H), 7.32–7.47(m, 5H)

The amine derivatives set out below (VI-C) were synthesized in the same manner as those described in Reference Example 1.

N-heptyl-[2-(2-pyridylmethyloxy)phenyl]methylamine
N-(3-phenylpropyl)-[2-(2-pyridylmethyloxy)phenyl]methylamine
N-(3-phenylpropyl)-(2-benzyloxy-3-methoxyphenyl)methylamine
N-propyl-[2-(2-pyridylmethyloxy)phenyl]methylamine
N-propyl-[2-(3-pyridylmethyloxy)phenyl]methylamine
N-propyl-[2-(4-pyridylmethyloxy)phenyl]methylamine
N-methyl-[2-(2-pyridylmethyloxy)phenyl]methylamine
N-pentyl-[2-(2-pyridylmethyloxy)phenyl]methylamine
N-pentyl-[3-(2-pyridylmethyloxy)phenyl]methylamine
N-pentyl-[4-(2-pyridylmethyloxy)phenyl]methylamine
N-pentyl-[2-(2-pyridylmethyloxy)-3-methoxyphenyl]methylamine
N-pentyl-[2-(2-pyridylmethyloxy)-4-methoxyphenyl]methylamine
N-pentyl-[3-(2-pyridylmethyloxy)-4-methoxyphenyl]methylamine
N-pentyl-[4-(2-pyridylmethyloxy)-3-methoxyphenyl]methylamine
N-cyclopentyl-(5-imidazolyl-2-methoxyphenyl)methylamine
N-isobutyl-(5-imidazolyl-2-methoxyphenyl)methylamine
N-isopropyl-(5-imidazolyl-2-methoxyphenyl)methylamine
N-tert-butyl-(5-imidazolyl-2-methoxyphenyl)methylamine Reference Example 2

(Preparation Method D)

Synthesis of N-pentyl-(5-imidazolyl-2-methoxyphenyl)methylamine

Ethyl alcohol (150 ml) and n-pentylamine (12.7 g, 0.146 mol) were added to 5-bromo-2-methoxybenzaldehyde (30.0 g, 0.14 mol), and the mixture was stirred at room temperature for 2 hours. The reaction mixture was cooled to 5° C., added with sodium borohydride (7.9 g, 0.209 mol), and then stirred at room temperature for 8 hours. The reaction mixture was added with water (50 ml) and aqueous 6N hydrochloric acid to decompose excess sodium borohydride, made alkaline with 25% aqueous sodium hydroxide, and extracted with toluene. The extract was washed with saturated brine and dried over anhydrous sodium sulfate, and then, the solvent was evaporated to give N-pentyl-(5-bromo-2-methoxyphenyl) methylamine (38.0 g).

$^1$HNMR(CDCl$_3$): δ=0.89(t, 3H), 1.30(m, 4 H), 1.48(t, 2H), 1.61(bs, 1H), 2.58(t,2H), 3.73(s, 2H), 3.81(s, 3H), 6.72(d, 1H), 7.29–7.37(m, 2H)

Imidazole (11.8 g, 0.173 mol), potassium carbonate (0.147 mol), cuprous chloride (1.4 g, 0.014 mol), and N-methylpyrrolidone (270 ml) were added to N-pentyl-(5-bromo-2-methoxyphenyl) methylamine (38.0 g, 0.133 mol), and then the mixture was heated with stirring at 178°–182° C. for 7 hours. The reaction mixture was cooled and added with ethyl acetate (200 ml), and then, inorganic salts and the like were removed by filtration and the solvent was evaporated. The residue was extracted with ethyl acetate, and the extract was washed with 10% aqueous ammonia and then with saturated brine. After dryness over anhydrous sodium sulfate, the solvent was evaporated. The residue was purified by silica gel chromatography (Wako Gell C-300: 360 g, eluent: methyl alcohol/ethyl acetate=1/10 to 1/3) to give N-pentyl-(5-imidazolyl-2-methoxyphenyl)methylamine (21.3 g) as oil.

$^1$HNMR(CDCl$_3$): δ=0.90(t, 3H), 1.32(m, 4H), 1.53(m, 2H), 1.77(bs, 1H), 2.63(t, 2H), 3.82(s, 2H), 3.89(s, 3H), 6.92(d, 1H), 7.18– 7.33(t, 4H), 7.77(s, 1H)

The amine derivatives set out below (VI-D) were synthesized in the same manners as those described in Reference Example 2.
N-pentyl-(2-imidazolylphenyl)methylamine
N-pentyl-(3-imidazolylphenyl)methylamine
N-pentyl-(4-imidazolylphenyl)methylamine
N-pentyl-(2-imidazolyl-5-methoxyphenyl)methylamine
N-pentyl-(3-imidazolyl-4-methoxyphenyl)methylamine
N-neopentyl-(5-imidazolyl-2-methoxyphenyl)methylamine
N-benzyl-(5-imidazolyl-2-methoxyphenyl)methylamine
N-propyl-(5-imidazolyl-2-methoxyphenyl)methylamine
N-propyl-(5-imidazolyl-2,3-dimethoxyphenyl)methylamine
N-pentyl-(5-imidazolyl-2,3-dimethoxyphenyl)methylamine
N-propyl-(5-imidazolyl-2,3-methylenedioxyphenyl) methylamine
N-pentyl-(5-imidazolyl-2,3-methylenedioxyphenyl) methylamine
N-pentyl-[5-imidazolyl-2-(2-pyridylmethyloxy)phenyl] methylamine
N-pentyl-(5-pyrazolyl-2-methoxyphenyl)methylamine
N-pentyl-(5-triazolyl-2-methoxyphenyl)methylamine
N-pentyl-(5-pyrrolyl-2-methoxyphenyl)methylamine Reference Example 3

(Preparation Method F)

Synthesis of N-pentyl-2-(5-imidazolyl-2,3-methylenedioxyphenyl) ethylamine

Carbon tetrabromide (44.3 g, 0.134 mol) was added portionwise to a solution of triphenylphosphine (70.1 g, 0.267 mol) in methylene chloride (200 ml) under ice cooling. A solution of 5-bromo-2,3-methylenedioxybenzaldehyde (27.65 g, 0.121 mol) in methylene chloride (100 ml) was then added dropwise to the mixture over 20 minutes. The reaction mixture was stirred at room temperature for 2 hours, washed with water and with saturated aqueous sodium hydrogen carbonate, and dried over anhydrous magnesium sulfate, and then the solvent was evaporated. The residue was added with ethyl acetate (200 ml), and the mixture was heated to 60° C. and then added with hexane (50 ml). The mixture was cooled to room temperature, and the deposited triphenylphosphine oxide was removed by filtration and the filtrate was concentrated. Triphenylphosphine oxide was removed again in a similar manner by using 100 ml of ethyl acetate and 100 ml of hexane, and the filtrate was concentrated. The residue was purified by silica gel chromatography (Wako Gell C-300: 200 g, eluent: hexane/ethyl acetate=1/10) to give β,β-dibromo-5-bromo-2,3-methylenedioxystyrene (42.36 g).

$^1$HNMR :(CDCl$_3$): δ=6.00(s, 2H), 6.93(d, 1H), 7.39(s, 1H), 7.43(d, 1H)

Diethylene glycol (100 ml), water (60 ml), and 85% potassium hydroxide (32 g, 0.485 mol) were added to β, β-dibromo-5-bromo-2,3-methylenedioxystyrene (42.36 g, 0.11 mol), and the mixture was heated with stirring under reflux for 2 hours. The reaction mixture was poured into ice water and extracted with toluene. The extract was washed with water and dried over anhydrous magnesium sulfate, and then the solvent was evaporated. The residue was recrystallized from ethyl acetate (80 ml) and hexane (300 ml) to give 5-bromo-2,3-methylenedioxyphenylacetic acid (25.35 g).

$^1$HNMR(CDCl$_3$): δ=3.59(s, 2H), 5.98(m, 2 H), 6.80–6.95 (m, 2H)

Thionyl chloride (8.0 ml, 110 mmol) and N,N-dimethylformamide (0.5 ml) were added to a solution of 5-bromo-2,3-methylenedioxypheny lacetic acid (13.75 g, 53.1 mmol) in methylene chloride (180 ml) and the mixture was heated with stirring under reflux for 5 hours. After evaporation of methylene chloride and excessive thionyl chloride, the residue was dissolved in methylene chloride (40 ml). The resulting solution was added dropwise to a solution of n-pentylamine (6.3 ml, 54.3 mmol) and triethylamine (7.5 ml) in methylene chloride (50 ml) over 15 minutes. After stirring for 2 hours at room temperature, the reaction mixture was washed with water and saturated brine and dried over anhydrous sodium sulfate, and then the solvent was evaporated. The residue was purified by silica gel chromatography (Wako Gell C-300: 180 g, eluent: methanol/chloroform=1/50 ) to give N-pentyl-(5-bromo-2, 3-methylene-dioxyphenyl)acetamide (8.61 g).

$^1$HNMR(CDCl$_3$): δ=0.88(t, 3H), 1.10–1.35(m, 4H), 1.47 (q, 2H), 3.23(q, 2H), 3.45(s, 2H), 5.40–5.60(bs, 1H), 5.99(s, 2H), 6.85–6.95(m, 2H)

Imidazole (1.11 g, 16.3 mmol), potassium carbonate (2.78 g, 20.1 mmol), cuprous chloride (0.31 g, 3.1 mmol), and N-methylpyrrolidone (25 ml) were added to N-pentyl-(5-bromo-2,3-methylenedioxyphenyl)acetamide (4.65 g, 14.8 mmol), and the mixture was stirred at 200° C. for 10 hours. The reaction mixture was cooled and added with ethyl acetate (30 ml) and the precipitates were removed by filtration. The ethyl acetate layer was successively washed with 10% aqueous ammonia and with saturated brine, and dried over anhydrous sodium sulfate, and then the solvent was evaporated. The residue was purified by silica gel chromatography (Wako Gell C-300: 100 g, eluent: methanol/chloroform=1/50–1/20) to give N-pentyl-(5-imidazolyl-2,3-methylenedioxyphenyl)acetamide (2.13 g) as an oil.

¹HNMR (CDCl₃): δ=0.88(t, 3H), 1.20–1.40(m, 4H), 1.49 (q, 2H), 3.23(q, 2H), 3.52(s, 2H), 5.60–5.80(bs, 1H), 6.06(s, 2H), 6.70–6.90(m, 2H), 7.10–7.20(m, 2H), 7.75(s, 1H)

A solution of N-pentyl-(5-imidazolyl-2,3-methylenedioxyphenyl) acetamide (2.13 g, 6.75 mmol) and acetic acid (3.5 ml, 61.1 mmol) in tetrahydrofuran (80 ml) was added dropwise to a mixture of sodium borohydride (2.34 g, 61.9 mmol) and tetrahydrofuran (25 ml) over 20 minutes under reflux, and then stirring was continued for 2 hours under reflux. The mixture was added dropwise with water (150 ml) and concentrated hydrochloric acid (25 ml) under ice cooling and then stirring was continued at 60° C. for 2 hours. The reaction mixture was separated by adding ethyl acetate (100 ml) and water (150 ml), and the aqueous layer was made alkaline with sodium hydroxide and then extracted with toluene. The organic layer was washed with water and dried over anhydrous sodium sulfate, and then the solvent was evaporated to give N-pentyl-2-(5-imidazolyl-2,3-methylenedioxyphenyl)ethylamine (1.52 g) as an oil.

¹HNMR(CDCl₃): δ=0.89(t, 3H), 1.20–1.40(m, 4H), 1.49 (q, 2H), 2.64(t, 2H), 2.81(t, 2H), 2.92(t, 2H), 6.03(s, 2H), 6.70–6.75 (m, 2H), 7.16(s, 2H), 7.73(s, 1H)

The amine derivatives set out below (VI-F) were synthesized in the same manner as those described in Reference Example 3.
N-pentyl-2-(3-imidazolylphenyl)ethylamine
N-pentyl-2-(4-imidazolylphenyl)ethylamine
N-pentyl-2-(5-imidazolyl-2-methoxyphenyl)ethylamine
N-pentyl-2-(4-pyrazolylphenyl)ethylamine
N-pentyl-2-(4-triazolylphenyl)ethylamine Reference Example 4

(Preparation Method G)

Synthesis of N-heptyl-2-(2-benzyloxy-3-methoxyphenyl)ethylamine

Nitromethane (100 ml), ammonium acetate (13.4 g, 0.17 mol), and toluene (500 ml) were added to 2-benzyloxy-3-methoxybenzaldehyde (42.2 g, 0.17 mol) and the mixture was heated with stirring under reflux for 8 hours. The reaction mixture was cooled, and washed twice with water and once with saturated brine. After dryness over anhydrous sodium sulfate, the solvent was evaporated. The residue was purified by silica gel chromatography (Wako Gell C-300: 250 g, eluent: hexane/ethyl acetate=4/1) to give 2-nitro-(2-benzyloxy-3-methoxy)vinylbenzene (47.2 g).

¹HNMR(CDCl₃): δ=3.93(s, 3H), 5.10(s,2 H), 6.90–7.45 (m, 8H), 7.55(d, 1H), 8.09(d, 1H)

Ether (1 liter) was added to aluminum lithium hydride (14.0 g, 0.38 mol). The mixture was kept at 20 to 25° C., and was added portionwise with 2-nitro-(2-benzyloxy-3-methoxy)vinylbenzene (47.2 g) over 1.5 hours. After stirring for 1 hour under reflux, the mixture was cooled to 5°–6° C. and added dropwise with ethyl acetate (50 ml) and then with 3% sodium hydroxide (100 ml). The precipitated salts were removed by filtration, the mixture was extracted with methylene chloride and washed with saturated brine. The extract was dried over anhydrous sodium sulfate, and the solvent was evaporated. The residue was purified by silica gel chromatography (Wako Gell C-300: 850 g, eluent: chloroform) to give 2-(2-benzyloxy-3-methoxyphenyl) ethylamine (19.6 g).

¹HNMR(CDCl₃): δ=2.71(t, 2H), 2.87(t, 2H), 3.88(s, 3H), 5.01(s, 2H), 6.70–7.50(m, 8H)

Methylene chloride (100 ml), water (40 ml), and potassium carbonate (5.4 g, 0.039 mol) were added to 2-(2-benzyloxy-3-methoxyphenyl)ethylamine (10.0 g, 0.039 mol), and the solution was cooled to 5° to 6° C. and then added dropwise with a solution of heptanoyl chloride (6.34 g, 0.0427 mol) in methylene chloride (12 ml) while the temperature was kept below 10° C. After stirring at room temperature for 1 hour, the reaction mixture was washed with saturated brine, dried over anhydrous sodium sulfate, and then the solvent was evaporated. The residue was purified by silica gel chromatography (Wako Gell C-300: 160 g, eluent: hexane/ethyl acetate=2/1) to give 5.0 g of N-[2-(2-benzyloxy-3-methoxyphenyl) ethyl]heptamide.

¹HNMR(CDCl₃): δ=0.86(t, 3H), 1.21(m, 6H), 1.48(m, 2H), 1.98(t, 2H), 2.76(t, 2H), 3.40(q, 2H), 3.90(s, 3H), 5.02(s, 3H), 5.84(bs, 1H), 6.75(d, 1H), 6.84(d, 1H), 7.03(t, 1H), 7.33–7.49(m, 5H)

Tetrahydrofuran (45 ml) was added to N-[2-(2-benzyloxy-3-methoxyphenyl)ethyl]heptamide. (3.0 g, 8.12 mmol) and the mixture was cooled to 5°–6° C. This solution was added with sodium borohydride (1.1 g, 29.1 mmol) and then slowly added dropwise with boron trifluoride ether complex (4.8 ml, 39 mmol). After stirring for 2 hours under reflux, the reaction mixture was cooled to 5° to 6° C. and added with 6N aqueous hydrochloric acid (25 ml), and then stirring was continued for 1 hour under reflux. The reaction mixture was made alkaline by adding 25% aqueous sodium hydroxide (35 ml), and then extracted with toluene. The extract was washed with water and dried over anhydrous sodium sulfate, and the solvent was evaporated. The residue was purified by silica gel chromatography (Wako Gell C-300: 40 g, eluent: hexane/ethyl acetate=4/1) to give N-heptyl-2-(2-benzyloxy-3-methoxyphenyl)ethylamine (19.6 g).

¹HNMR(CDCl₃): δ=0.87(t, 3H), 1.25(m, 8H), 1.45(m, 2H), 2.55(t, 2H), 2.80(s, 4H), 3.88(s, 3H), 5.01(s, 2H), 6.81(m,2H), 7.01(t, 1H), 7.32–7.49(m, 5H)

The amine derivatives set out below (IV-G) were synthesized in the same manner as those described in Reference Example 4.
N-heptyl-2-[2-(2-pyridylmethyloxy)-3-methoxyphenyl]ethylamine
N-pentyl-2-[2-(2-pyridylmethyloxy)-3-methoxyphenyl]ethylamine Reference Example 5

(Preparation Method H, Preparation Method I)

Synthesis of 1-amino-5,6,7,8-tetrahydro-2-[3-(4-phenyl-1-piperazyl)propoxy]naphthalene 5,6,7,8-Tetrahydro-2-naphthol (50 g, 0.337 mol) was mixed with ether (400 ml), and the mixture was added dropwise with 60% nitric acid (28 ml, 0.368 mol) while the reaction temperature was kept below 15° C. , and then stirring was continued at 15° to 20° C. for 1 hour. The reaction mixture was added with water (500 ml) and extracted with ethyl acetate, and the extract was washed with saturated brine and dried over anhydrous sodium sulfate, and then the solvent was evaporated. The residue was purified by silica gel chromatography (Wako Gell C-300: 900 g, eluent: hexane/ethyl acetate=50/1 to 60/1) to give 2-hydroxy-5,6,7,8-tetrahydro-1-nitronaphthalene (21.2 g).

¹HNMR(CDCl₃): δ=1.77(m, 4H), 2.74(bs, 2H), 2.97(bs, 2H), 6.92(d, 1H), 7.21(d, 1H), 9.74(s, 1H)

N,N-dimethylformamide (180 ml), potassium carbonate (37.8 g, 0.273 mol), and 1,3-dibromopropane (93 ml, 0.916 mol) were added to 2-hydroxy-5,6,7,8-tetrahydro-1- nitronaphthalene (17.6 g, 0.091 mol) and the mixture was stirred at 70° C. for 4 hours. The precipitated salts were removed by filtration, and then the solvent was evaporated and the residue was extracted with ethyl acetate. The extract was washed with saturated brine and dried over anhydrous magnesium sulfate, and then the solvent was evaporated. The residue was purified by silica gel chromatography (Wako Gell C-300: 500 g, eluent: ethyl acetate/hexane=1/20) to give 5,6,7,8-tetrahydro-1-nitro-2-(3-bromopropoxy) naphthalene (19.4 g).

$^1$HNMR(CDCl$_3$): δ=1.79(m, 4H), 2.28(m, 2H), 4.64(bs, 2H), 4.74(bs, 2H), 3.55(t, 2H), 4.17(m, 2H), 6.83(d, 1H), 7.12(d, 1H)

1-Phenylpiperazine (2.77 g, 17.1 mmol), potassium carbonate (7.1 g, 51.4 mmol) and N,N-dimethylformamide (30 ml) were added to 5,6,7,8-tetrahydro-1-nitro-2-(3-bromopropoxy)naphthalene (4.8 g, 15.3 mmol) and the mixture was stirred at 60° C. for 8 hours. The reaction mixture was added with water (80 ml) and extracted with ethyl acetate. The extract was washed with saturated brine and dried over anhydrous magnesium sulfate, and then the solvent was evaporated. The residue was purified by silica gel chromatography (Wako Gell C-300: 200 g, eluent: hexane/ethyl acetate=7/1 to 3/1) to give 5,6,7,8-tetrahydro-1-nitro-2-[3-(4-phenyl-1-piperazinyl) propoxy]naphthalene (5.5 g).

$^1$HNMR(CDCl$_3$): δ=1.77(m, 4H), 1.99(m, 2H), 2.53(t, 2H), 2.63(m,6H), 2.73(bs, 2H), 3.20(t, 4H), 4.11(t, 2H), 6.80–6.88(m, 3H), 6.93(d, 1H), 7.10(d, 1H), 7.23–7.29(m, 2H)

Iron powder (15 g, 0.27 mol), isopropyl alcohol (45 ml), water (11 ml), and acetic acid (1.5 ml, 26.2 mmol) were added to 5,6,7,8-tetrahydro-1-nitro-2-[3-(4-phenyl-1-piperazinyl)propoxy]naphthalene (5.5g, 13.9 mmol) and stirred for 2 hours under reflux. After cooling the reaction mixture, the mixture was added with potassium carbonate (10 g) that was dissolved in a small volume of water. After stirring for several minutes, ethyl acetate was added to the reaction mixture and the precipitates were removed by filtration. The filtrate was concentrated and the residue was extracted with ethyl acetate. The extract was washed with saturated brine and dried over anhydrous sodium sulfate, and then the solvent was evaporated to give 1-amino-5,6,7, 8-tetrahydro-2-[3-(4-phenyl-1-piperazinyl)propoxy] naphthalene (4.9 g).

$^1$HNMR(CDCl$_3$): δ=1.72–1.85(m, 4H), 2.04(q, 2H), 2.48 (t, 2H), 2.58–2.72(m, 8H), 3.22(t, 4H), 3.76(bs, 2H), 4.06(t, 2H), 6.48(d, 1H), 6.65(d, 1H), 6.85–6.96(m, 3H), 7.27(m, 2H)

The aniline derivatives set out below (II-H) were synthesized in the same manner as those described in Reference Example 5.

2-{3-(4-phenyl-1-piperazinyl)propoxy}-6-methylaniline
2-{2-(4-phenyl-1-piperazinyl)ethoxy}-6-methylaniline
2-{3-(4-methyl-1-piperazinyl)propoxy}-6-methylaniline
2-[3-{4-(2-pyridyl)-1-piperazinyl}propoxy]-6-methylaniline Example 1

(Preparation Method A)

Preparation of the compound:

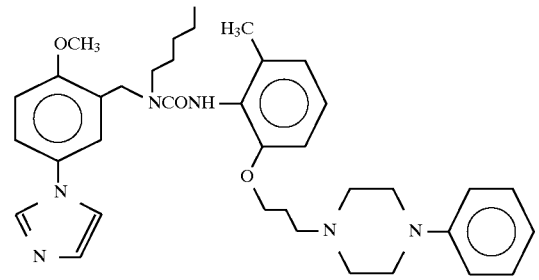

Methylene chloride (220 ml) was added to 2-{3-(4-phenyl-1-piperazinyl)propoxy}-6-methylaniline (7.0 g, 21.5 mmol) and the mixture was cooled to 5° to 6° C. The mixture was added portionwise with bis(trichloromethyl) carbonate (2.1 g, 7.08 mmol) and further added dropwise with trimethylamine (6.5 g, 64.2 mmol) while the temperature was kept below 10° C. After stirring at 10° to 20° C. for 1 hour, the mixture was added with N-pentyl-(5-imidazolyl-2-methoxyphenyl)methylamine (5.88 g, 21.5 mmol) and stirred at room temperature for 1 hour. The reaction mixture was twice washed with water (300 ml) and dried over anhydrous magnesium sulfate, and then the solvent was evaporated. The residue was purified by silica gel chromatography (Wako Gell C-300:70 g, eluent: methanol/chloroform (1/100 to 1/50) and the product was recrystallized from ethyl acetate/n-heptane (1/2.46, 226 ml) to give N-{5-(1-imidazolyl)-2-methoxyphenyl}methyl-N-(1-pentyl)-N'-[2-{3-(4-phenyl-1-piperazinyl)propoxy}-6-methylphenyl]urea (11.7 g).

$^1$HNMR(CDCl$_3$): δ=0.91(t, 3H), 1.36(m, 4 H), 1.84(m, 4H), 2.25(s, 3H), 2.43(t, 2H), 2.54(t, 4H), 3.18(t, 4H), 3.40(t, 2H), 3.91(s, 3H), 3.98(t, 2H), 4.64(s, 2H), 6.18(s, 1H), 6.71–7.03(m, 7H), 7.18–7.34(m, 6H), 7.77(s, 1H)

Example 2

Preparation of the compound:

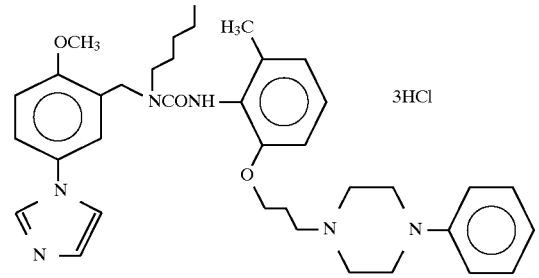

Ethyl acetate (175 ml) was added to N-{5-(1-imidazolyl) -2-methoxyphenyl}methyl-N-(1-pentyl)-N'-[2-{3-(4-phenyl-1-piperazinyl)propoxy}-6-methylphenyl]urea (11.7 g, 0.0187 mol). The mixture was added dropwise with 4N HCl solution in ethyl acetate (16 ml, 0.064 mol) at room temperature with stirring. After stirred for 1 hour at room temperature, the mixture was added with ether (100 ml), and stirring was continued for 1 hour at room temperature. The precipitated amorphous crystals were collected by filtration under nitrogen atmosphere and dried at 60° C. under reduced pressure to give N-{5-(1-imidazolyl)-2-methoxyphenyl}methyl-N-(1-pentyl)-N'-[2-{3-(4-phenyl-1-piperazinyl)propoxy}-6-methyphenyl]urea trihydrochloride. (13.15 g).

¹HNMR(DMSO-d₆): δ=0.85(t, 3H), 1.27(m, 4H), 1.59(m, 2H), 2.08(m, 5H), 3.20–3.46(m, 6H), 3.89(s, 3H), 3.99(t, 2H), 4.31(bs, 4H), 4.54(s, 2H), 6.78(d, 1H), 6.85(m, 2H), 6.97–7.05(m, 3H), 7.23–7.28(m, 3H), 7.44(d, 1H), 7.56(s, 1H), 7.67(m, 1H), 7.93(d, 1H), 8.14(d, 1H), 9.72(s, 1H), 11.54(bs, 1H)

Example 3

Preparation of the compound:

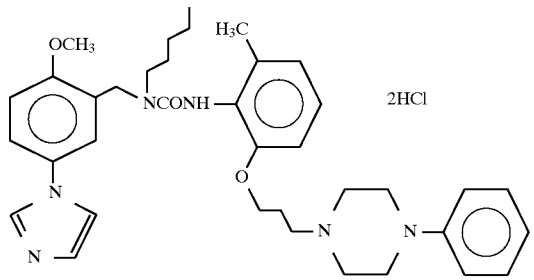

Acetone (84 ml) and water (8.4 ml) were added to N-{5-(1-imidazolyl)-2-methoxyphenyl}methyl-N-(1-pentyl)-N'-[2-{3-(4-phenyl-1-piperazinyl)propoxy}-6-methylphenyl]urea (5.0 g, 8.0 mmol). The mixture was added dropwise with concentrated hydrochloric acid (1.5 ml, 17 mmol) with stirring at room temperature, and then added with seed crystals. After stirring for 3 hours under ice cooling, the precipitated crystals were collected by filtration and dried at 60° C. under reduced pressure to give N-{5-(1-imidazolyl)-2-methoxyphenyl}methyl-N-(1-pentyl)-N'-[2-{3-(4-phenyl-1-piperazinyl)propoxy}-6-methylphenyl]urea dihydrochloride (5.1 g).

¹HNMR(DMSO-d₆): δ=0.85(t, 3H), 1.27(m, 4H), 1.59(m, 2H), 2.08(m, 5H), 3.17–3.38 (bm, 12H), 3.89(s, 3H), 3.99(t, 2H), 4.54(s, 2H), 6.80(d, 1H), 6.85(m, 2H), 6.97–7.05(m, 3H), 7.23–7.28(m, 3H), 7.44(d, 1H), 7.56(s, 1H), 7.68(m, 1H), 7.90(d, 1H), 8.11 (d, 1H), 9.65(s, 1H)

The compounds of Examples 4 through 63 and the compounds of Examples 72 through 75 were synthesized in the same manner as those of Examples 1 to 3.

Among these compounds, compounds having higher hygroscopic properties may absorb moisture when kept under ambient atmosphere to form substances represented by the following formula:

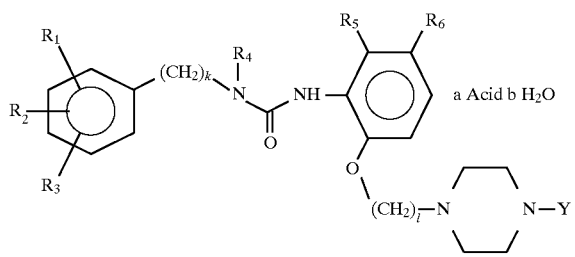

wherein $R_1$, $R_2$, $R_3$, $R_4$, $R_5$, $R_6$, k, l, and Y are the same as those defined above; symbol "a" represents 0 or an arbitrary integer or represents an arbitrary fraction; and symbol "b" represents an arbitrary integer or an arbitrary fraction. For example, 3.3% weight increase was observed by Karl Fisher method after N-{5-(1-imidazolyl)-2-methoxyphenyl}methyl-N-(1-pentyl)-N'-[2-{3-(4-phenyl-1-piperazinyl)propoxy}-6-methylphenyl]urea dihydrochloride obtained in Example 3 was kept under ambient atmosphere for 2 days.

Example 4

¹H NMR DMSO-d₆ δ=0.84(t, 3H), 1.27(m, 4H), 1.58(m, 2H), 2.08(m, 5H), 3.14–3.46(m, 12H), 3.87(s, 3H), 3.99(t, 2H), 4.53(s, 2H), 6.78–7.06(m, 6H), 7.19–7.28(m, 3H), 7.36(d, 1H), 7.52–7.58(m, 3H), 7.82(s, 1H), 8.86(s, 1H)

Example 5

¹H NMR CDCl₃ δ=0.91(t, 3H), 1.34(m, 4H), 1.71(m, 2H), 1.88(m, 2H), 2.23(s, 3H), 2.47(s, 2H), 2.59(t, 2H), 2.70(t, 4H), 3.22(t, 4H), 3.40(t, 2H), 3.90(s, 3H), 3.96(t, 2H), 4.64(s, 2H), 6.20(m, 2H), 6.72(d, 1H), 6.88–7.03(m, 6H), 7.18–7.83(m, 6H), 7.84(s, 1H)

Example 6

¹H NMR CDCl₃ δ=0.90(t, 3H), 1.35(m, 4H), 1.71(m, 2H), 1.91(m, 2H), 2.22(s, 3H), 2.46(s, 4), 2.72(t, 2H), 2.84(t, 4H), 3.26(t, 4H), 3.40(t, 2H), 3.90(s, 3H), 3.95(t, 2H), 4.63(s, 2H), 6.24(s, 1H), 6.71(d, 1H), 6.81(d, 1H), 6.89–6.97(m, 4H), 7.04(t, 1H), 7.20–7.34(m, 6H), 7.71 (bs, 2H), 7.91(s, 1H)

Example 7

¹H NMR DMSO-d₆ δ=0.85(t, 3H), 1.27(m, 4H), 1.59(m, 2H), 2.04–2.08(m, 5H), 2.35(s, 6H), 3.16–3.37(m, 12H), 3.89(s, 3H), 4.01(t, 2H), 4.55(s, 2H), 6.78–6.89(m, 3H), 6.98–7.07(m, 3H), 7.25(m, 3H), 7.43(d, 1H), 7.53 (s, 1H), 7.67(m, 1H), 7.91(s, 1H), 8.08(s, 1H), 9.54(s, 1H)

Example 8

¹ H NMR CDCl₃ δ=0.87(t, 3H), 1.24(bs, 8H), 1.55–1.72 (m, 6H), 1.90(m, 2H), 2.45(t, 2H), 2.56(m, 6H), 2.70(m, 2), 3.16–3.28(m, 6H), 3.91–3.96(m, 5H), 4.42(s, 2H), 5.05(s, 2H), 5.82(s, 1H), 6.64(d, 1H), 6.83–6.94(m, 6H), 7.09(t, 1H), 7.21–7.39(m, 7H)

Example 9

¹H NMR CDCl₃ δ=1.72(bs, 4H), 1.86(m, 4H), 2.40(t, 2H), 2.47–2.61(m, 8H), 2.68(d, 2H), 3.14(t, 4H), 3.31(t, 2H), 3.91(m, 5H), 4.41(s, 2H), 5.05(s, 2H), 5.80(s, 1H), 6.64(d, 1H), 6.83–6.93(m, 6H), 7.06–7.38(m, 13H)

Example 10

¹H NMR CDCl₃ δ=0.90(m, 3H), 1.27–1.40(m, 4H), 1.76–1.96(m, 8H), 2.25–2.63(m, 6H), 2.71(d, 4H), 3.17(m, 4H), 3.36(t, 2H), 4.00(m, 2H), 4.63(d, 2H), 5.97(d, 1H), 6.67(t, 1H), 6.71–6.94(m, 4H), 7.19–7.30(m, 4H), 7.37–7.52 (m, 4H), 7.87(d, 1H)

Example 11

¹H NMR CDCl₃ δ=0.92(t, 3H), 1.37(m, 4H), 1.93(m, 4H), 2.28(s, 3H), 2.50–2.59(m, 6H), 3.18(m, 4H), 3.36(t, 2H), 4.02(m, 2H), 4.65(s, 2H), 6.10(s, 1H), 6.72–7.05(m, 6H), 7.20–7.52(m, 8H), 7.86(s, 1H)

Example 12

¹H NMR CDCl₃ δ=0.91(t, 3H), 1.37(m, 4H), 1.92(m, 4H), 2.28(s, 3H), 2.50(m, 6H), 3.36(t, 2H), 3.52(t, 4H), 4.01(m,

2H), 4.65(s, 2H), 6.09(s, 1H), 6.61–6.85(m, 4H), 7.05(m, 1H), 7.29(m, 2H), 7.37–7.52(m, 5H), 7.87(d, 1H), 8.20(d, 1H)

Example 13

¹H NMR CDCl₃ δ=1.73(m, 6H), 2.35(t, 2H), 2.50(t, 4H), 2.63–2.70(m, 4H), 3.16(t, 4H), 3.84(s, 3H), 3.91(t, 2H), 4.68(s, 4H), 6.13(s, 1H), 6.67(d, 1H), 6.86–6.95(m, 5H), 7.20–7.38(m, 11H), 7.75(s, 1H)

Example 14

¹H NMR CDCl₃ δ=1.72(m, 2H), 2.24(s, 3H), 2.34(t, 2H), 2.49(t, 4H), 3.16(t, 4H), 3.85(s, 3H), 3.91(t, 2H), 4.69(s, 4H), 6.25(s, 1H), 6.75(d, 1H), 6.83–7.02(m, 6H), 7.19–7.74 (m, 11H), 7.75(s, 1H)

Example 15

¹H NMR CDCl₃ δ=0.88(t, 3H), 1.28(m, 4H), 1.58(m, 2H), 1.96(m, 2H), 2.25(s, 3H), 2.51(t, 2H), 2.58(t, 4H), 3.20(m, 6H), 4.03(t, 2H), 4.42(s, 2H), 6.06(s, 1H), 6.74(d, 1H), 6.75–7.10(m, 6H), 7.24–7.62(m, 8H)

Example 16

¹H NMR CDCl₃ δ=0.99(t, 3H), 1.75(m, 2H), 1.89(m, 2H), 2.26(s, 3H), 2.47(t, 2H), 2.55(t, 4H), 3.18(t, 4H), 3.34(t, 2H), 3.87(s, 3H), 3.92(s, 3H), 4.00(t, 2H), 4.69(s, 2H), 6.22(s, 1), 6.73(d, 1H), 6.81–7.03(m, 7H), 7.18–7.29(m, 4H), 7.79(s, 1H)

Example 17

¹H NMR CDCl₃ δ32 0.91(t, 31), 1.36(m, 4H), 1. 76–1.86 (m, 4H), 2.25(s, 3H), 2.41(t, 2H), 2.48(t, 4H), 3.40(t, 2H), 3.51(t, 4H), 3.90(s, 3H), 3.98(t, 2H), 4.64(s, 2H), 6.17(s, 1H), 6.62–6.65(m, 2H), 6.72(d, 1H), 6.82(d, 1H), 6.94(d, 1H), 7.02(t, 1H), 7.19(d, 2H), 7.26(m, 1H), 7.34(d, 1H), 7.47(m, 1H), 7.77(s, 1H), 8.19(d, 1H)

Example 18

¹H NMR CDCl₃ δ=0.90(t, 3H), 1.34(m, 4H), 1.70(m, 2H), 2.25(s, 3H), 2.56(t, 4H), 2.63(t, 2H), 3.12(t, 4H), 3.40(t, 2H), 3.78(s, 3H), 4.08(t, 2H), 4.64(s, 2H), 6.32(s, 1H), 6.85(d, 1H), 6.87–6.95(m, 5H), 7.03(t, 1H), 7.17– 7.28(m, 5H), 7.34(d, 1H), 7.77(s, 1H)

Example 19

¹H NMR CDCl₃ δ=0.96(t, 3H), 1.67–1.86(m, 4H), 2.25(s, 3H), 2.43(t, 2H), 2.54(t, 4H), 3.18(t, 4H), 3.38(t, 2H), 3.90(s, 3H), 4.00(t, 2H), 4.65(s, 2H), 6.18(s, 1H), 6.73(d, 1H), 6.84(q, 2H), 6.93(t, 3H), 7.02(t, 1H), 7.16–7.29(m, 6H), 7.34(d, 1H), 7.77(s, 1H)

Example 20

¹H NMR CDCl₃ δ=0.91(t, 3H), 1.39(m, 4H), 1.77(m, 2H), 2.23(s, 3H), 2.40(m, 2H), 3.40(m, 2H), 3.60(m, 2H), 3.72(m, 2H), 3.82–4.00(m, 8H), 4.15(m, 4H), 4.42(t, 2H), 4.72(s, 2H), 6.65(m, 2H), 6.81(m, 1H), 7.00(m, 2H), 7.33–7.66(m, 7H), 10.30(bs, 1H)

Example 21

¹H NMR CDCl₃ δ=0.98(t, 3H), 1.78(m, 4H), 2.24(s, 3H), 2.35(s, 3H), 2.35–2.43(m, 10H), 3.37(t, 2H), 3.90(s, 3H), 3.94(t, 2H), 4.63(s, 2H), 6.18(s, 1H), 6.70(d, 1H), 6.81(d, 1H), 6.93–7.01(m, 2H), 7.21(d, 1H), 7.27(m, 1H), 7.33(d, 1H), 7.76(s, 1H)

Example 22

¹H NMR CDCl₃ δ=1.02(t, 3H), 1.82(m, 2H), 2.23(s, 3H), 2.35(m, 2H), 2.90(s, 3H), 3.40(t, 2H), 3.60–3.73(m, 4H), 3.90–4.05(m, 9H), 4.17(t, 2H), 4.66(s, 2H), 6.65(d, 1H), 6.72(d, 1H), 6.99(m, 2H), 7.27(m, 1H), 7.38(s, 1H), 7.47(s, 1H), 7.65(s, 1H), 10.31(s, 1H)

Example 23

¹H NMR CDCl₃ δ=1.01(t, 3H), 1.73–1.92(m, 4H), 2.25(s, 3H), 2.47(t, 2H), 2.55(t, 4H), 3.18(t, 4H), 3.36(t, 2H), 4.00(t, 2H), 4.61(s, 2H), 6.06(s, 2H), 6.18(s, 1H), 6.79–6.94(m, 7H), 7.03(t, 1H), 7.16(d, 2H), 7.26(m, 2H), 7.73(s, 1H)

Example 24

¹H NMR CDCl₃ δ=0.92(t, 3H), 1.38(m, 4H), 1.74(m, 2H), 1.89(m, 2H), 2.25(s, 3H), 2.46(t, 2H), 2.55(t, 4H), 3.18(t, 4H), 3.38(t, 2H), 4.01(t, 2H), 4.61(s, 2H), 6.06(s, 2H), 6.17(s, 1H), 6.72–6.93(m, 7H), 7.04(t, 1H), 7.15(d, 2H), 7.27(t, 2H), 7.73(s, 1H)

Example 25

¹H NMR CDCl₃ δ=0.87(t, 3H), 1.29(m, 4H), 1.61(m, 2H), 1.87(t, 2H), 2.20(s, 3H), 2.45(t, 2H), 2.55(t, 4H), 3.17(t, 4H), 3.34(t, 2H), 3.87(s, 3H), 3.95(t, 2H), 4.62(s, 2H), 5.19(s, 2H), 6.11(s, 1H), 6.69(d, 1H), 6.78–7.10(m, 9H), 7.26(t, 2H), 7.57(d, 1H), 7.65(t, 1H), 8.52(d, 1H)

Example 26

¹H NMR CDCl₃ δ=0.86(t, 3H), 1.28(m, 4H), 1.63(m, 2H), 2.17(s, 3H), 2.27(m, 2H), 3.41(m, 4H), 3.67(d, 2H), 3.82(d, 2H), 3.88(s, 3H), 4.11(m, 4H), 4.67(t, 2H), 4.88(s, 2H), 5.66(s, 2H), 6.73(d, 1H), 6.81(d, 1H), 6.97(d, 2H), 7.06(t, 1H), 7.15(t, 1H), 7.50(m, 3H), 7.78(t, 1H), 7.91(m, 2H), 8.27(d, 1H), 8.40(t, 1H), 8.65(d, 1H)

Example 27

¹H NMR CDCl₃ δ=0.86(t, 3H), 1.28(m, 4H), 1.66–1.72 (m, 8H), 1.87(m, 2H), 2.45(t, 2H), 2.55(m, 4H), 2.70(t, 2H), 3.17(t, 4H), 3.33(t, 2H), 3.87(s, 3H), 3.94(t, 2H), 4.62(s, 2H), 5.19(s, 2H), 6.00(s, 1H), 6.65(d, 1H), 6.83–7.13(m, 8H), 7.26(t, 2H), 7.57(d, 1H), 7.66(m, 1H), 8.53(d, 1H)

Example 28

¹H NMR CDCl₃ δ=0.87(t, 3H), 1.30(m, 4H), 1.62–1.71 (m, 6H), 2.22(m, 2H), 2.61(bs, 2H), 2.68(bs, 2H), 3.36(m, 4H), 3.62(m, 4H), 3.88(m, 5H), 4.06(t, 2H), 4.43(t, 2H), 4.84(s, 2H), 5.66(s, 2H), 6.64(d, 1H), 6.67(bs, 1H), 6.88–6.97(m, 3H), 7.16(t, 1H), 7.37(t, 1H), 7.46(t, 2H), 7.68(d, 2H), 7.75(t, 1H), 8.33–8.39(m, 2H), 8.58(d, 1H)

Example 29

¹H NMR CDCl₃ δ=0.90(t, 3H), 1.33(m, 4H), 1.68–1.82 (m, 4H), 2.25(s, 3H), 2.41(t, 2H), 2.52(t, 4H), 3.16(t, 4H), 3.42(t, 2H), 3.96(t, 2H), 4.76(s, 2H), 5.29(s, 2H), 6.19(s, 1H), 6.84(d, 1H), 6.89–7.03(m, 5H), 7.18–7.26(m, 7H), 7.38(d, 1H), 7.50(d, 1H), 7.71(t, 1H), 7.76(s, 1H), 8.60(d, 1H)

Example 30

¹H NMR CDCl₃ δ=0.90(t, 3H), 1.37(m, 4H), 1.76(m, 2H), 2.21–2.31(m, 5H), 3.19(m, 2H), 3.27(t, 2H), 3.41–3.68(m, 8H), 3.93(t, 2H), 4.84(s, 2H), 5.61(s, 2H), 6.62(d, 1H), 6.85(d, 1H), 6.94(t, 3H), 7.05(t, 1H), 7.27(m, 3H), 7.43(m,

2H), 7.55(d, 2H), 7.65(d, 1H), 7.91(d, 1H), 8.05(t, 1H), 8.32(d, 1H), 9.86(s, 1H)

Example 31

$^1$H NMR CDCl$_3$ δ=0.88(t, 3H), 1.36(m, 4H), 1.74(m, 2H), 2.23–2.70(m, 5H), 3.41(t, 2H), 3.57(t, 2H), 3.75(d, 2H), 3.94(m, 6H), 4.37(m, 2H), 4.95(s, 2H), 5.98(s, 2H), 6.59(d, 1H), 6.83(d, 1H), 7.03(t, 1H), 7.38–7.56(m, 6H), 7.70–7.76(m, 6H), 8.25(bs, 1H), 8.37(d, 1H), 8.50(t, 1H), 9.94(s, 1H)

Example 32

$^1$H NMR CDCl$_3$ δ=0.88(t, 3H), 1.31(m, 4H), 1.69(m, 2H), 1.84(t, 2H), 2.23(s, 3H), 2.42(t, 2H), 2.54(t, 4H), 3.17(t, 4H), 3.42(t, 2H), 3.94(t, 2H), 4.73(s, 2H), 5.26(s, 2H), 6.16(s, 1H), 6.68(d, 1H), 6.78–7.02(m, 7H), 7.22–7.29(m, 4H), 7.36(d, 1H), 7.48(d, 1H), 7.67(t, 1H), 8.58(d, 1H)

Example 33

$^1$H NMR CDCl$_3$ δ=0.90(t, 3H), 1.32(m, 4H), 1.64(m, 2H), 1.91(m, 2H), 2.24(s, 3H), 2.47(t, 2H), 2.56(t, 4H), 3.17(t, 4H), 3.34(t, 2H), 3.99(t, 2H), 4.54(s, 2H), 5.20(s, 2H), 6.04(s, 1H), 6.72(d, 1H), 6.82–6.91(m, 7H), 7.22–7.28(m, 5H), 7.52(d, 1H), 7.68(t, 1H), 8.58(d, 1H)

Example 34

$^1$H NMR CDCl$_3$ δ=0.90(t, 3H), 1.34(m, 4H), 1.68(m, 2H), 2.22(s, 3H), 2.29(m, 2H), 3.24(t, 2H), 3.42(t, 2H), 3.62(m, 6H), 4.15(m, 4H), 4.58(s, 2H), 5.75(s, 2H), 6.13(s, 1H), 6.71(d, 1H), 6.82(d, 1H), 7.03(t, 1H), 7.18–7.49(m, 9H), 7.81(t, 1H), 8.12(d, 1H), 8.36(t, 1H), 8.76(d, 1H)

Example 35

$^1$H NMR CDCl$_3$ δ=0.90(t, 3H), 1.33(m, 4H), 1.66(m, 2H), 1.89(m, 2H), 2.25(s, 3H), 2.45(t, 2H), 2.54(t, 4H), 3.17(t, 4H), 3.36(t, 2H), 3.98(t, 2H), 4.58(s, 2H), 5.20(s, 2H), 6.05(s, 1H), 6.71(d, 1H), 6.69–7.01(m, 8H), 7.23–7.28(m, 4H), 7.52(d, 1H), 7.70(t, 1H), 8.58(d, 1H)

Example 36

$^1$H NMR CDCl$_3$ δ=0.90(t, 3H), 1.34(m, 4H), 1.69(m, 2H), 2.10(s, 3H), 2.27(m, 2H), 3.33(t, 2H), 3.47(m, 2H), 3.63(d, 2H), 3.75(d, 2H), 3.90(t, 2H), 4.15(t, 2H), 4.50(t, 2H), 4.65(s, 2H), 5.74(s, 2H), 6.26(s, 1H), 6.72(d, 1H), 6.78(d, 1H), 7.02(m, 3H), 7.25(s, 1H), 7.31–7.48(m, 4H), 7.70(m, 3H), 8.09(d, 1H), 8.38(t, 1H), 8.74(d, 1H)

Example 37

$^1$H NMR CDCl$_3$ δ=0.91(t, 3H), 1.38(m, 4H), 1.77(m, 2H), 2.22(s, 3H), 2.46(m, 2H), 3.44(m, 2H), 3.65–3.87(m, 6H), 4.12(m, 4H), 4.33(m, 2H), 4.77(s, 2H), 6.66–6.82(m, 3H), 7.00(t, 2H), 7.31–7.60(m, 9H), 7.79(s, 1H), 10.31(s, 1H)

Example 38

$^1$H NMR CDCl$_3$ δ=0.92(t, 3H), 1.35(m, 4H), 1.72(m, 2H), 1.95(t, 2H), 2.28(s, 3H), 2.47–2.59(m, 6H), 3.18(t, 4H), 3.36(t, 2H), 4.02(t, 2H), 4.65(s, 2H), 6.10(s, 1H), 6.74(d, 1H), 6.82–6.93(m, 4H), 7.05(t, 2H), 7.19–7.30(m, 4H), 7.37–7.48(m, 4H), 7.87(s, 1H)

Example 39

$^1$H NMR CDCl$_3$ δ=0.91(t, 3H), 1.35(m, 4H), 1.71(bs, 2H), 2.20(s, 3H), 2.34(bs, 2H), 3.47(m, 4H), 3.51(m, 2H), 3.64(m, 4H), 4.21–4.33(m, 4H), 4.77(s, 2H), 6.71(m, 3H), 6.93(t, 1H), 7.26–7.75(m, 10H), 9.75(s, 1H)

Example 40

$^1$H NMR CDCl$_3$ δ=0.88(t, 3H), 1.31(m, 4H), 1.68(m, 2H), 1.84(m, 2H), 2.23(s, 3H), 2.42(t, 2H), 2.53(t, 4H), 3.16(t, 4H), 3.39(t, 2H), 3.77(s, 3H), 3.93(t, 2H), 4.65(s, 2H), 5.22(s, 2H), 6.20(s, 1H), 6.54(m, 2H), 6.68(d, 1H), 6.78–7.00(m, 5H), 7.20(m, 1H), 7.23–7.29(m, 3H), 7.48(d, 1H), 7.63(t, 1H), 8.56(d, 1H)

Example 41

$^1$H NMR CDCl$_3$ δ=0.91(t, 3H), 1.34(m, 4H), 1.69(m, 2H), 2.22(s, 3H), 2.30(m, 2H), 3.23(t, 2H), 3.43(t, 2H), 3.59(m, 6H), 3.88(s, 3H), 4.13(m, 4H), 4.58(s, 2H), 5.73(s, 2H), 6.10(s, 1H), 6.72(d, 1H), 6.83(d, 1H), 6.90(m, 2H), 7.04(t, 1H), 7.20(d, 2H), 7.37(d, 4H), 7.79(t, 1H), 8.21(d, 1H), 8.38(t, 1H), 8.71(d, 1H)

Example 42

$^1$H NMR CDCl$_3$ δ=0.90(t, 3H), 1.32(m, 4H), 1.64(m, 2H), 1.89(m, 2H), 2.23(s, 3H), 2.46(t, 2H), 2.54(t, 4H), 3.18(t, 4H), 3.30(t, 2H), 3.90(s, 3H), 3.98(t, 2H), 4.49(s, 2H), 5.27(s, 2H), 6.03(s, 1H), 6.70(d, 1H), 6.79–7.01(m, 8H), 7.20–7.28(m, 3H), 7.57(d, 1H), 7.67(t, 1H), 8.57(d, 1H)

Example 43

$^1$H NMR CDCl$_3$ δ=0.90(t, 3H), 1.34(m, 4H), 1.67(m, 2H), 2.08(s, 3H), 2.35(m, 2H), 3.27–3.47(m, 6H), 3.60(t, 4H), 3.89(m, 5H), 4.16(t, 2H), 4.55(s, 2H), 5.70(s, 2H), 6.16(s, 1H), 6.73(d, 1H), 6.79(d, 1H), 6.94(d, 1H), 7.01–7.36(m, 8H), 7.67(t, 1H), 8.15(d, 1H), 8.32(t, 1H), 8.60(d, 1H)

Example 44

$^1$H NMR CDCl$_3$ δ=0.90(t, 3H), 1.33(m, 4H), 1.66(m, 2H), 1.90(m, 2H), 2.25(s, 3H), 2.47(t, 2H), 2.56(t, 4H), 3.18(t, 4H), 3.34(t, 2H), 3.90(s, 3H), 3.99(t, 2H), 4.53(s, 2H), 5.27(s, 2H), 6.07(s, 1H), 6.72(d, 1H), 6.80–7.02(m, 8H), 7.23–7.28(m, 3H), 7.57(d, 1H), 7.68(t, 1H), 8.57(d, 1H)

Example 45

$^1$H NMR CDCl$_3$ δ=0.90(t, 3H), 1.34(m, 4H), 1.69(m, 2H), 2.12(m, 2H), 2.28(s, 3H), 3.42–3.61(m, 8H), 3.83(m, 7H), 4.34(m, 2H), 4.85(s, 2H), 5.98(s, 2H), 6.54(m, 2H), 6.85(d, 1H), 7.02(m, 2H), 7.20(d, 1H), 7.41–7.51(m, 4H), 7.61(t, 1H), 7.79(d, 2H), 8.08(bs, 1H), 8.33–8.41(m, 2H)

Example 46

$^1$H NMR CDCl$_3$ δ=0.91(t, 3H), 1.34(m, 4H), 1.66(m, 2H), 2.16(s, 3H), 2.39(bs, 2H), 3.05(t, 2H), 3.33(t, 2H), 3.47(m, 2H), 3.65(m, 6H), 3.80(d, 2H), 4.20(m, 4H), 6.52(s, 1H), 6.73(t, 2H), 6.95(t, 1H), 7.20(bs, 1H), 7.35–7.57(m, 10H), 9.46(s, 1H)

Example 47

$^1$H NMR CDCl$_3$ δ=0.90(t, 3H), 1.34(m, 4H), 1.74(m, 4H), 2.25(s, 3H), 2.36(t, 2H), 2.49(t, 4H), 3.15(t, 4H), 3.43(t, 2H), 3.90(s, 5H), 4.65(s, 2H), 6.20(s, 1H), 6.44(t, 1H), 6.68(d, 1H), 6.79–7.04(m, 7H), 7.23–7.30(m, 1H), 7.58–7.69(m, 3H), 7.85(d, 1H)

Example 48

$^1$H NMR CDCl$_3$ δ=0.89(t, 3H), 1.33(m, 4H), 1.69(m, 2H), 2.23(m, 5H), 2.77(t, 2H), 2.95(t, 2H), 3.30(d, 2H), 3.41–3.55(m, 6H), 3.90(s, 3H), 4.05(t, 2H), 4.63(s, 2H), 6.23(s, 1H), 6.48(t, 1H), 6.71(d, 1H), 6.83–7.10(m, 7H), 7.23–7.30(m, 1H), 7.55(d, 1H), 7.68(d, 1H), 7.75(d, 1H), 7.88(d, 1H)

Example 49

¹H NMR CDCl₃ δ=0.91(t, 3H), 1.36(m, 4H), 1.70–1.86 (m, 4H), 2.25(s, 3H), 2.42(t, 2H), 2.53(t, 4H), 3.17(t, 4H), 3.42(t, 2H), 3.92(s, 3H), 3.97(t, 2H), 4.65(s, 2H), 6.19(s, 1H), 6.72(d, 1H), 6.80–7.06(m, 7H), 7.23–7.30(m, 1H), 7.54–7.60(m, 2H), 8.07(s, 1H), 8.46(s, 1H)

Example 50

¹H NMR CDCl₃ δ=0.90(t, 3H), 1.37(m, 4H), 1.74(t, 2H), 2.23(s, 3H), 2.31(bs, 2H), 3.24(t, 2H), 3.54–3.77(m, 8H), 3.93(s, 3H), 4.12(t, 2H), 4.26(t, 2H), 4.66(s, 2H), 6.41(s, 1H), 6.71(d, 1H), 6.84(d, 1H), 7.05(m, 2H), 7.28(m, 2H), 7.39–7.52(m, 4H), 7.66(d, 1H), 7.75(d, 1H), 8.25(s, 1H)

Example 51

¹H NMR CDCl₃ δ=0.87(t, 3H), 1.26(m, 4H), 1.59(m, 2H), 1.95(m, 2H), 2.20(s, 3H), 2.53(m, 6H), 3.05(t, 2H), 3.14(t, 4H), 3.26(t, 2H), 3.50(t, 2H), 3.84(s, 3H), 3.95(t, 2H), 5.17(s, 2H), 6.20(s, 1H), 6.66(d, 1H), 6.79–6.91(m, 6H), 6.97–7.06(m, 3H), 7.25(t, 2H), 7.49(t, 1H), 7.53(d, 1H), 8.04(d, 1H)

Example 52

¹H NMR CDCl₃ δ=0.88(t, 3H), 1.30(m, 4H), 1.59(m, 2H), 2.13(s, 3H), 2.36(bs, 2H), 3.10(t, 2H), 3.39(t, 2H), 3.45–3.68 (m, 6H), 3.80(s, 3H), 3.91(bs, 4H), 4.13(bs, 2H), 4.43(t, 2H), 5.58(s, 2H), 6.71(t, 3H), 6.89(m, 2H), 7.01(t, 1H), 7.10(t, 1H), 7.37(t, 1H), 7.45(t, 2H), 7.58(bs, 1H), 7.69(d, 2H), 8.10(m, 2H), 8.39(bs, 1H)

Example 53

¹H NMR CDCl₃ δ=0.92(t, 3H), 1.35(m, 4H), 1.71(m, 2H), 1.97(m, 2H), 2.23(s, 3H), 2.55(m, 6H), 2.98(t, 2H), 3.17(t, 4H), 3.32(t, 2H), 3.61(t, 2H), 4.03(t, 2H), 6.03(s, 1H), 6.13(s, 1H), 6.75–6.92(m, 7H), 7.04(t, 1H), 7.14(d, 2H), 7.25(t, 2H), 7.72(s, 1H)

Example 54

¹H NMR CDCl₃ δ=0.89(t, 3H),1.33(m, 4H), 1.65(bs, 2H), 2.15(s, 3H), 2.27(bs, 2H), 3.04(bs, 2H), 3.43(bs, 4H), 3.62 (m, 4H), 3.76(bs, 4H), 4.10(m, 4H), 6.10(s, 2H), 6.69(m, 2H), 6.91(m, 2H), 7.21(m, 2H), 7.36(m, 5H), 7.56(s, 2H), 9.51(s, 1H)

Example 55

¹H NMR CDCl₃ δ=0.90(t, 3H), 1.35(m, 4H), 1.71(m, 2H), 2.05(m, 2H), 2.22(s, 3H), 2.95(m, 2H), 3.48(m, 6H), 3.90(m, 5H), 4.04(t, 2H), 4.50(t, 2H), 4.62(s, 2H), 6.20(s, 1H), 6.34(s, 2H), 6.73(d, 1H), 6.84(d, 1H), 6.98–7.11(m, 4H), 7.37–7.51(m, 5H), 7.73(d, 2H)

Example 56

¹H NMR CDCl₃ δ=0.91(t, 3H), 1.34(m, 4H), 1.68(m, 2H), 1.96(m, 2H), 2.27(s, 3H), 2.51(m, 6H), 3.13(m, 6H), 3.36(t, 2H), 3.53(t, 2H), 3.82(s, 3H), 4.04(t, 2H), 6.56(s, 1H), 6.76(d, 1H), 6.83–6.91(m, 5H), 7.06(t, 1H), 7.19–7.28(m, 6H), 7.76(s, 1H)

Example 57

¹H NMR CDCl₃ δ=0.88(t, 3H), 1.28(m, 4H), 1.58(m, 2H), 1.95(m, 2H), 2.26(s, 3H), 2.49(t, 2H), 2.57(t, 4H), 3.17–3.25 (m, 6H), 3.84(s, 3H), 4.03(t, 2H), 4.35(s, 2H), 6.08(s, 1H), 6.75(d, 1H), 6.85–6.94(m, 5H), 7.04–7.08(m, 3H), 7.17–7.56(m, 4H), 7.56(s, 1H)

Example 58

¹H NMR CDCl₃ δ=0.91(t, 3H), 1.35(m, 4H), 1.71(m, 2H), 1.91(m, 2H), 2.26(s, 3H), 2.48(t, 2H), 2.56(t, 4H), 3.18(t, 4H), 3.34(t, 2H), 3.84(s, 3H), 4.01(t, 2H), 4.58(s, 2H), 6.10(d, 1H), 6.74(d, 1H), 6.85–6.93(m, 4H), 7.02–7.05(m, 2H), 7.16–7.29(m, 6H), 7.80(s, 1H)

Example 59

¹H NMR CDCl₃ δ=0.91(t, 3H), 1.34(m, 4H), 1.69(m, 2H), 1.99(m, 2H), 2.27(s, 3H), 2.55(m, 6H), 3.00(t, 2H), 3.18(m, 4H), 3.26(t, 2H), 3.58(t, 2H), 4.05(t, 2H), 6.07(s, 1H), 6.44(d, 1H), 6.76(d, 1H), 6.82–6.91(m, 4H), 7.04(t, 1H), 7.22–7.34(m, 41), 7.63(d, 2H), 7.71(s, 1H), 7.89(s, 1H)

Example 60

¹H NMR CDCl₃ δ=0.92(t, 3H), 1.35(m, 4H), 1.69(m, 2H), 2.01(m, 2H), 2.25(s, 3H), 2.58(m, 6H), 3.02(t, 2H), 3.17(m, 4H), 3.25(t, 2H), 3.59(t, 2H), 4.05(t, 2H), 6.06(s, 1H), 6.76(d, 1H), 6.83–6.92(m, 4H), 7.04(t, 1H), 7.25(m, 2H), 7.39(d, 2H), 7.61(d, 2H), 8.09(s, 1H), 8.52(s, 1H)

Example 61

¹H NMR CDCl₃ δ=1.09(s, 9H), 1.84(m, 2H), 2.17(s, 3H), 2.44(t, 2H), 2.56(t, 4H), 3.19(t, 4H), 3.31(s, 2H), 3.89(s, 3H), 3.95(t, 2H), 4.72(s, 2H), 6.25(s, 1H), 6.70–7.05(m, 6H), 7.17–7.30(m, 7H), 7.75(s, 1H)

Example 62

¹H NMR CDCl₃ δ=1.11(s, 9H), 2.19(s, 3H), 2.35(m, 2H), 3.38(m, 2H), 3.52(s, 2H), 3.68–3.91(m, 7H), 4.11(m, 4H), 4.32(t, 2H), 4.72(s, 2H), 6.59(bs, 1H), 6.65(d, 1H), 6.77(d, 1H), 6.98(t, 2H), 7.32–7.54(m, 9H), 10.10(s, 1H)

Example 63

¹H NMR CDCl₃ δ=0.92(t, 3H), 1.34(m, 4H), 1.67(m, 2H), 1.98(m, 2H), 2.24(s, 3H), 2.50–2.60(m, 6H), 3.03(t, 2H), 3.18(t, 4H), 3.26(t, 2H), 3.60(t, 2H), 4.04(t, 2H), 6.07(s, 1H), 6.74(d, 1H), 6.83–6.93(m, 4H), 7.05(t, 1H), 7.19–7.29(m, 7H), 7.41(t, 1H), 7.85(s, 1H)

Example 4
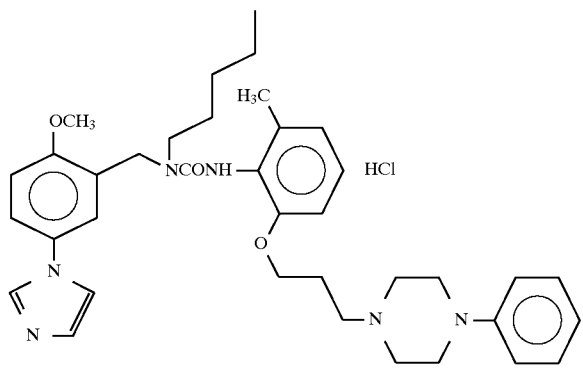
Example 5
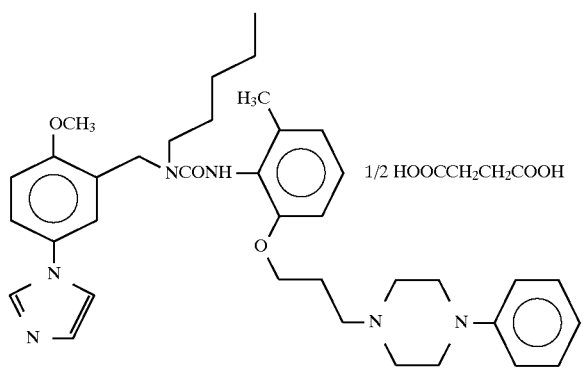
Example 6
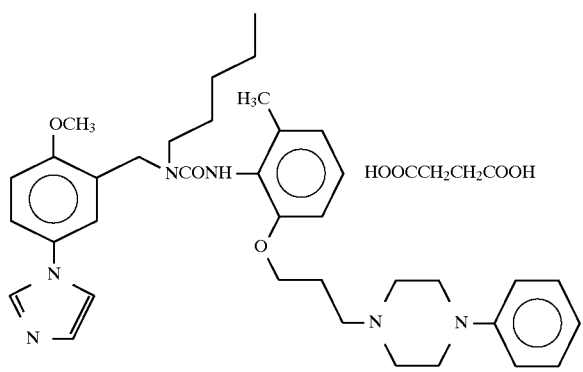
Example 7
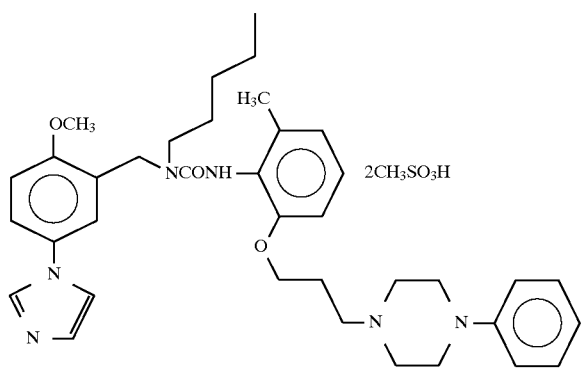

Example 8
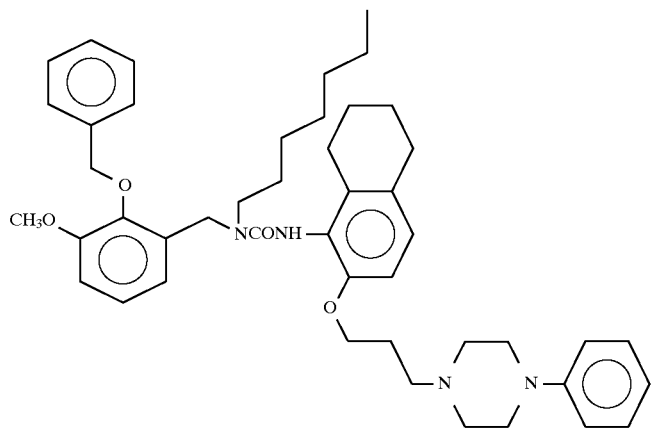
Example 9
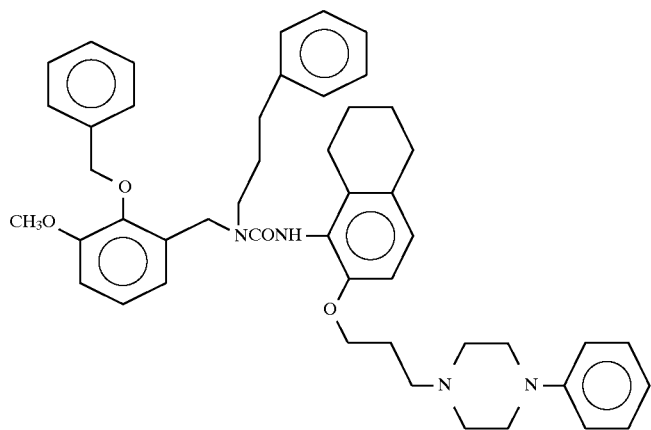
Example 10
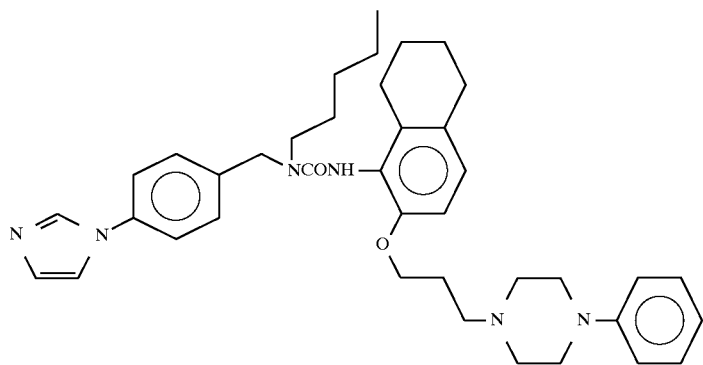

Example 11
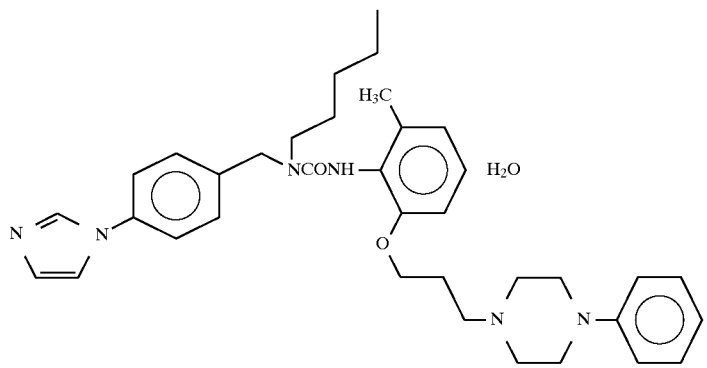
Example 12
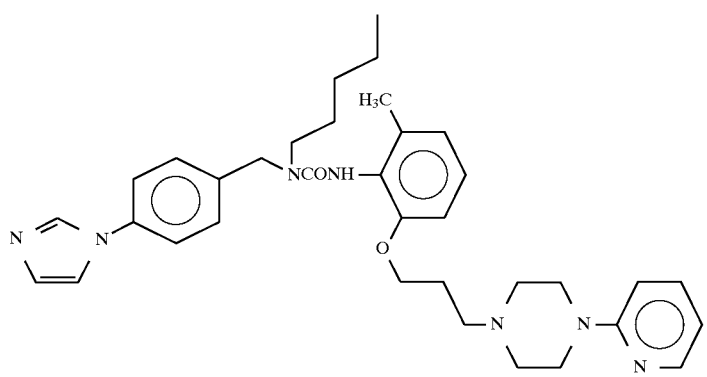
Example 13
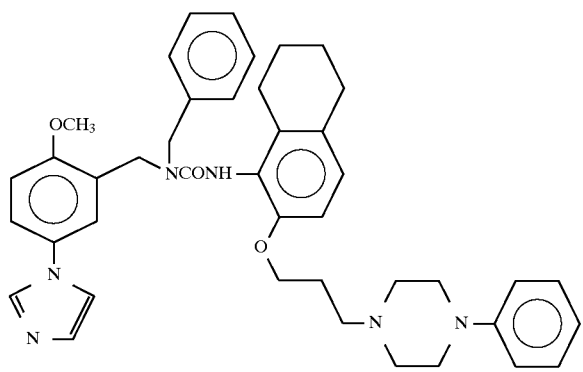
Example 14
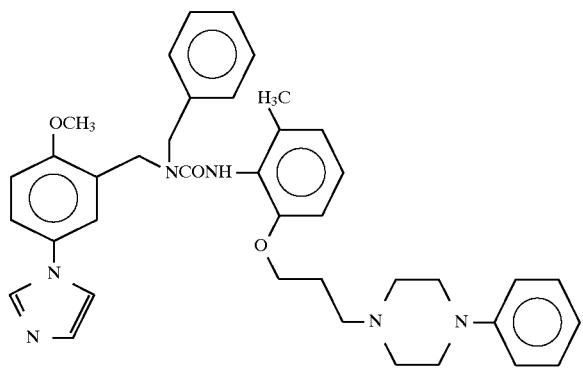

Example 15
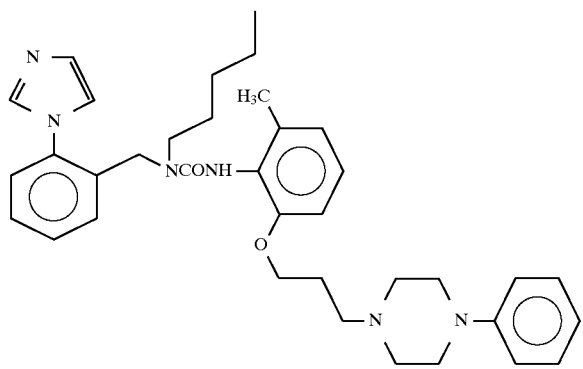
Example 16
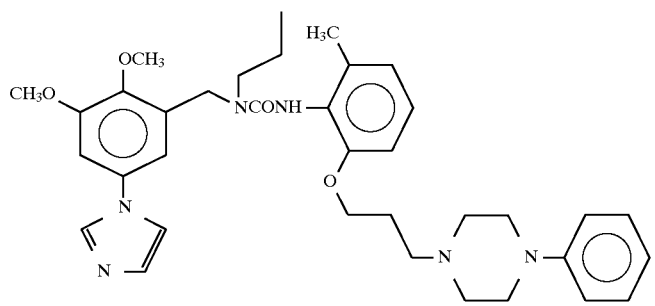
Example 17
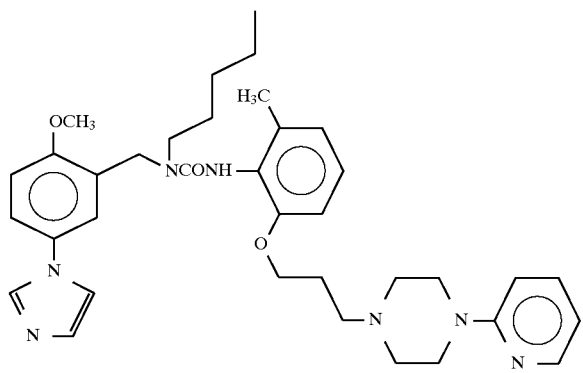
Example 18
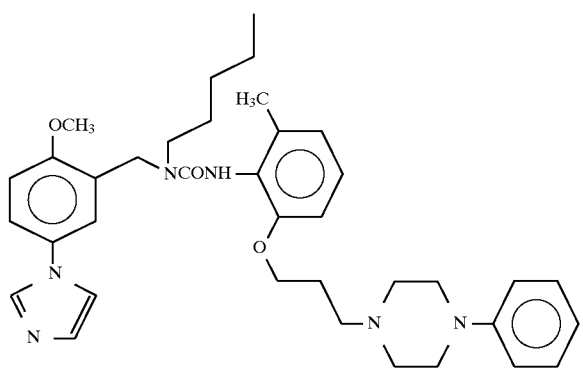

Example 19
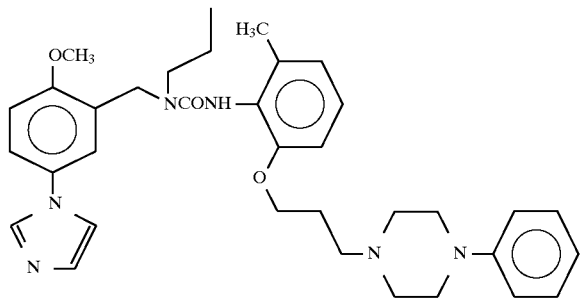
Example 20
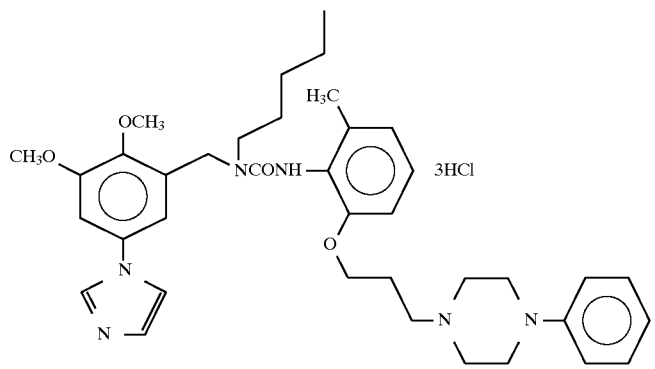
Example 21
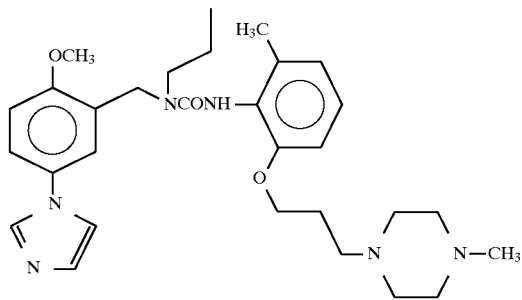
Example 22
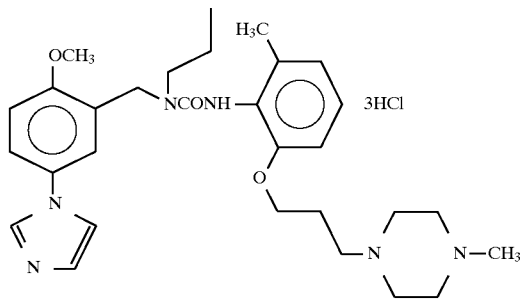

Example 23
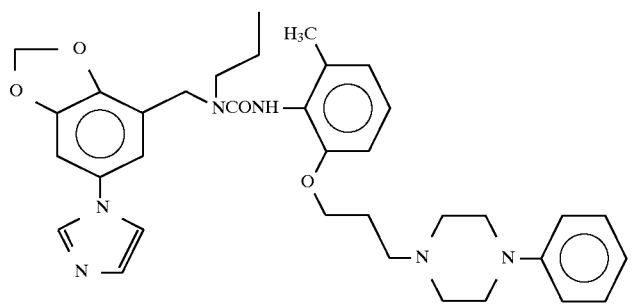
Example 24
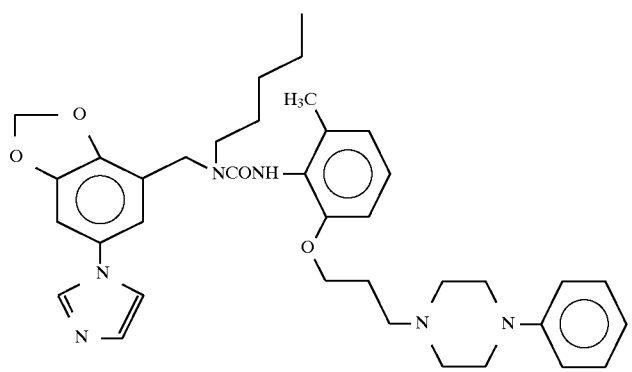
Example 25
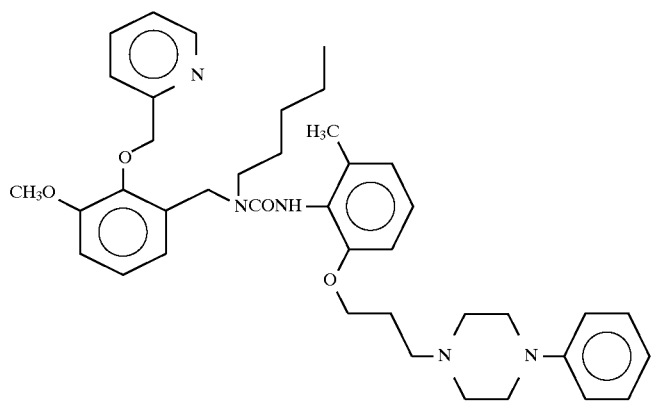
Example 26
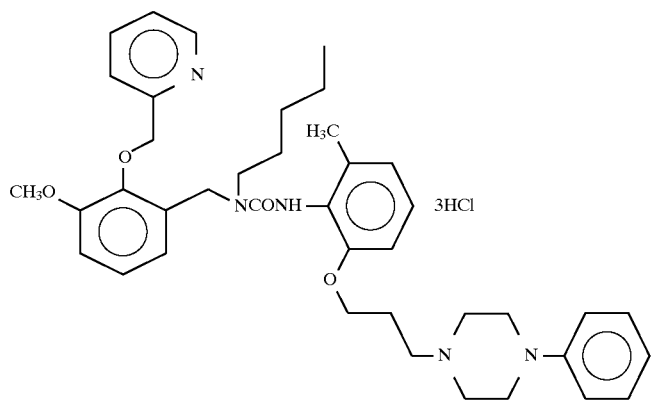

-continued
Example 27
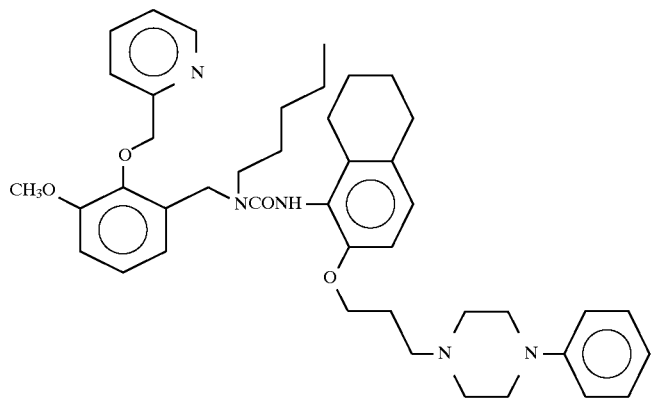
Example 28
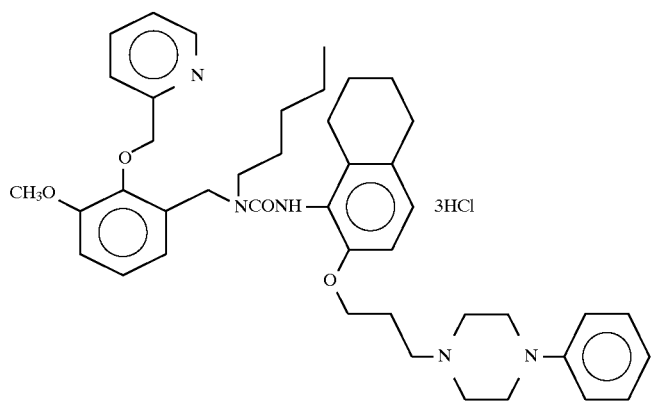
Example 29
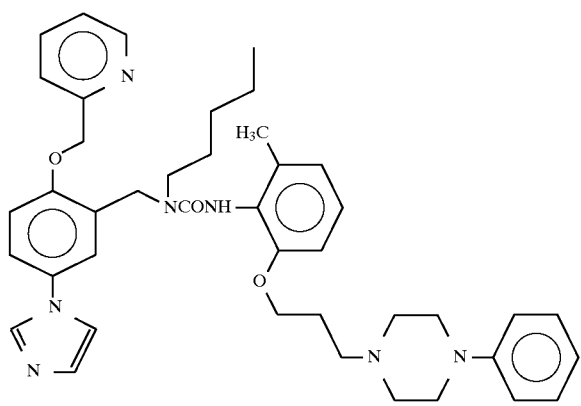

-continued
Example 30
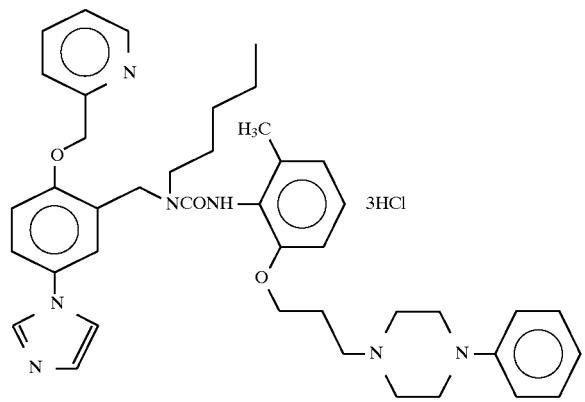
Example 31
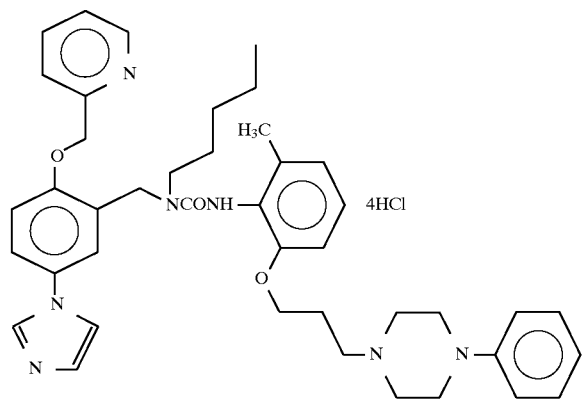
Example 32
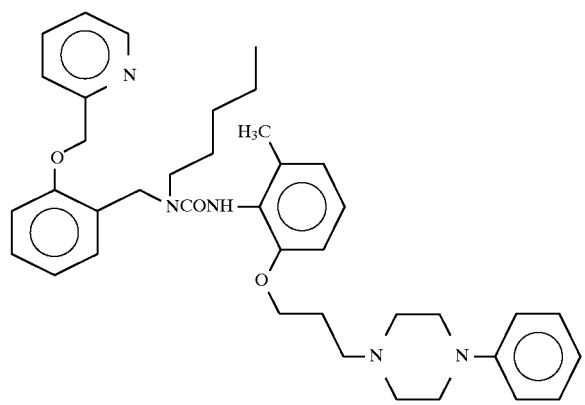

Example 33
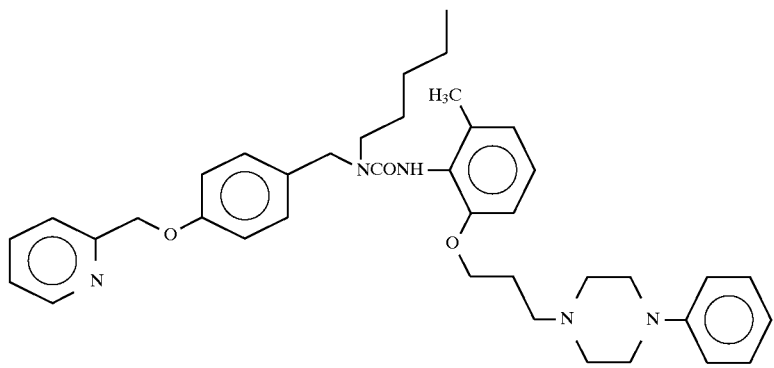
Example 34
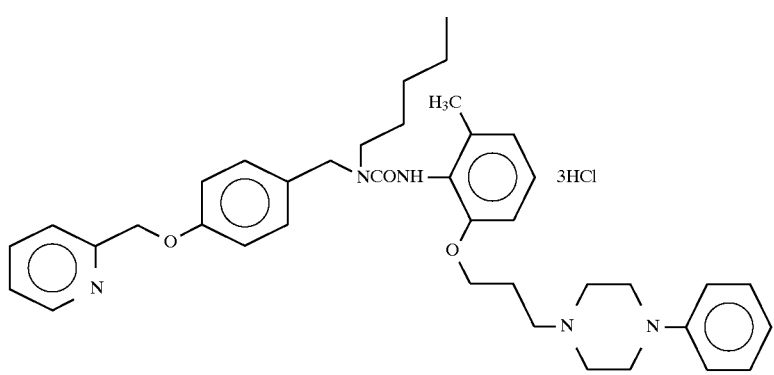
Example 35
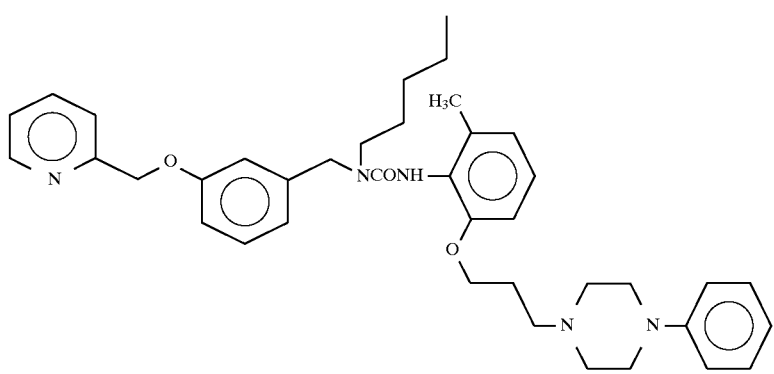
Example 36
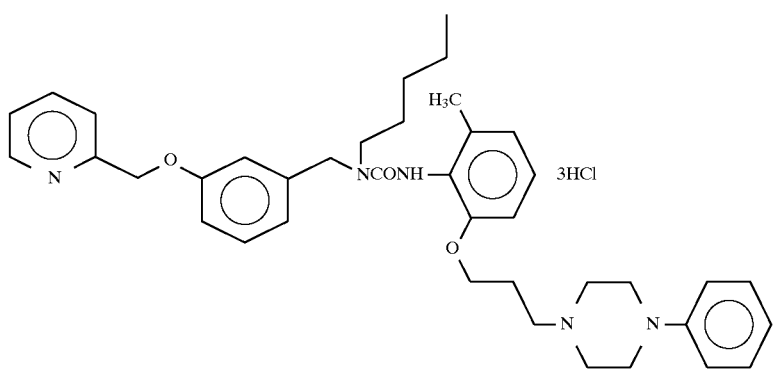

Example 37
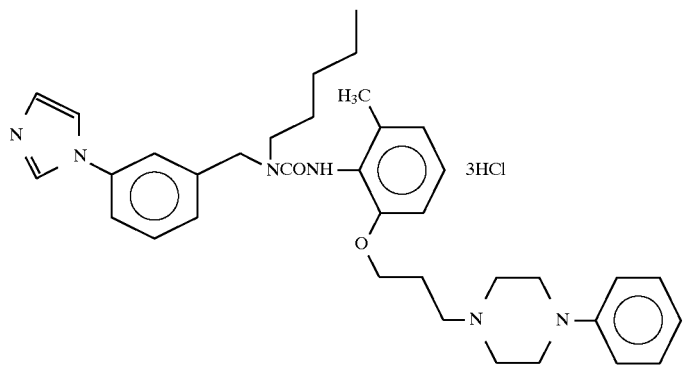
Example 38
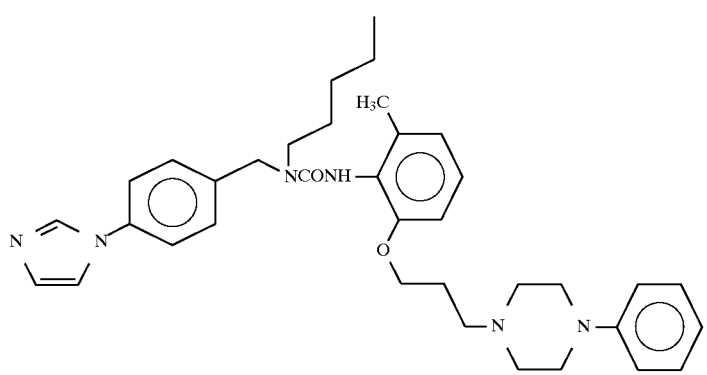
Example 39
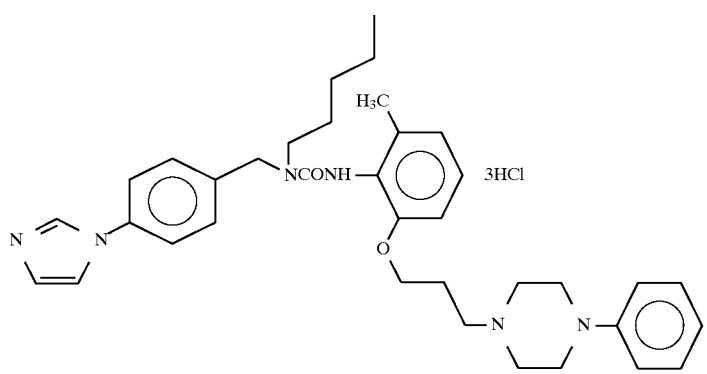
Example 40
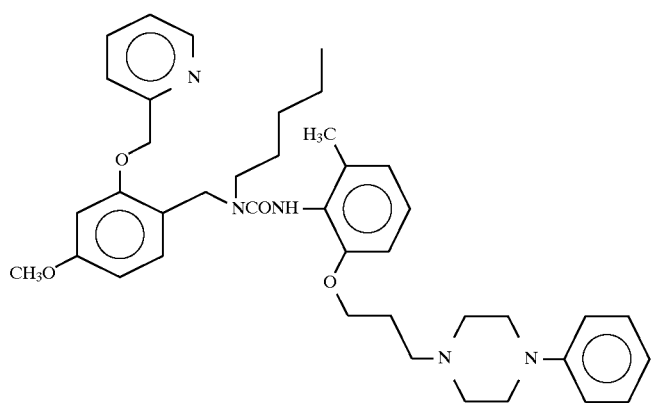

Example 41
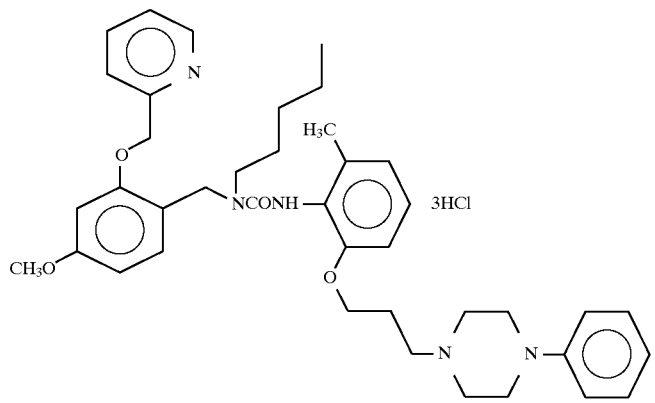
Example 42
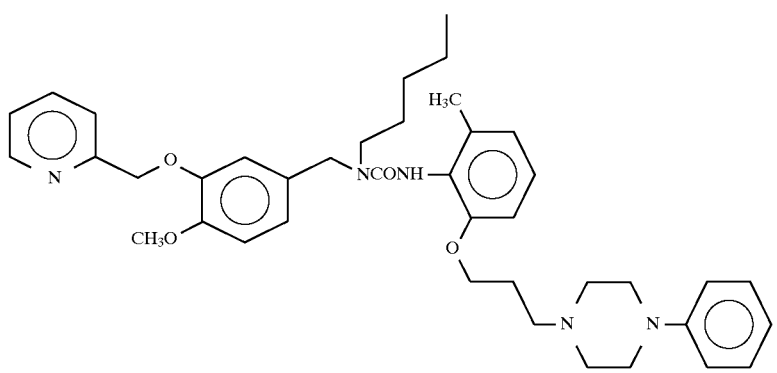
Example 43
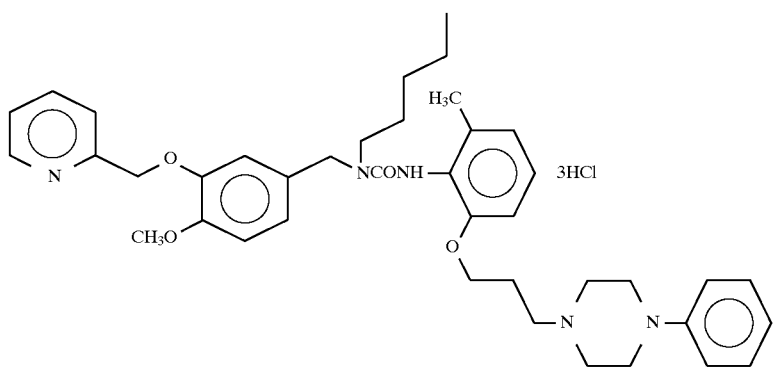
Example 44
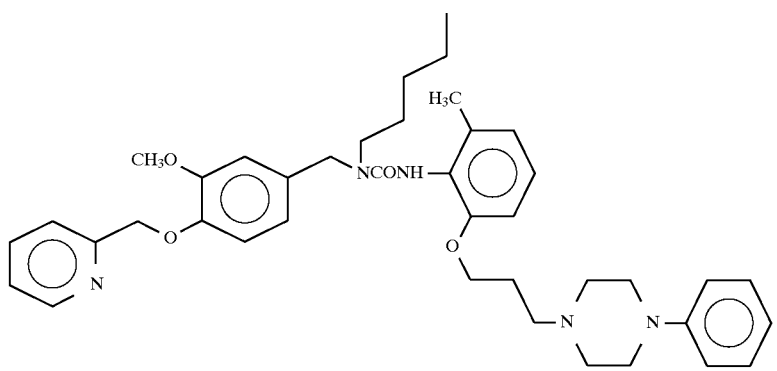

Example 45
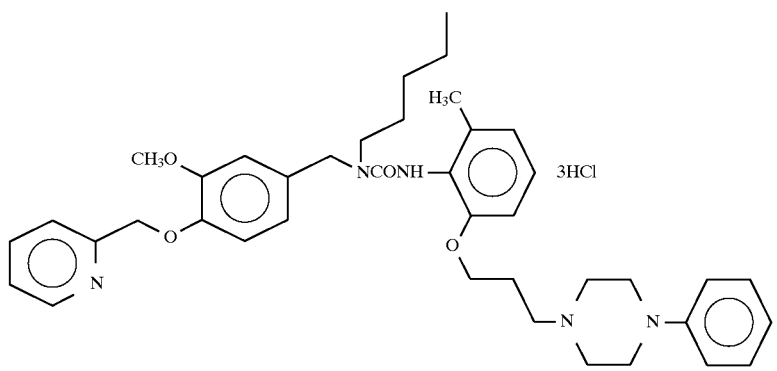
Example 46
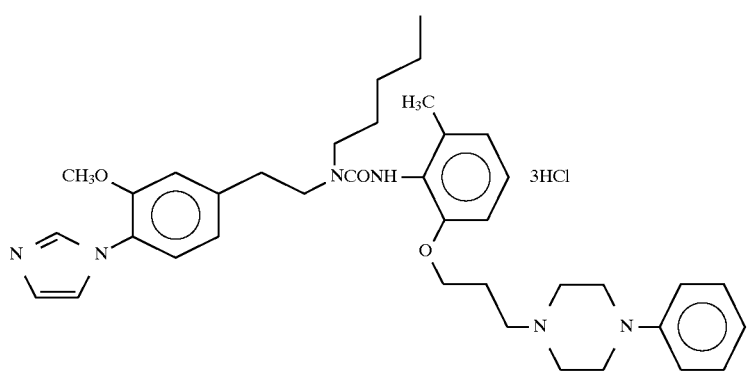
Example 47
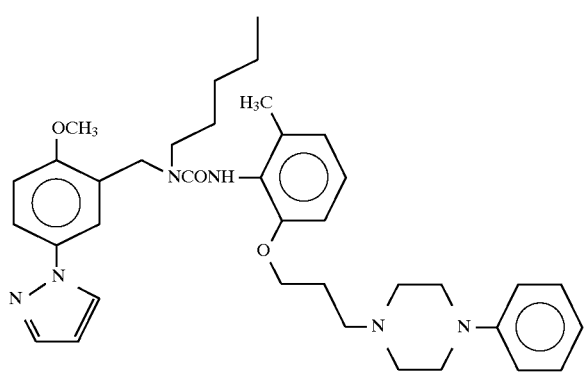
Example 48
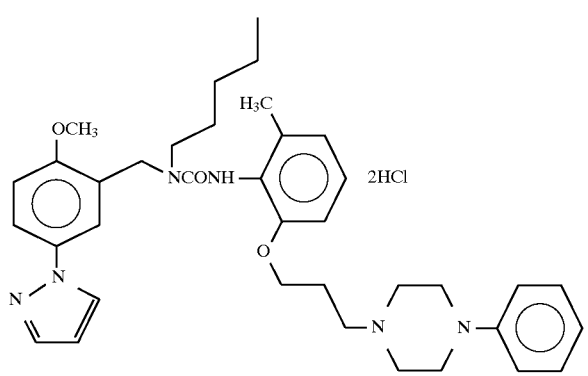

Example 49
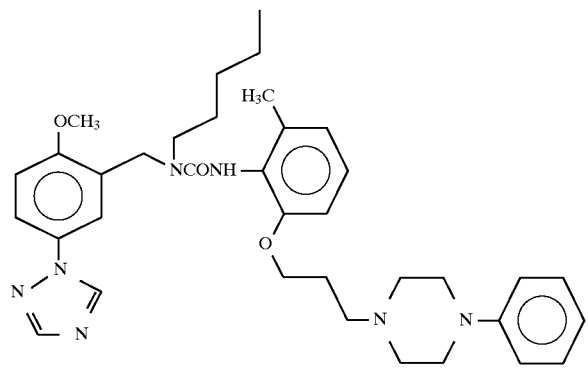
Example 50
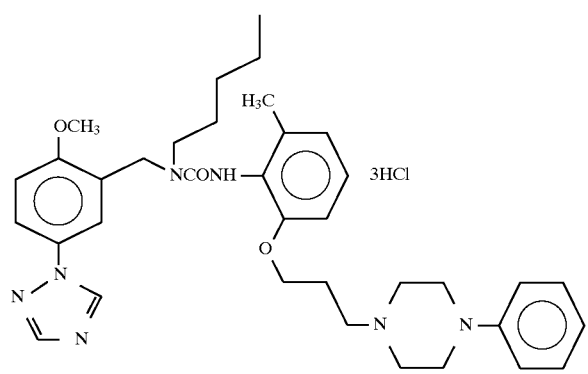
Example 51
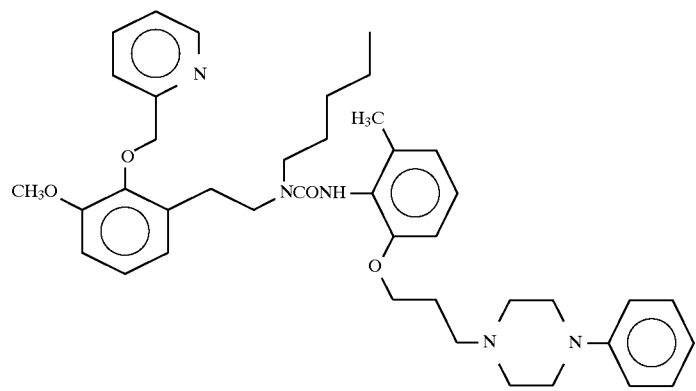

Example 52
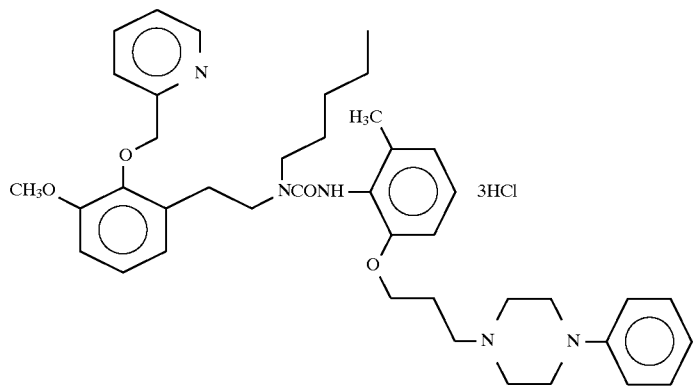
Example 53
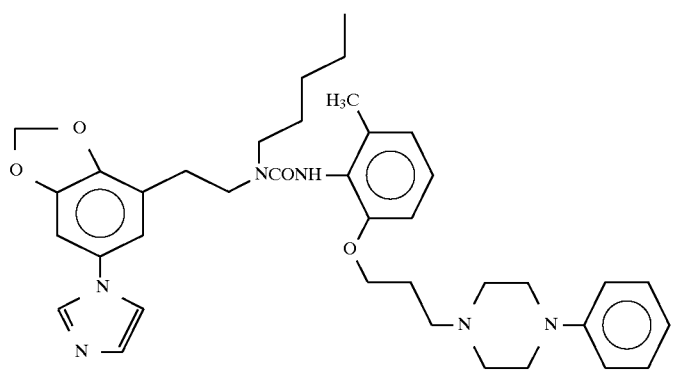
Example 54
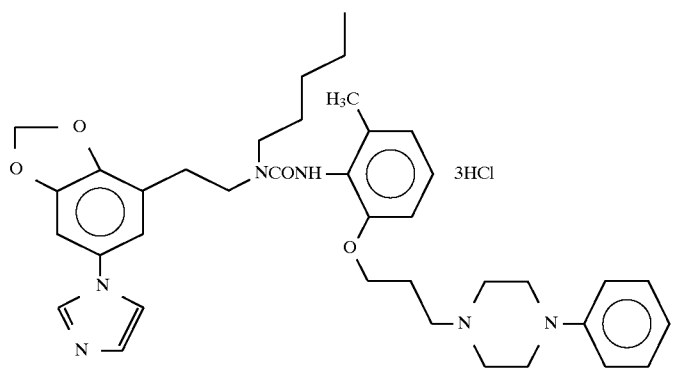
Example 55
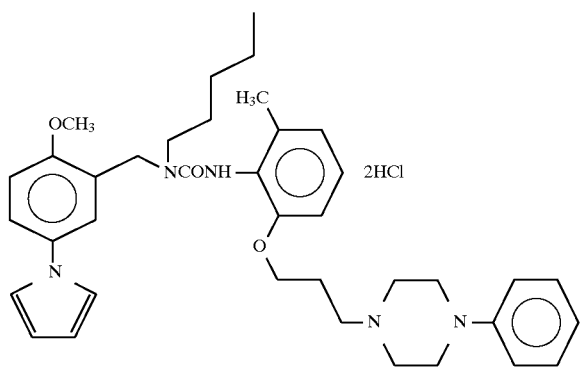

Example 56
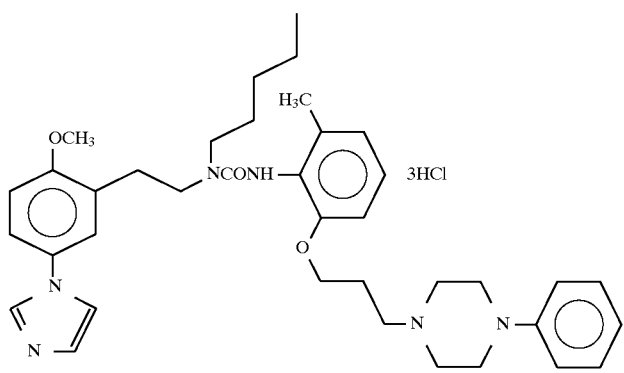
Example 57
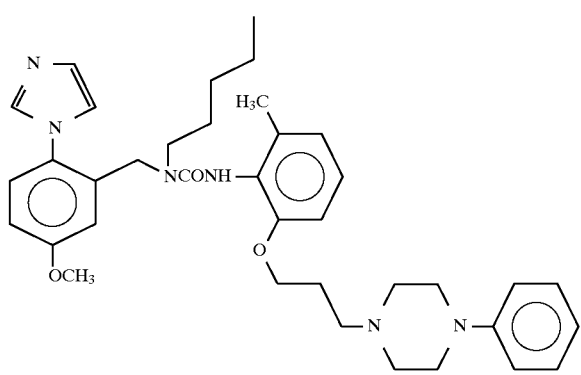
Example 58
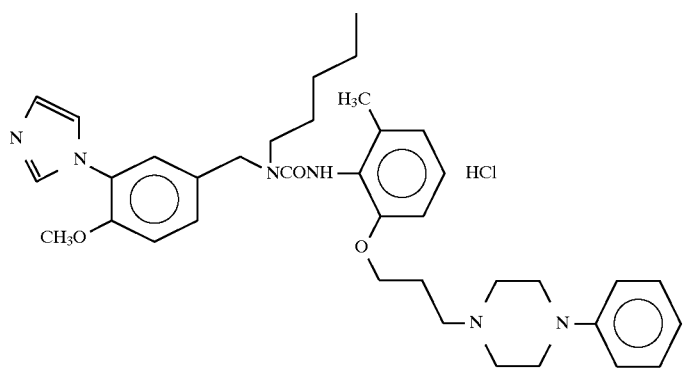
Example 59
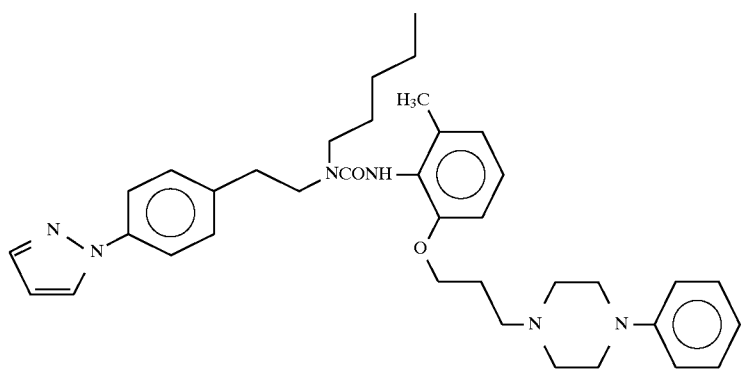

Example 60
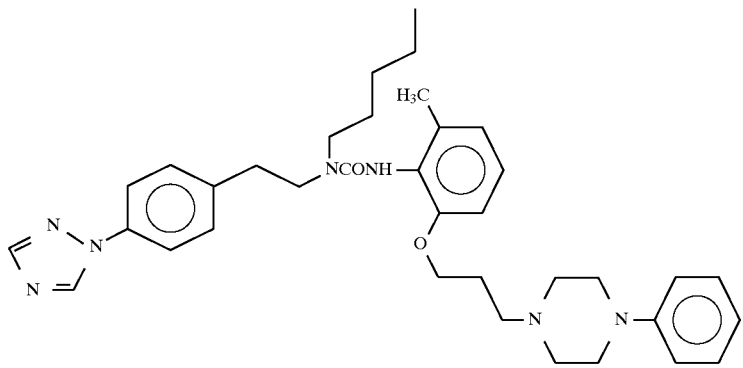
Example 61
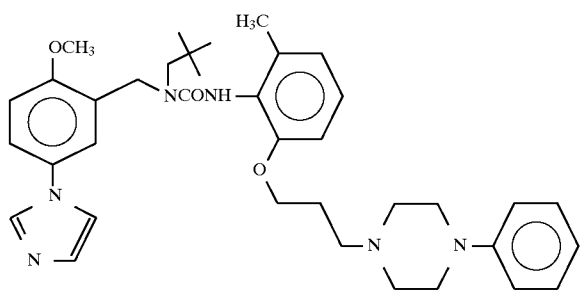
Example 62
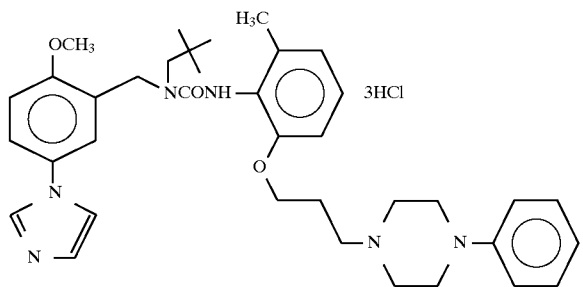
3HCl
Example 63
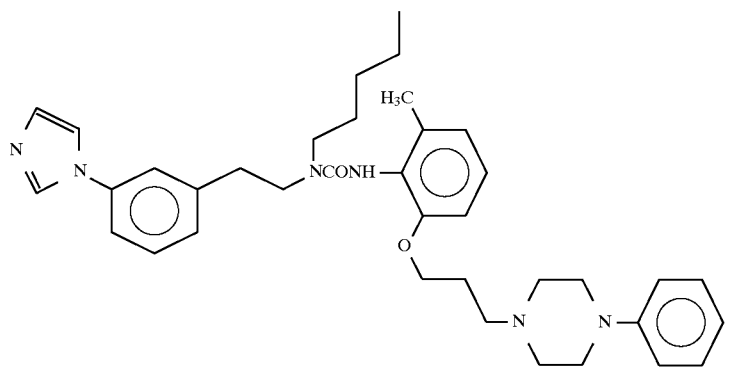

Example 64

Preparation of the Compound:

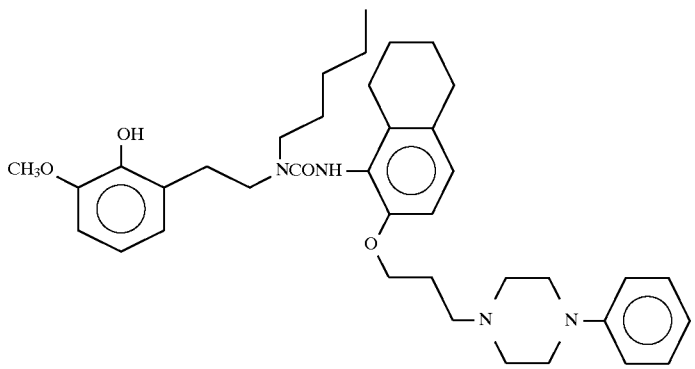

Methylene chloride (60 ml) was added to 1-amino-5,6,7,8-tetrahydro-2-{3-(4-phenyl-1-piperazyl)propoxy}naphthalene (2.16 g, 5.91 mmol), and then the mixture was added with bis(trichlorometh yl) carbonate (0.75 g, 2.53 mmol) and triethylamine (1.62 g, 16 mmol) with stirring under ice cooling. After the mixture was refluxed with stirring for 1.5 hours, the mixture was cooled to room temperature and added with N-heptyl-2-(2-benzyloxy-3-methoxyphenyl) ethylamine (2.16 g, 6.08 mmol), and then allowed to react overnight. A part of the solvent was evaporated and the residual mixture was purified by silica gel chromatography (Wako Gell C-300: 150 g, eluent: ethyl acetate/hexane=1:1) to give N-{2-(2-benzyloxy-3-methoxy)phenyl}ethyl-N-(1-heptyl)-N'-[5,6,7,8-tetrahydro-2-{3-(4-phenyl-1-piperazinyl)propoxy}naphthyl]urea. Ethanol (120 ml) and 10% palladium/carbon (0.45 g) were added to the product, and hydrogenation was carried out at 50° C. for 6 hours. After the catalyst was removed by filtration, the solvent was evaporated, and the residue was purified by silica gel chromatography (Wako Gell C-300: 150 g, eluent: chloroform/methanol=100/1) to give N-{2-(2-hydroxy-3-methoxyphenyl)ethyl}-N-(1-heptyl)-N'-[5,6,7,8-tetrahydro-2-{3-(4-phenyl-1-piperazinyl)propoxy}naphthyl]urea (1.0 g).

¹HNMR(CDCl₃): δ=0.88(t, 3H), 1.30(m, 8H), 1.63–1.74 (m, 4H), 1.96(m, 2H), 2.51(m, 6H), 2.72(bs, 4H), 3.01–3.14 (m, 6H), 3.37(t, 2H), 3.51(t, 2H), 3.84(s, 3H), 4.01(t, 2H), 6.57(bs, 1H), 6.67–6.91(m, 8H), 7.26(m,2H)

Example 65

Preparation of the compound:

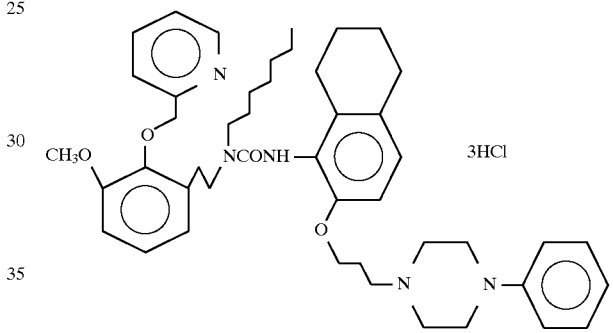

Potassium carbonate (1.0 g, 7.2 mmol), 2-chloromethylpyridine hydrochloride (0.56 g, 3.4 mmol), and N,N-dimethylformamide (30 ml) were added to N-{2-(2-hydroxy-3-methoxy)phenyl}ethyl-N-(1-heptyl)-N'-[5,6,7,8-tetrahydro-2-{3-(4-phenyl-1-piperazinyl)propoxy}naphthyl]urea (1.0 g, 1.5 mmol) and the mixture was stirred at 100° C. for 12 hours. After cooling, the reaction mixture was added with water and extracted with ethyl acetate. The organic layer was washed with saturated brine and dried over anhydrous magnesium sulfate, and then the solvent was evaporated. The residue was purified by silica gel chromatography (Wako Gell C-300: 80 g, eluent: ethyl acetate) to give N-[2-{2-(2-pyridylmethyloxy)-3-methoxyphenyl}ethyl]-N-(1-heptyl)-N'-[5,6,7,8-tetrahydro-2-{3-(4-phenyl-1-piperazinyl)naphthyl}]urea. The product was added with methyl alcohol and concentrated hydrochloric acid (0.15 ml, 1.7 mmol), and after the solvent was removed, the residue was crystallized from ether to give N-[2-{2-(2-pyridylmethyloxy)-3-methoxy}phenyl]ethyl-N-(1-heptyl)-N'-[5,6,7,8-tetrahydro-2-{3-(4-phenyl-1-piperazinyl)propoxy}naphthyl}urea trihydrochloride (0.23 g).

$^1$HNMR(CDCl$_3$): δ=0.86(t, 3H), 1.27(m, 8H), 1.57–1.67(m, 6H), 2.37(m, 2H), 2.52(bs, 2H), 2.64(bs, 2H), 3.14(t, 2H), 3.36(t, 2H), 3.47–3.64(m, 6H), 3.79(s, 3H), 3.83(bs, 4H), 4.15(bs, 2H), 4.35(bs, 2H), 5.62(s, 2H), 6.46(s, 1H), 6.62(d, 1H), 6.83–6.91(m, 3H), 7.10(s, 1H), 7.28(m, 1H), 7.31–7.56(m, 5H), 8.06(bs, 2H), 8.50(d, 1H)

Compounds of Examples 66 through 71 set out below were synthesized in the same manner as those of Examples 64 and 65.

Example 66

$^1$H NMR CDCl$_3$ δ=0.86(t, 3H), 1.28(m, 8H), 1.72(m, 6H), 1.88(t, 2H), 2.43(t, 2H), 2.54(t, 4H), 2.68(m, 4H), 3.17(t, 4H), 3.41(t, 2H), 3.93(t, 2H), 4.73(s, 2H), 5.25(s, 2H), 6.06(s, 1H), 6.64(d, 1H), 6.84–6.95(m, 6H), 7.02(t, 1H), 7.17–7.29(m, 3H), 7.38(d, 1H), 7.49(d, 1H), 7.69(t, 1H), 8.57(d, 1H)

Example 67

$^1$H NMR CDCl$_3$ δ=1.72–1.84(m, 6H), 2.01(m, 2H), 2.39(t, 2H), 2.48(t, 4H), 2.62–2.70(m, 6H), 3.12(t, 4H), 3.49(t, 2H), 3.91(t, 2H), 4.72(s, 2H), 5.24(s, 2H), 6.06(s, 1H), 6.65(d, 1H), 6.84–6.95(m, 6H), 7.02(t, 1H), 7.16–7.33(m, 9H), 7.47(d, 1H), 7.64(t, 1H), 8.56(d, 1H)

Example 68

$^1$H NMR CDCl$_3$ δ=0.93(t, 3H), 1.70(m, 6H), 1.85(m, 2H), 2.44(t, 2H), 2.54(t, 4H), 2.64–2.70(m, 4H), 3.17(t, 4H), 3.39(t, 2H), 3.93(t, 2H), 4.73(s, 2H), 5.25(s, 2H), 6.07(s, 1H), 6.65(d, 1H), 6.84–6.95(m, 5H), 7.03(t, 1H), 7.20–7.29(m, 4H), 7.38(d, 1H), 7.50(d, 1H), 7.67(d, 1H), 8.56(d, 1H)

Example 69

$^1$H NMR CDCl$_3$ δ=0.94(t, 3H), 1.72(m, 6H), 1.86(m, 2H), 2.44(t, 2H), 2.55(t, 4H), 2.64–2.71(m, 4H), 3.18(t, 4H), 3.39(t, 2H), 3.94(t, 2H), 4.71(s, 2H), 5.13(s, 2H), 6.03(s, 1H), 6.67(d, 1H), 6.85–6.94(m, 7H), 7.04(t, 1H), 7.23–7.38(m, 4H), 8.60(m, 2H)

Example 70

$^1$H NMR CDCl$_3$ δ=0.91(t, 3H), 1.70(m, 6H), 1.88(m, 2H), 2.47(t, 2H), 2.57(m, 6H), 2.70(m, 2H), 3.19(t, 4H), 3.36(t, 2H), 3.94(t, 2H), 4.64(s, 2H), 5.11(s, 2H), 6.00(s, 1H), 6.66(d, 1H), 6.84–6.98(m, 5H), 7.08(t, 1H), 7.23–7.30(m, 4H), 7.42(d, 1H), 7.79(d, 1H), 8.60(m, 1H), 8.68(d, 1H)

Example 71

$^1$H NMR CDCl$_3$ δ=1.72(m, 4H), 1.85(m, 2H), 2.43(t, 2H), 2.53(t, 4H), 2.68(m, 4H), 3.10(s, 3H), 3.16(t, 4H), 3.93(t, 2H), 4.74(s, 2H), 5.25(s, 2H), 6.17(s, 1H), 6.65(d, 1H), 6.85–6.97(m, 5H), 7.03(t, 1H), 7.18–7.36(m, 5H), 7.48(d, 1H), 7.64(t, 1H), 8.54(d, 1H)

Example 72

$^1$H NMR DMSO-d$_6$ δ=1.39–1.60(m, 6H), 1.93(m, 2H), 2.10(m, 5H), 3.21–3.48(m, 10H), 3.91(s, 3H), 4.00(t, 2H), 4.44(s, 2H), 4.58(q, 1H), 6.76–7.05(m, 6H), 7.21–7.36(m, 4H), 7.61–7.67(m, 2H), 7.92(s, 1H), 8.06(s, 1H), 9.62(s, 1H)

Example 73

$^1$H NMR DMSO-d$_6$ δ=0.94(d, 6H), 2.06(m, 6H), 3.05–3.80(m, 12H), 3.89(s, 3H), 3.97(t, 2H), 4.56(s, 2H), 6.76–7.05(m, 6H), 7.27(m, 3H), 7.40(d, 1H), 7.69(s, 1H), 7.70(m, 1H), 7.96(s, 1H), 8.16(s, 1H), 9.76(s, 1H)

Example 74

$^1$H NMR DMSO-d$_6$ δ=1.14(m, 6H), 2.07(m, 5H), 3.11–3.78(m, 10H), 3.91(s, 3H), 3.99(t, 2H), 4.44(s, 2H), 4.56(m, 1H), 6.76–6.89(m, 3H), 6.99–7.05(m, 3H), 7.22–7.29(m, 3H), 7.44(d, 1H), 7.54(s, 1H), 7.64–7.67(m, 1H), 7.95(s, 1H), 8.11(s, 1H), 9.68(s, 1H)

Example 75

$^1$H NMR DMSO-d$_6$ δ=1.48(s, 9H), 2.19(m, 5H), 3.13–3.74(m, 10H), 3.91(s, 3H), 4.09(m, 4H), 6.80–6.87(m, 2H), 6.94(d, 2H), 7.04(t, 1H), 7.23(t, 2H), 7.31(d, 1H), 7.85(d, 1H), 7.92(s, 1H), 8.29(t, 2H), 9.36(bs, 2H), 9.72(s, 1H)

Examples 66

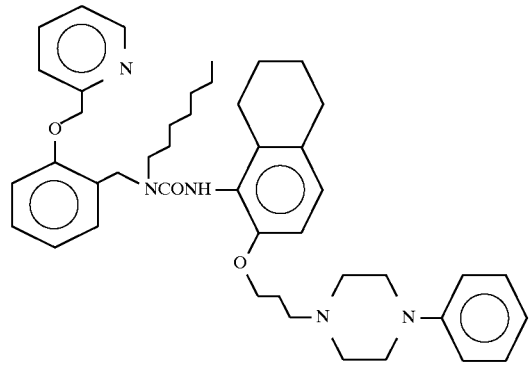

Examples 67

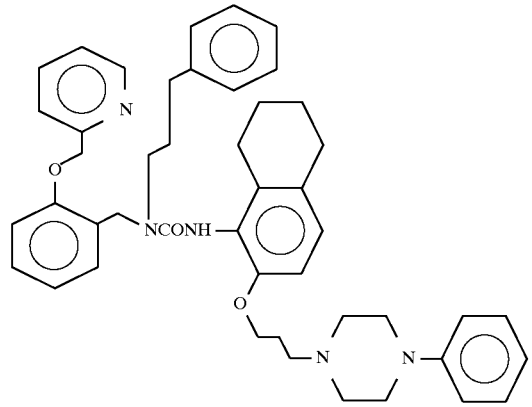

Examples 68

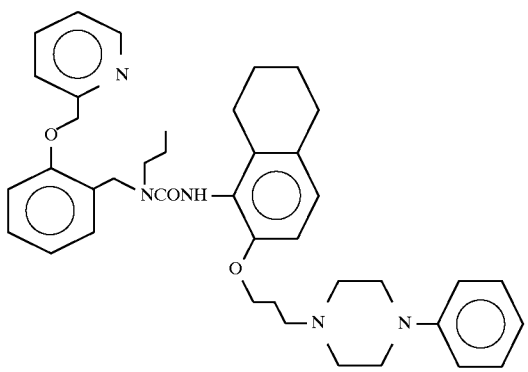

Example 72

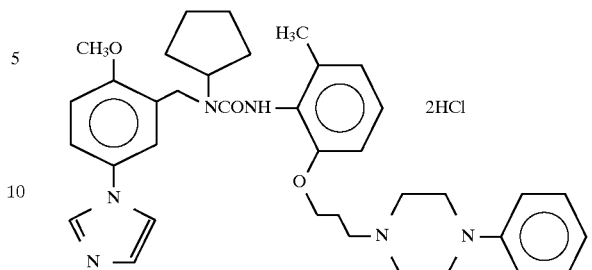

Examples 69

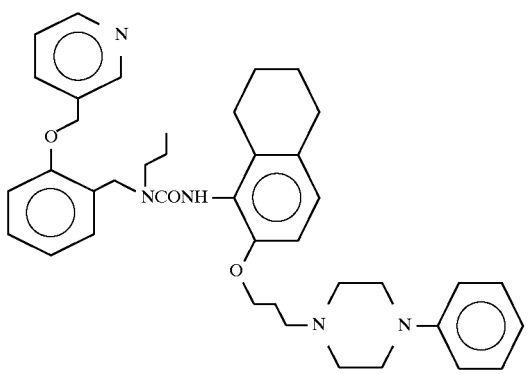

Example 73

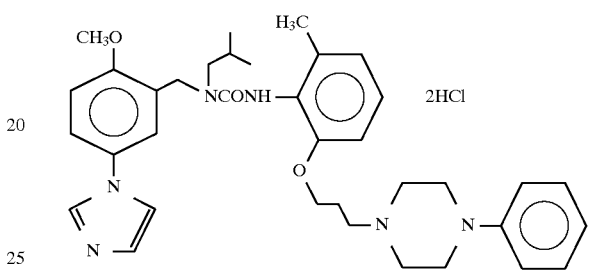

Example 74

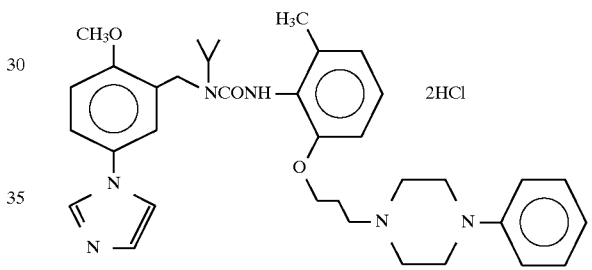

Examples 70

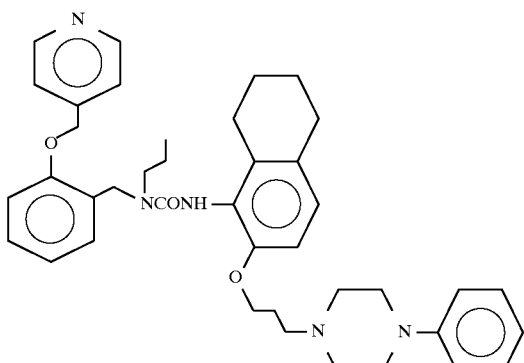

Example 75

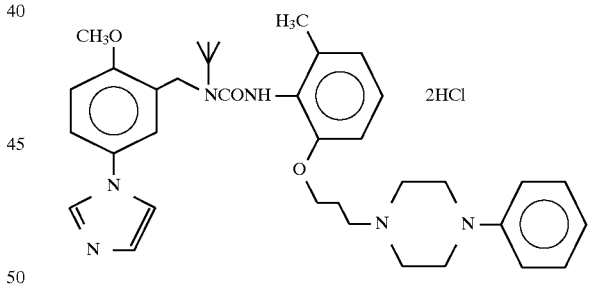

Examples 71

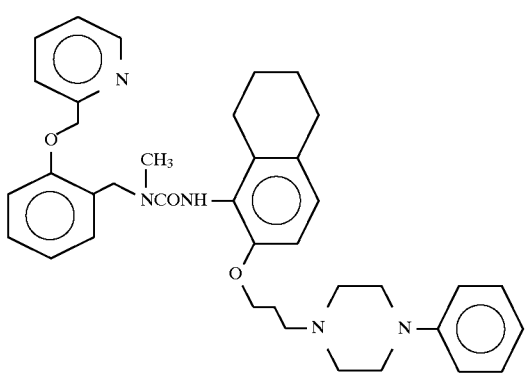

TEST EXAMPLES

Test Example 1

Inhibitory Activity against ACAT of HepG2 cells Derived from Human Liver Cancer Cells Inhibitory activities of the compounds of the present invention against ACAT were measured by the method described below. HepG2 cells derived from human liver cancer cells were used for the measurement of the ACAT activity. A complex of radio-labelled oleic acid and bovine serum albumin was added to a culture of the cells, and the activity was measured by observing the amount of radio-labelled cholesterol oleate produced from the radio-labelled oleic acid in the cells. The inhibitory activity of the compounds of the present invention against ACAT was measured as follows: percent reduction rates of enzymatic activity by the addition of given concentrations of test compounds were observed on the basis of the amount of the produced cholesterol oleate in the control group without the addition of a test compound, and by using the results, $IC_{50}$, i.e., concentrations of tested compounds required to inhibit 50% of the enzyme activity, was calculated. The results are summarized in Table 2.

Test Example 2

Inhibitory Activity against ACAT Derived from Foamed Macrophages

Inhibitory activity of the compounds of the present invention against ACAT in foamed macrophages was measured by the methods set out below. Acetylated low density lipoprotein was added to macrophages taken from abdominal cavities of ddY female mice and the cells were incubated for 24 hours to obtain foaming macrophages. These cells accumulated a large amount of cholesterol (ester) inside the cells, and are used as a model of arteriosclerosis lesion. ACAT activity of the cells was determined by adding a complex of radio-labelled oleic acid and bovine serum albumin to the cell culture, and observing the amount of radio-labelled cholesterol oleate that was produced from the radio-labelled oleic acid in the cells. The inhibitory activities of the compounds of the present invention against ACAT were measured as follows: percent reduction rates of enzymatic activity by the addition of given concentrations of test compounds was observed on the basis of the amount of the produced cholesterol oleate in the control group without the addition of a test compound, and by using the results, $IC_{50}$, i.e., concentrations of tested compounds required to inhibit 50% of the enzyme activity, was calculated. The results are summarized in Table 2.

TABLE 2

| Example No. | Inhibitory activity against ACAT ($\mu$M) | |
| --- | --- | --- |
| | HepG2 | Macrophage |
| 1 | 0.128 | |
| 2 | 0.101 | 0.131 |
| 3 | 0.108 | |
| 8 | 0.414 | |
| 9 | 0.366 | |
| 10 | 0.389 | |
| 11 | 0.189 | |
| 12 | 0.595 | |
| 13 | 0.067 | |
| 14 | 0.240 | |
| 15 | 0.516 | |
| 17 | 0.363 | |
| 18 | 0.164 | 0.440 |
| 19 | 0.156 | |
| 20 | 0.851 | |
| 23 | 0.634 | |
| 24 | 0.449 | |
| 26 | 0.743 | |
| 28 | 0.732 | |
| 30 | 0.234 | |
| 31 | 0.138 | |
| 32 | 0.600 | |
| 34 | 0.089 | 0.119 |
| 36 | 0.270 | |
| 37 | 0.220 | |
| 38 | 0.282 | |
| 40 | 0.320 | |
| 44 | 0.400 | |

TABLE 2-continued

| Example No. | Inhibitory activity against ACAT ($\mu$M) | |
| --- | --- | --- |
| | HepG2 | Macrophage |
| 46 | 0.076 | |
| 47 | 0.081 | |
| 49 | 0.045 | |
| 53 | 0.606 | |
| 55 | 0.483 | |
| 56 | 0.054 | |
| 57 | 0.220 | |
| 58 | 0.584 | 1.055 |
| 67 | 0.124 | |
| 68 | 0.187 | |
| 69 | 0.289 | |
| 70 | 0.631 | |
| 71 | 0.635 | |
| 72 | 0.262 | |
| 73 | 0.458 | |
| 74 | 0.386 | |

Test Example 3

Cholesterol Reduction Activity in High Cholesterol Fed Rats

6-Week old WISTAR male rats were fed with high cholesterol solid feedstuff (Oriental Kobo Co., Ltd., 1% cholesterol, 0.5% cholic acid). Each group consisted of seven rats was compulsorily administered with 0.2% aqueous solution of a test compound (compound of Example 3) once a day at a dose of 1 mg/kg, 3 mg/kg, 10 mg/kg, or 30 mg/kg for 5 days. One group consisted of seven rats was fed with the same high cholesterol feedstuff and used as a control group. After 3.5 hours from the final administration, blood was collected from the abdominal aorta and the total cholesterol in the serum was measured. The reduction rate of total cholesterol was represented as a ratio between a control group not administered with the drug (seven rats) and examined by the probit analysis. The results are shown in Table 3.

TABLE 5

| Total cholesterol reduction rate | Dose of test compound (compound of Example 3) |
| --- | --- |
| 10% | 1.9 mg/kg |
| 20% | 3.6 mg/kg |
| 25% | 4.6 mg/kg |
| 30% | 5.7 mg/kg |
| 50% | 12.1 mg/kg |

The compounds of the present invention have excellent inhibitory activity against ACAT, and thus, they are useful as active ingredients of the medicines for preventive and/or therapeutic treatment of hyperlipemia, and preventive and/or therapeutic treatment of atherosclerosis.

What is claimed is:

1. A member selected from the group consisting of a compound represented by the following formula (I):

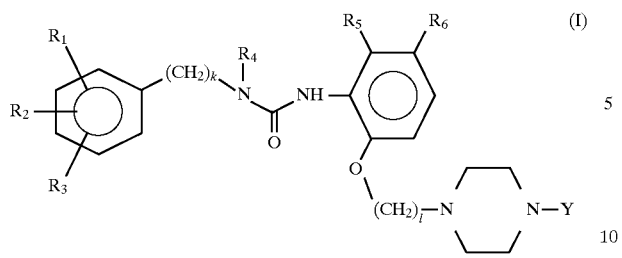

a pharmaceutically acceptable salt thereof, a hydrate of said compound or salt and a solvate of said compound or salt thereof, wherein $R_1$, $R_2$ and $R_3$ represent independently hydrogen atom, hydroxyl group, a $C_1$–$C_3$ alkoxy group, Het-$(CH_2)_m$—O— in which Het represents a heterocyclic group containing 1 or 2 nitrogen atoms and having 5 or 6 ring-membered atoms and m represents an integer of 1 to 3, a $C_7$–$C_9$ aralkyloxy group, or a heterocyclic group containing 1 to 4 nitrogen atoms and 5 or 6 ring-membered atoms, alternatively, $R_1$ and $R_2$ may form together to represent —O—$(CH_2)_n$—O— in which n represents an integer of 1 to 3;

$R_4$ represents a $C_1$–$C_7$ alkyl group, a $C_3$–$C_7$ cycloalkyl group or Ar—$(CH_2)_p$— in which Ar represents a $C_6$–$C_{10}$ aryl group and p represents an integer of 1 to 3;

$R_5$ and $R_6$ represent independently hydrogen atom or a $C_1$–$C_3$ alkyl group, alternatively, $R_5$ and $R_6$ may form together to represent —$(CH_2)_q$ in which q represents an integer of 3 to 5;

Y represents a $C_1$–$C_3$ alkyl group, a heterocyclic group containing 1 to 4 nitrogen atoms and 5 or 6 ring-membered atoms, or a $C_6$–$C_{10}$ aryl group;

k represents an integer of 1 to 3; and l represents an integer of 2 to 4.

2. A compound, a salt, a hydrate or a solvate according to claim 1, wherein $R_1$, $R_2$ and $R_3$ represent independently hydrogen atom, hydroxyl group, a $C_1$–$C_3$ alkoxy group, Het-$(CH_2)_m$—O— in which Het represents pyrrolyl group, imidazolyl group, pyrazolyl group, pyridyl group, pyrazinyl group, pyrimidinyl group, pyridazinyl group, pyrrolidinyl group, pyrrolinyl group, imidazolidinyl group, imidazolinyl group, pyrazolidinyl group, pyrazolinyl group, piperidyl group, or piperazinyl group and m represents an integer of 1 to 3, or $R_1$, $R_2$ and $R_3$ represent independently phenyl-$(C_1$–$C_3)$alkoxy group, pyrrolyl group, imidazolyl group, pyrazolyl group, pyridyl group, pyrazinyl group, pyrimidinyl group, pyridazinyl group, pyrrolidinyl group, pyrrolinyl group, imidazolidinyl group, imidazolinyl group, pyrazolidinyl group, pyrazolinyl group, piperidyl group, piperazinyl group, triazolidinyl group, triazolyl group, triazinyl group, tetrazolyl group, and tetrazinyl group, alternatively, $R_1$ and $R_2$ may form together to represent —O—$(CH_2)_n$—O— in which n represents an integer of 1 to 3;

$R_4$ represents a $C_1$–$C_7$ alkyl group, a $C_3$–$C_7$ cycloalkyl group or Ar—$(CH_2)_p$— in which Ar represents phenyl group, tolyl group, or naphthyl group, and p represents an integer of 1 to 3;

$R_5$ and $R_6$ represent independently hydrogen atom or a $C_1$–$C_3$ alkyl group, alternatively, $R_5$ and $R_6$ may form together to represent —$(CH_2)_q$— in which q represents an integer of 3 to 5;

Y represents a $C_1$–$C_3$ alkyl group, pyrrolyl group, imidazolyl group, pyrazolyl group, pyridyl group, pyrazinyl group, pyrimidinyl group, pyridazinyl group, pyrrolidinyl group, pyrrolinyl group, imidazolidinyl group, imidazolinyl group, pyrazolidinyl group, pyrazolinyl group, piperidyl group, piperazinyl group, triazolidinyl group, triazolyl group, triazinyl group, tetrazolyl group, and tetrazinyl group, phenyl group, tolyl group, or naphthyl group; and k represents an integer of 1 to 3; and l represents an integer of 2 to 4.

3. A compound, a salt, a hydrate or a solvate according to claim 1, wherein $R_1$, $R_2$ and $R_3$ independently represent hydrogen atom, hydroxyl group, a $C_1$–$C_3$ alkoxy group, Het-$(CH_2)_m$—O— in which Het represents pyridyl group and m represents an integer of 1 to 3, phenyl-$(C_1$–$C_3)$ alkoxy group, pyrrolyl group, imidazolyl group, pyrazolyl group, or triazolyl group, alternatively, $R_1$ and $R_2$ may form together to represent —O—$(CH_2)_n$—O— in which n represents an integer of 1 to 3;

$R_4$ represents a $C_1$–$C_7$ alkyl group, a $C_3$–$C_7$ cycloalkyl group, or Ar—$(CH_2)_p$— in which Ar represents phenyl group, and p represents an integer of 1 to 3;

$R_5$ and $R_6$ represent independently hydrogen atom or a $C_1$–$C_3$ alkyl group, alternatively, $R_5$ and $R_6$ may form together to represent —$(CH_2)_q$— in which q represents an integer of 3 to 5;

Y represents a $C_1$–$C_3$ alkyl group, pyridyl group, or phenyl group;

k represents an integer of 1 to 3; and l represents an integer of 2 to 4.

4. A compound, a salt, a hydrate or a solvate according to claim 1, wherein $R_1$, $R_2$ and $R_3$ represent independently hydrogen atom, a $C_1$–$C_3$ alkoxy group, Het-$(CH_2)_m$—O— in which Het represents 2-pyridyl group, 3-pyridyl group, or 4-pyridyl group, and m represents 1, or $R_1$, $R_2$ and $R_3$ represent independently phenylmethyloxy group, 1-pyrrolyl group, 1-imidazolyl group, 1-pyrazolyl group, or 1-triazolyl group, alternatively, $R_1$ and $R_2$ may form together to represent —O—$(CH_2)_n$—O— in which n represents 1;

$R_4$ represents a $C_1$–$C_7$ alkyl group, cyclopentyl group, or Ar—$(CH_2)_p$— in which Ar represents phenyl group and p represents 1 or 3;

$R_5$ represents a $C_1$–$C_3$ alkyl group and $R_6$ represents hydrogen atom, alternatively, $R_5$ and $R_6$ may form together to represent —$(CH_2)_q$— in which q represents 4;

Y represents 2-pyridyl group or phenyl group;

k represents 1 or 2; and l represents 3.

5. A compound, a salt, a hydrate or a solvate according to claim 1, wherein at least one of $R_1$, $R_2$ and $R_3$ represents Het-$(CH_2)_m$—O— in which Het represents 2-pyridyl group or 3-pyridyl group, and m represents 1,1-imidazolyl group, or 1-triazolyl group;

$R_4$ represents n-propyl group, n-pentyl group, cyclopentyl group, or Ar—$(CH_2)_p$— in which Ar represents phenyl group and p represents 1 or 3;

$R_5$ represents methyl group and $R_6$ represents hydrogen atom, alternatively, $R_5$ and $R_6$ may form together to represent —$(CH_2)_q$— in which q represents 4;

Y represents phenyl group;

k represents 1 or 2; and l represents 3.

6. A compound, a salt, a hydrate or a solvate according to claim 1, wherein the compound is N-{5-(1-imidazolyl)-2-methoxyphenyl}methyl-N-(1-pentyl)-N'-[2-{3-(4-phenyl-1-piperazinyl)propoxy}-6-methylphenyl]urea.

7. A pharmaceutical composition comprising as an active ingredient a substance selected from the group consisting of a compound, a salt, a hydrate or a solvate according to claim 1 together with a pharmaceutically acceptable carrier or coating.

8. An antihyperlipidemic agent comprising as an active ingredient a substance selected from the group consisting of a compound, a salt, a hydrate or a solvate according to claim 1.

9. A method for preventive and/or therapeutic treatment of hyperlipemia which comprises the step of administering to a patient suffering from hyperlipemia an effective amount of a substance selected from the group consisting of a compound, a salt, a hydrate and a solvate according to claim 1.

10. An antiarteriosclerotic agent comprising as an active ingredient a substance selected from the group consisting of a compound, a salt, a hydrate and a solvate according to claim 1.

11. A method for preventive and/or therapeutic treatment of arteriosclerosis which comprises the step of administering to a patient suffering form arteriosclerosis an effective amount of a substance selected from the group consisting of a compound, a salt, a hydrate and a solvate according to claim 1.

12. A cholesterol-lowering agent comprising as an active ingredient a substance selected from the group consisting of a compound, a salt, a hydrate and a solvate according to claim 1.

13. A method for preventive and/or therapeutic treatment of hypercholesterolemia which comprises the step of administering to a patient suffering from hypercholesterolemia an effective amount of a substance selected from the group consisting of a compound, a salt, a hydrate and a solvate according to claim 1.

14. A triglyceride-lowering agent comprising as an active ingredient a substance selected from the group consisting of a compound, a salt, a hydrate and a solvate according to claim 1.

15. A method for preventive and/or therapeutic treatment of hypertriglyceridemia which comprises the step of administering to a patient suffering form hypertriglyceridemia an effective amount of a substance selected from the group consisting of a compound a salt, a hydrate and a solvate thereof according to claim 1.

16. A substance according to claim 1, said substance being N-{5-(1-imidazolyl)-2-methoxyphenyl}methyl-N-(1-pentyl)-N'-[2-{3-(4-phenyl-1-piperazinyl)-propoxy}-6-methylphenyl]urea dihydrochloride or a hydrate thereof.

* * * * *